(12) United States Patent
Lau et al.

(10) Patent No.: US 7,229,405 B2
(45) Date of Patent: Jun. 12, 2007

(54) CARDIAC HARNESS DELIVERY DEVICE AND METHOD OF USE

(75) Inventors: Lilip Lau, Los Altos, CA (US); Joshua Wallin, San Jose, CA (US)

(73) Assignee: Paracor Medical, Inc., Sunnyvale, CA (US)

( * ) Notice: Subject to any disclaimer, the term of this patent is extended or adjusted under 35 U.S.C. 154(b) by 0 days.

(21) Appl. No.: 11/481,567

(22) Filed: Jul. 6, 2006

(65) Prior Publication Data

US 2007/0015958 A1    Jan. 18, 2007

Related U.S. Application Data

(63) Continuation-in-part of application No. 10/715,150, filed on Nov. 17, 2003.

(60) Provisional application No. 60/427,079, filed on Nov. 15, 2002.

(51) Int. Cl.
*A61F 2/00* (2006.01)
*A61F 13/00* (2006.01)

(52) U.S. Cl. ...................................................... 600/37

(58) Field of Classification Search ............ 600/16–18, 600/37; 128/897, 898; 606/1, 108, 110, 606/113, 127, 151, 140–142, 213
See application file for complete search history.

(56) References Cited

U.S. PATENT DOCUMENTS

| | | |
|---|---|---|
| 1,682,119 A | 8/1928 | Field |
| 2,278,926 A | 4/1942 | Hartwell |
| 2,826,193 A | 3/1958 | Vineberg |
| 3,464,322 A | 9/1969 | Pequignot |
| 3,513,836 A | 5/1970 | Sausse |
| 3,587,567 A | 6/1971 | Schiff |
| 3,613,672 A | 10/1971 | Schiff |
| 3,966,401 A | 6/1976 | Hancock et al. |
| 3,983,863 A | 10/1976 | Janke et al. |

(Continued)

FOREIGN PATENT DOCUMENTS

DE       3831 540 A1    4/1989

(Continued)

OTHER PUBLICATIONS

Bencini, Adriano, M.D., *The "Pneumomassage" of the Heart*, Surgery, vol. 39, No. 3, Mar. 1956.

(Continued)

*Primary Examiner*—Samuel G. Gilbert
(74) *Attorney, Agent, or Firm*—Fulwider Patton LLP

(57) ABSTRACT

A delivery system for delivering and mounting a cardiac harness on a heart including an elongate body having a proximal portion and a distal portion. The body includes a cavity sized to contain the cardiac harness in a compacted configuration and also includes a plurality of elongate push rods movable with respect to the body. The cardiac harness is releasably connected to the push rods such that, advancement of the push rods in a distal direction moves the cardiac harness from a compacted configuration, within the cavity, to an expanded configuration, outside the cavity. The push rods are configured to have varying stiffness along their length to provide sufficient flexibility to bend up to 90° to advance the cardiac harness onto the heart.

21 Claims, 42 Drawing Sheets

U.S. PATENT DOCUMENTS

| | | |
|---|---|---|
| 3,988,782 A | 11/1976 | Dardik et al. |
| 4,011,947 A | 3/1977 | Sawyer |
| 4,048,990 A | 9/1977 | Goetz |
| 4,065,816 A | 1/1978 | Sawyer |
| 4,108,161 A | 8/1978 | Samuels et al. |
| 4,192,293 A | 3/1980 | Asrican |
| 4,211,325 A | 7/1980 | Wright |
| 4,261,342 A | 4/1981 | Aranguren Duo |
| 4,306,318 A | 12/1981 | Mano et al. |
| 4,372,293 A | 2/1983 | Vijil-Rosales |
| 4,403,604 A | 9/1983 | Wilkinson et al. |
| 4,428,375 A | 1/1984 | Ellman |
| 4,512,471 A | 4/1985 | Kaster et al. |
| 4,536,893 A | 8/1985 | Parravicini |
| 4,545,783 A | 10/1985 | Vaughan |
| 4,628,937 A | 12/1986 | Hess et al. |
| 4,630,597 A | 12/1986 | Kantrowitz et al. |
| 4,665,906 A | 5/1987 | Jervis |
| 4,690,134 A | 9/1987 | Snyders |
| 4,697,703 A | 10/1987 | Will |
| 4,750,619 A | 6/1988 | Cohen et al. |
| 4,821,723 A | 4/1989 | Baker, Jr. et al. |
| 4,827,932 A | 5/1989 | Ideker et al. |
| 4,834,707 A | 5/1989 | Evans |
| 4,838,288 A | 6/1989 | Wright et al. |
| 4,840,626 A | 6/1989 | Linsky et al. |
| 4,863,016 A | 9/1989 | Fong et al. |
| 4,878,890 A | 11/1989 | Bilweis |
| 4,936,857 A | 6/1990 | Kulik |
| 4,957,477 A | 9/1990 | Lundback |
| 4,960,424 A | 10/1990 | Grooters |
| 4,973,300 A | 11/1990 | Wright |
| 4,976,730 A | 12/1990 | Kwan-Gett |
| 5,031,762 A | 7/1991 | Heacox |
| 5,057,117 A | 10/1991 | Atweh |
| 5,067,957 A | 11/1991 | Jervis |
| 5,087,243 A | 2/1992 | Avitall |
| 5,098,369 A | 3/1992 | Heilman et al. |
| 5,106,386 A | 4/1992 | Isner et al. |
| 5,119,804 A | 6/1992 | Anstadt |
| 5,131,905 A | 7/1992 | Grooters |
| 5,150,706 A | 9/1992 | Cox et al. |
| 5,169,381 A | 12/1992 | Snyders |
| 5,186,711 A | 2/1993 | Epstein |
| 5,190,546 A | 3/1993 | Jervis |
| 5,192,314 A | 3/1993 | Daskalakis |
| 5,197,978 A | 3/1993 | Hess |
| 5,256,132 A | 10/1993 | Snyders |
| 5,279,539 A | 1/1994 | Bohan et al. |
| 5,290,217 A | 3/1994 | Campos |
| 5,333,624 A | 8/1994 | Tovey |
| 5,336,254 A | 8/1994 | Brennen et al. |
| 5,344,442 A | 9/1994 | Deac |
| 5,352,184 A | 10/1994 | Goldberg et al. |
| 5,356,432 A | 10/1994 | Rutkow et al. |
| 5,366,460 A | 11/1994 | Eberbach |
| 5,382,528 A | 1/1995 | Wilk |
| 5,383,840 A | 1/1995 | Heilman et al. |
| 5,385,156 A | 1/1995 | Oliva |
| 5,385,229 A | 1/1995 | Bittmann et al. |
| 5,405,360 A | 4/1995 | Tovey |
| 5,429,584 A | 7/1995 | Chiu |
| 5,433,727 A | 7/1995 | Sideris |
| 5,456,711 A | 10/1995 | Hudson |
| 5,460,962 A | 10/1995 | Kemp |
| 5,500,015 A | 3/1996 | Deac |
| 5,507,779 A | 4/1996 | Altman |
| 5,509,428 A | 4/1996 | Dunlop |
| 5,524,633 A | 6/1996 | Heaven et al. |
| 5,533,958 A | 7/1996 | Wilk |
| 5,534,024 A | 7/1996 | Rogers et al. |
| 5,545,210 A | 8/1996 | Hess et al. |
| 5,558,617 A | 9/1996 | Heilman et al. |
| 5,571,215 A | 11/1996 | Sterman et al. |
| 5,582,616 A | 12/1996 | Bolduc et al. |
| 5,584,803 A | 12/1996 | Stevens et al. |
| 5,593,424 A | 1/1997 | Northrup III |
| 5,593,441 A | 1/1997 | Lichtenstein et al. |
| 5,597,378 A | 1/1997 | Jervis |
| 5,603,337 A | 2/1997 | Jarvik |
| 5,607,477 A | 3/1997 | Schindler et al. |
| 5,647,372 A | 7/1997 | Tovey et al. |
| 5,647,380 A | 7/1997 | Campbell et al. |
| 5,695,525 A | 12/1997 | Mulhauser et al. |
| 5,702,343 A | 12/1997 | Alferness |
| 5,713,954 A | 2/1998 | Rosenberg et al. |
| 5,727,569 A | 3/1998 | Benetti et al. |
| 5,749,839 A | 5/1998 | Kovacs |
| 5,782,746 A | 7/1998 | Wright |
| 5,800,334 A | 9/1998 | Wilk |
| 5,800,528 A | 9/1998 | Lederman et al. |
| 5,814,097 A | 9/1998 | Sterman et al. |
| 5,824,028 A | 10/1998 | Knisley |
| 5,836,311 A | 11/1998 | Borst et al. |
| 5,848,962 A | 12/1998 | Feindt et al. |
| 5,849,005 A | 12/1998 | Garrison et al. |
| 5,853,422 A | 12/1998 | Huebsch et al. |
| 5,855,601 A | 1/1999 | Bessler et al. |
| 5,865,791 A | 2/1999 | Whayne et al. |
| 5,876,432 A | 3/1999 | Lau et al. |
| 5,904,690 A | 5/1999 | Middleman et al. |
| 5,910,124 A | 6/1999 | Rubin |
| 5,927,284 A | 7/1999 | Borst et al. |
| 5,948,019 A | 9/1999 | Shu et al. |
| 5,957,977 A | 9/1999 | Melvin |
| 5,961,440 A | 10/1999 | Schweich, Jr. et al. |
| 5,976,069 A | 11/1999 | Navia et al. |
| 5,979,456 A | 11/1999 | Magovern |
| 5,984,857 A | 11/1999 | Buck et al. |
| 5,990,378 A | 11/1999 | Ellis |
| 6,007,486 A | 12/1999 | Hunt et al. |
| 6,015,378 A | 1/2000 | Borst et al. |
| 6,024,096 A | 2/2000 | Buckberg |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,071,303 A | 6/2000 | Laufer |
| 6,076,013 A | 6/2000 | Brennan et al. |
| 6,077,214 A | 6/2000 | Mortier et al. |
| 6,077,218 A | 6/2000 | Alferness |
| 6,079,414 A | 6/2000 | Roth |
| 6,085,754 A | 7/2000 | Alferness et al. |
| 6,095,968 A | 8/2000 | Snyders |
| 6,110,100 A | 8/2000 | Talpade |
| 6,117,159 A | 9/2000 | Huebsch et al. |
| 6,117,979 A | 9/2000 | Hendriks et al. |
| 6,123,662 A | 9/2000 | Alferness et al. |
| 6,125,852 A | 10/2000 | Stevens et al. |
| 6,126,590 A | 10/2000 | Alferness |
| 6,155,968 A | 12/2000 | Wilk |
| 6,155,972 A | 12/2000 | Nauertz et al. |
| 6,162,168 A | 12/2000 | Schweich, Jr. et al. |
| 6,165,119 A | 12/2000 | Schweich, Jr. et al. |
| 6,165,120 A | 12/2000 | Schweich, Jr. et al. |
| 6,165,121 A | 12/2000 | Alferness |
| 6,165,122 A | 12/2000 | Alferness |
| 6,166,184 A | 12/2000 | Hendriks et al. |
| 6,169,922 B1 | 1/2001 | Alferness et al. |
| 6,174,279 B1 | 1/2001 | Girard |
| 6,179,791 B1 | 1/2001 | Krueger |
| 6,183,411 B1 | 2/2001 | Mortier et al. |
| 6,190,408 B1 | 2/2001 | Melvin |
| 6,193,648 B1 | 2/2001 | Krueger |
| 6,206,820 B1 | 3/2001 | Kazi et al. |

| | | |
|---|---|---|
| 6,214,047 B1 | 4/2001 | Melvin |
| 6,217,894 B1 | 4/2001 | Sawhney et al. |
| 6,221,103 B1 | 4/2001 | Melvin |
| 6,224,540 B1 | 5/2001 | Lederman et al. |
| 6,230,714 B1 | 5/2001 | Alferness et al. |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,282,445 B1 | 8/2001 | Reinhardt et al. |
| 6,287,250 B1 | 9/2001 | Peng et al. |
| 6,293,906 B1 | 9/2001 | Vanden Hoek et al. |
| 6,306,141 B1 | 10/2001 | Jervis |
| 6,312,725 B1 | 11/2001 | Wallace et al. |
| 6,352,710 B2 | 3/2002 | Sawhney et al. |
| 6,360,749 B1 | 3/2002 | Jayaraman |
| 6,375,608 B1 | 4/2002 | Alferness |
| 6,390,976 B1 | 5/2002 | Spence et al. |
| 6,402,679 B1 | 6/2002 | Mortier et al. |
| 6,402,680 B2 | 6/2002 | Mortier et al. |
| 6,406,420 B1 | 6/2002 | McCarthy et al. |
| 6,409,760 B1 | 6/2002 | Melvin |
| 6,416,459 B1 | 7/2002 | Haindl |
| 6,425,856 B1 | 7/2002 | Shapland et al. |
| 6,432,039 B1 | 8/2002 | Wardle |
| 6,451,025 B1 | 9/2002 | Jervis |
| 6,482,146 B1 | 11/2002 | Alferness et al. |
| 6,517,570 B1 | 2/2003 | Lau et al. |
| 6,537,203 B1 | 3/2003 | Alferness et al. |
| 6,544,168 B2 | 4/2003 | Alferness |
| 6,547,821 B1 | 4/2003 | Taylor et al. |
| 6,564,094 B2 | 5/2003 | Alferness et al. |
| 6,567,699 B2 | 5/2003 | Alferness et al. |
| 6,569,082 B1 | 5/2003 | Chin |
| 6,572,533 B1 | 6/2003 | Shapland et al. |
| 6,575,921 B2 | 6/2003 | Vanden Hoek et al. |
| 6,579,226 B2 | 6/2003 | Vanden Hoek et al. |
| 6,582,355 B2 | 6/2003 | Alferness et al. |
| 6,587,734 B2 | 7/2003 | Okuzumi |
| 6,595,912 B2 | 7/2003 | Lau et al. |
| 6,602,184 B2 | 8/2003 | Lau et al. |
| 6,612,978 B2 | 9/2003 | Lau et al. |
| 6,612,979 B2 | 9/2003 | Lau et al. |
| 6,620,095 B2 | 9/2003 | Taheri |
| 6,633,780 B1 | 10/2003 | Berger |
| 6,645,139 B2 | 11/2003 | Haindl |
| 6,663,558 B2 | 12/2003 | Lau et al. |
| 6,673,009 B1 | 1/2004 | Vanden Hoek et al. |
| 6,682,474 B2 | 1/2004 | Lau et al. |
| 6,682,475 B2 | 1/2004 | Cox et al. |
| 6,682,476 B2 | 1/2004 | Alferness et al. |
| 6,685,620 B2 | 2/2004 | Gifford, III et al. |
| 6,685,627 B2 | 2/2004 | Jayaraman |
| 6,689,048 B2 | 2/2004 | Vanden Hoek et al. |
| 6,695,769 B2 | 2/2004 | French et al. |
| 6,699,259 B2 | 3/2004 | Fogarty et al. |
| 6,701,929 B2 | 3/2004 | Hussein |
| 6,702,732 B1 | 3/2004 | Lau et al. |
| 6,723,041 B2 | 4/2004 | Lau et al. |
| 6,730,016 B1 | 5/2004 | Cox et al. |
| 6,755,779 B2 | 6/2004 | Vanden Hoek et al. |
| 6,759,431 B2 | 7/2004 | Hunter et al. |
| 6,818,018 B1 | 11/2004 | Sawhney |
| 6,833,408 B2 | 12/2004 | Sehl et al. |
| 6,876,887 B2 | 4/2005 | Okuzumi |
| 6,881,185 B2 | 4/2005 | Vanden Hock et al. |
| 6,887,192 B1 | 5/2005 | Whayne et al. |
| 6,893,392 B2 | 5/2005 | Alferness |
| 6,896,652 B2 | 5/2005 | Alferness et al. |
| 6,902,522 B1 | 6/2005 | Walsh et al. |
| 6,902,524 B2 | 6/2005 | Alferness et al. |
| 6,908,426 B2 | 6/2005 | Shapland et al. |
| 7,022,063 B2 | 4/2006 | Lau et al. |
| 7,077,802 B2 | 7/2006 | Lau et al. |
| 7,081,086 B2 | 7/2006 | Lau et al. |
| 7,097,613 B2 | 8/2006 | Lau et al. |
| 2001/0293134 | 10/2001 | Alferness et al. |
| 2001/0047122 A1 | 11/2001 | Vanden Hoek et al. |
| 2002/0007216 A1 | 1/2002 | Melvin |
| 2002/0022880 A1 | 2/2002 | Melvin |
| 2002/0028981 A1 | 3/2002 | Lau et al. |
| 2002/0068849 A1 | 6/2002 | Schweich, Jr. et al. |
| 2002/0077524 A1 | 6/2002 | Schweich, Jr. et al. |
| 2002/0077637 A1 | 6/2002 | Vargas et al. |
| 2002/0082647 A1 | 6/2002 | Alferness et al. |
| 2002/0091296 A1 | 7/2002 | Alferness |
| 2002/0103511 A1 | 8/2002 | Alferness et al. |
| 2003/0004547 A1 | 1/2003 | Owen et al. |
| 2003/0060674 A1 | 3/2003 | Gifford, III et al. |
| 2003/0060677 A1 | 3/2003 | French et al. |
| 2003/0060895 A1 | 3/2003 | French et al. |
| 2003/0065248 A1 | 4/2003 | Lau et al. |
| 2003/0199733 A1 | 10/2003 | Shapland et al. |
| 2003/0199955 A1 | 10/2003 | Struble et al. |
| 2003/0229265 A1 | 12/2003 | Girard et al. |
| 2004/0106848 A1 | 6/2004 | Lau et al. |
| 2004/0133069 A1 | 7/2004 | Shapland et al. |
| 2004/0171907 A1 | 9/2004 | Alferness et al. |
| 2004/0171908 A1 | 9/2004 | Alferness et al. |
| 2004/0210104 A1 | 10/2004 | Lau et al. |
| 2004/0230091 A1 | 11/2004 | Lau et al. |
| 2005/0033322 A1 | 2/2005 | Lau et al. |
| 2005/0049611 A1 | 3/2005 | Lau et al. |
| 2005/0055032 A1 | 3/2005 | Lau et al. |
| 2005/0059854 A1 | 3/2005 | Hoek et al. |
| 2005/0059855 A1 | 3/2005 | Lau et al. |
| 2005/0085688 A1 | 4/2005 | Girard et al. |
| 2005/0090707 A1 | 4/2005 | Lau et al. |
| 2005/0102010 A1 | 5/2005 | Lau et al. |
| 2005/0102016 A1 | 5/2005 | Lau et al. |
| 2005/0107661 A1 | 5/2005 | Lau et al. |
| 2005/0137673 A1 | 6/2005 | Lau et al. |
| 2005/0169958 A1 | 8/2005 | Hunter et al. |
| 2005/0169959 A1 | 8/2005 | Hunter et al. |
| 2005/0182290 A1 | 8/2005 | Lau et al. |
| 2005/0256368 A1 | 11/2005 | Lau et al. |

FOREIGN PATENT DOCUMENTS

| | | |
|---|---|---|
| DE | 38 31 540 C2 | 6/1993 |
| DE | 295 17 393 U1 | 3/1996 |
| EP | 0 370 931 A1 | 5/1990 |
| EP | 0 280 564 B1 | 6/1993 |
| EP | 0 583 012 B1 | 7/1996 |
| EP | 0 791 330 A3 | 8/1997 |
| EP | 0 919 193 A1 | 6/1999 |
| FR | 2 527 435 | 12/1983 |
| FR | 2 645 739 | 10/1990 |
| GB | 2 115 287 A | 9/1983 |
| GB | 2 209 678 A | 5/1989 |
| JP | 60-203250 | 10/1985 |
| JP | 1-145066 | 6/1989 |
| JP | 1-271829 | 10/1989 |
| SU | 1009457 | 4/1983 |
| SU | 1734767 A1 | 5/1992 |
| WO | WO 91/19465 | 12/1991 |
| WO | WO 95/06447 | 3/1995 |
| WO | WO 96/04852 | 2/1996 |
| WO | WO 96/40356 | 12/1996 |
| WO | WO 97/20505 | 6/1997 |
| WO | WO 97/24101 | 7/1997 |
| WO | WO 98/03213 | 1/1998 |
| WO | WO 98/14136 | 4/1998 |
| WO | WO 98/26738 | 6/1998 |
| WO | WO 98/29041 | 7/1998 |
| WO | WO 98/58598 | 12/1998 |
| WO | WO 00/02500 | 1/1999 |

| | | |
|---|---|---|
| WO | WO 99/11201 | 3/1999 |
| WO | WO 99/30647 | 6/1999 |
| WO | WO 99/44534 | 9/1999 |
| WO | WO 99/44680 | 9/1999 |
| WO | WO 99/53977 | 10/1999 |
| WO | WO 99/56655 | 11/1999 |
| WO | WO 00/06026 | 2/2000 |
| WO | WO 00/06027 | 2/2000 |
| WO | WO 00/06028 | 2/2000 |
| WO | WO 00/13722 | 3/2000 |
| WO | WO 00/16700 | 3/2000 |
| WO | WO 00/18320 | 4/2000 |
| WO | WO 00/28912 | 5/2000 |
| WO | WO 00/28918 | 5/2000 |
| WO | WO/0036695 | 6/2000 |
| WO | WO 00/42919 | 7/2000 |
| WO | WO 00/45735 | 8/2000 |
| WO | WO 00/48795 | 8/2000 |
| WO | WO 00/62727 | 10/2000 |
| WO | WO 00/74769 | 12/2000 |
| WO | WO 01/17437 | 3/2001 |
| WO | WO 01/21098 | 3/2001 |
| WO | WO 01/50981 | 7/2001 |
| WO | WO 01/67985 | 9/2001 |
| WO | WO 01/85061 | 11/2001 |
| WO | WO 01/91667 | 12/2001 |
| WO | WO 01/95380 | 12/2001 |
| WO | WO 01/95831 | 12/2001 |
| WO | WO 01/95832 | 12/2001 |
| WO | WO 02/13726 | 2/2002 |
| WO | WO 02/19917 | 3/2002 |
| WO | WO 03/026483 | 4/2003 |
| WO | WO 03/026484 | 4/2003 |
| WO | WO 03/026485 | 4/2003 |

OTHER PUBLICATIONS

Anstadt, George L., et al., *A New Instrument for Prolonged Mechanical Cardiac Massage*, Abstracts of the 38th Scientific Sessions, Supplemet II to Circulation, vol. 31 and 32, pp. 375-394, Oct. 1965.

Lev, Maurice, M.D., et al., *Single (Primitive) Venticle*, Circulation, vol. 39, pp. 577-591.

Paling, D.F., *Warp Knitting Technology*, 1970.

Edie, Richard N., M.D., et al., *Surgical Repair of Single Ventricle*, The Journal of Thoracic and Cardiovascular Surgery, vol. 66, No. 3, pp. 350-360, Sep. 1972.

McGoon, Dwight C., M.D., et al., *Correction of the Univentricular Heart Having Two Atriovantricular Valves*, The Journal of Thoracic and Cardiovascular Surgery, vol. 74, No. 2, pp. 218-226, Aug. 1977.

Doty, Donald B., et al., *Septation of the Univentricular Heart: Transatrial Approach*, The Journal of Thoracic and Cardiovascular Surgery, vol. 78, No. 3, pp. 424-430, Sep. 1979.

Schetky, L. McDonald, *Shap- Memory Alloys*, Scientific American, vol. 241, No. 5, pp. 74-82, Nov. 1979.

Melton, K.N., et al., *Alloys With Two-Shape Memory Effect*, Mechanical Engineering, pp. 42-43, Mar. 1980.

Feldt, Robert H., M.D., et al., *Current Status of the Septation Procedure for Univentricular Heart*, The Journal of Thoracic and Cardiovascular Surgery, vol. 82, No. 1, pp. 93-97, Jul. 1981.

Carpentier, A., et al., *Myocardial Substitution With Stimulated Skeletal Muscle: First Successful Clinical Case*, The Lancet, Jun. 1, 1985.

Anstadt, George L. et al., *Direct Mechanical Ventricular Actuation: A Review*, Resuscitation, pp. 7-23, 1991.

Anstadt, Mark P., M.D., et al., *Pulsatile Reperfusion After Cardiac Arrest Improves Neurologic Outcome*, American Surgery, vol. 214, No. 4, pp. 478-490, Oct. 1991.

Schumacker, Harris B., Jr., *Chapte 21: Cardiac Aneurysms, The Evolution of Cardiac Surgery*, pp. 159-165, 1992.

Savage, Edward B., M.D., et al., *Repair of Left Ventricular Aneurysm*, The Journal of Thoracic and Cardiovascular Surgery, vol. 104, No. 3, pp. 752-762, Sep. 1992.

Carpentier, Alain, M.D., Ph.D., et al., *Dynamic Cardiomyoplasty at Seven Years*, The Journal of Thoracic and Cardiovascular Surgery, vol. 106, No. 1, pp. 42-54, Jul. 1993.

Capouya, Eli R., M.D., et al., *Girdling Effect of Nonstimulated Cardiomyoplasty on Left Ventricular Function*, Annals of Thoracic Surgeons, vol. 56, pp. 867-871, 1993.

Chekanov, Valeri, M.D., Ph.D., *Nonstimulated Cardiomyoplasty Wrap Attenuated the Degree of Left Ventricular Enlargement*, Annals of Thoracic Surgeons, vol. 57, pp. 1684-1690, 1997.

Chiu, Ray C.-J, *Using Skeletal Muscle for Cardiac Assistance*, Scientific American, pp. 68-77, Nov./Dec. 1994.

Kass, David A., M.D., et al., *Reverse Remodeling From Cardiomyplasty in Human Heart Failure: External Constraint Versus Active Assist*, Circulation, vol. 91, No. 9, pp. 2314-2318, May 1, 1995.

Vaynblat, Mikhail, M.D., et al., *Cardiac Binding in Experimental Heart Failure*, Annals of Thoracic Surgery (Abstract), Supplement to Circulation, vol. 92, Suppl. 1, 1995.

Levin, Howard R., M.D., et al., *Reversal of Chronic Ventricular Dilation in Patients With End-Stage Cardiomyoplasty by Prolonged Mechanical Unloading*, Circulation, vol. 91, No. 11, pp. 2717-2720, 1995.

Chaudhry, Pervaiz A., M.D., et al., *Acute Ventricular Reduction with Acorn's Cardiac Support Device Prevents Progressive Left Ventricular Dysfunction and Remodeling in Dogs With Advanced Heart Failure*, Cardiothoracic Surgery, pp. 146-148, 1996.

Oh, Joong Hwan, M.D., et al., *Mechanisms of Dynamic Cardiomyoplasty: Current Concepts*, Journal of Cardiac Surgery, vol. 11, pp. 194-199, 1996.

Badhwar, Vinay, *Power Generation From Four Skeletal Muscle Configurations Design Implications for a Muscle Powered Cardiac Assis Device*, ASAIO Journal, vol. 43, pp. M651-M657, 1997.

Westaby, Stephen, et al., *Landmarks in Cardiac Surgery*, pp. 198-199, 1997.

Cox, James L., *Left Ventricular Aneurysms: Pathophysiologic Observations and Standard Resection*, Seminars in Thoracic and Cardiovascular Surgery, vol. 9, No. 2, pp. 113-112, Apr. 1997.

Coletta, C., et al., *Prognosic Value of Left Ventricular Volume Response During Dobutamine Stress Echocardiography*, European Heart Journal, vol. 18, pp. 1599-1603, Oct. 1997.

Capomolla, Soccorso, M.D., et al., *Dobutamine and Nitroprusside Infusion in Patients With Severe Congestive Heart Failure: Hemodynamic Improvement by Discordant Effects on Mitral Regurgitation. Left Atrial Function, and Ventricular Function*, American Heart Journal, 1089-1098, Dec. 1997.

Oh, Joong Hwan, *The Effects of Prosthetic Cardiac Binding and Adynamic Cardiomyoplasty in a Model of Dilated Cardiomyopath*, The Journal of Thoracic and Cardiovascular Surgery, vol. 116, No. 1, pp. 148-153, 1998.

Cohn, Jay N., M.D., *Preventing Congestive Heart Failure*, American Family Physician, 6 pages, Apr. 15, 1998.

Cohn, Jay N., M.D., *Structural Basis for Heart Failure: Ventricular Remodeling and Its Pharmacological Inhibition*, Circulation, vol. 91, No. 10, pp. 2504-2507, May 15, 1995.

Gaudron, Peter, M.D., et al., *Progressive Left Ventricular Dysfunction and Remodeling After Myocardial Infarction*, Circulation, vol. 87, pp. 755-763, Mar. 1993.

Pfeiffer, Marc A., M.D., et al., *Ventricular Remodeling After Myocardial Infarction: Experimental Observations and Clinical Implications*, Circulation, vol. 81, No. 4, pp. 1161-1172, Apr. 1990.

Guasp, Francisco Torrent, *Una protesis contentiva para el tratamiento de le microcardiopatio dilatads*, Revista Espannõla de Cardiologia, vol. 51, No. 7, Jul. 1998.

Power, J.M., et al., *Passive Ventricular Constraint Amends the Course of Heart Failure: A Study in an Ovine Model of Dilated Cardiomyopathy*, Cardiovascular Research, vol. 44, pp. 549-555, 1999.

Frazier, O.H., M.D., et al., *Left Ventricular Assist System as a Bridge to Myocardial Recovery*, Annals of Thoracic Surgery, vol. 68, pp. 734-741, 1999.

Melvin, David B., *Ventricular Radius Reduction Without Resection: A Computational Analysis, ASAIO Journal*, pp. 160-165, 1999.

*ABSTRACTS—Heart Failure*, JACC Feb. 1999.

Raman, Jai S., Fracs, et al., *Ventricular Containment as an Adjunctive Procedure in Ischemic Cardiomyopathy: Early Results, Annals of Thoracic Surgery*, vol. 70, pp. 1124-1126, Jan. 2000.

McCarthy, Patrick M., et al., *Device Based Left Ventricular Shape Change Immediately Reduces Left Ventricular Volume and Increased Ejection Fraction in a Pacing Induced Cardiomyopathy Model in Dogs*, JACC, Feb. 2000.

Chaudhry, Pervaiz A., M.D., et al., *Passive Epicardial Containment Prevents Ventricular Remodeling in Heart Failure, Annals of Thoracic Surgeons*, vol. 70, pp. 1275-1280, 2000.

Acorn Cardiovascular, Inc., *CSD Specifications Acorn Cardiac Support Device*, 2000.

*Heart "jacket" could help stop heart failure progression, Clinicia*, No. 916, Jul. 2000.

Acorn Cardiovascular, Inc., *CorpCap™ Cardiac Support Device* Pamphlet, Jun. 2001.

*Medtronic's InSync Cardiac Resynchronization Therapy Device Approved by FDA*, (Press Release) Aug. 28, 2001.

Oz, Mehmet C., M.D., *Passive Ventricular Constraint for the Treatment of Congestive Heart Failure, Annals of Thoracic Surgery*, vol. 71, pp. 5185-5187, 2001.

Abstract Supplement, *European Heart Journal*, vol. 22, Sep. 2001.

Gorman, J., *Self-Sutures: A New Material Knots Up On Its Own, Science News*, vol. 161, p. 262, Apr. 27, 2002.

Mann, Douglas, L., M.D., *Basic Mechanisms of Remodeling and Reverse Remodeling*, presented at 6th Annual Scientific Meeting of the Heart Failure Society of America, Sep. 24, 2002.

Bocchi, Edimar a., M.D., *Arrhythmias and Sudden Death After Dynamic Cardiomyoplasty, Circulation*, vol. 90. No. 5, Part 2, pp. 11-107 thru 11-111, Nov. 1994.

Chachques, Juan C., M.D., *Study of Muscular and Ventricular Function in Dynamic Cardiomyoplasty: A Ten-Year Follow-Up, The Journal of Heart of Lung Transplantation*, vol. 16, No. 8, pp. 854-868, Aug. 1997.

Dullum, Mercedes K.C., M.D., et al., *Less Invasive Surgical Management of Heart Failure by Cardiac Support Device Implantation on the Beating Heart*. The Heart Surgery Forum, #2001-1818, pp. 361-363, Jan. 4-7, 2001.

Macris, Michael P. M.D., et al., *Minimally Invasive Access of the Normal Preicardium: Initial Clinical Experience with a Novel Device, Clinical Cardiology*, vol. 22 (Suppl. 1), pp. 1-36 thru 1-39, 1999.

Thakur, Ranjan K., M.D., et al., *Latissimus Dorsi Dynamic Cardiomyoplasty: Role of Combined ICD Implantation, Journal of Cardiac Surgery*, vol. 10, pp. 295-297, 1995.

Application for U.S. Appl. No. 10/314,696, filed Dec. 9, 2002, published on Apr. 3, 2003; Inventors: Lau et al.

Application for U.S. Appl. No. 10/704,376, filed Nov. 7, 2003; Inventor: Lau.

Application for U.S. Appl. No. 10/715,150, filed Nov. 17, 2003 published on Mar. 10, 2005; Inventor: Lau.

Application for U.S. Appl. No. 10/338,934, filed Jan. 7, 2003; Inventor: Lau.

Application for U.S. Appl. No. 10/838,002, filed May 3, 2004 published Oct. 21, 2004; Inventor: Lau et al.

Application for U.S. Appl. No. 10/939,721, filed Sep. 23, 2004 published Feb. 10, 2005; Inventor: Lau et al.

Application for U.S. Appl. No. 10974,237, filed Oct. 27, 2004; Inventor: Lau et al.

Application for U.S. Appl. No. 10/967,955, filed Oct. 18, 2004 published Mar. 3, 2005; Inventor: Lau et al.

Application for U.S. Appl. No. 11/343,926, filed Jan. 30, 2006; Inventor: Lau et al.

Application for U.S. Appl. No. 10/995,695, filed Nov. 23, 2004 published Apr. 28, 2005; Inventor: Lau et al.

Application for U.S. Appl. No. 11/304,070, filed Dec. 14, 2005; Inventor: Lau et al.

Application for U.S. Appl. No. 11/109,175, filed Apr. 18, 2005 published Aug. 18, 2005; Inventor: Lau et al.

Application for U.S. Appl. No. 11/187,276, filed Jul. 21, 2005 published Nov. 17, 2005; Inventor: Lau et al.

Application for U.S. Appl. No. 11/481,567, filed Jul. 6, 2006; Inventor: Lau et al.

Application for U.S. Appl. No. 10/693,577, filed Oct. 23, 2003 published Jun. 3, 2004; Inventor: Lau et al.

Application for U.S. Appl. No. 10/865,086, filed Jun. 9, 2004 published Nov. 18, 2004; Inventor: Lau et al.

Application for U.S. Appl. No. 11/012,833, filed Dec. 14, 2004 published May 19, 2005; Inventor: Lau et al.

Application for U.S. Appl. No. 11/008,733, filed Dec. 8, 2004 published May 12, 2005; Inventor: Lau et al.

Application for U.S. Appl. No. 11/317,624, filed Dec. 22, 2005; Inventor: Lau et al.

Wharton, J. Marcus, et al., *Electrophysiological Effects of Monophasic and Biphasic Stimuli in Normal and Infarcted Dogs, PACE*, vol. 13, pp. 1158-1172, Sep. 1990.

Shabetai, Ralph, *The Role of the Pericardium in the Pathophysiology of Heart Failure, Congestive Heart Failure, Second Edition*, Chapter 9, pp. 157-187, 2000.

Cohn, Jay N., M.D., *The Management of Chronic Heart Failure, The New England Journal of Medicine*, vol. 335, No. 7, pp. 490-498, Aug. 15, 1996.

Zhou, Xiaohong, et al., *Epicardial Mapping of Ventricular Defibrillation With Monophasic and Biphasic Shocks in Dogs, Circulation Research*, vol. 72, No. 1, pp. 145-160, Jan. 1993.

Shorofsky, Stephen R., et al., *Comparison of Step-Down and Binary Search Algorithms for Determination of Defibrillation Threshold in Humans, PACE*, vol. 27, pp. 218-220, Feb. 2004.

Gold, Michael R., M.D., et al., *Comparison of Single- and Dual-Coil Active Pectoral Defibrillation Lead Systems, Journal of the American College of Cardiology*, vol. 31, No. 6, pp. 1391-1394, May 1998.

Rinaldi, C. Aldo, *A Randomized Prospective Study of Single Coil Versus Dual Coil Defibrillation in Patients With Ventricular Arrhythmias Undergoing Implantable Cardioverier Defibrillator Therapy, PACE*, vol. 26, pp. 1684-1690, Aug. 2003.

Schwartzman, David, M.D., et al., *Serial Defibrillation Lead Impedance in Patients with Epicardial and Nonthoracotomy Lead Systems, Journal of Cardiovascular Electrophysiology*, vol. 7, No. 8, pp. 697-703, Aug. 1996.

Sandstedt, Bengt, et al., *Bidirectional Defibrillation Using Implantable Defibrillators: A Prospective Randomized Comparison Between Pectoral and Abdominal Active Generators, PACE*, vol. 24, Part 1, pp. 1343-1353, Sep. 2001.

Schulte, B., et al., *Dual-Coil vs. Single-Coil Active Pectoral Implantable Defibrillator Lead Systems: Defibrillation Lead Requirements and Probability of Defibrillation Success at Multiples of the Defibrillation Energy Requirements, Europace*, vol. 3, pp. 177-180, Jul. 2001.

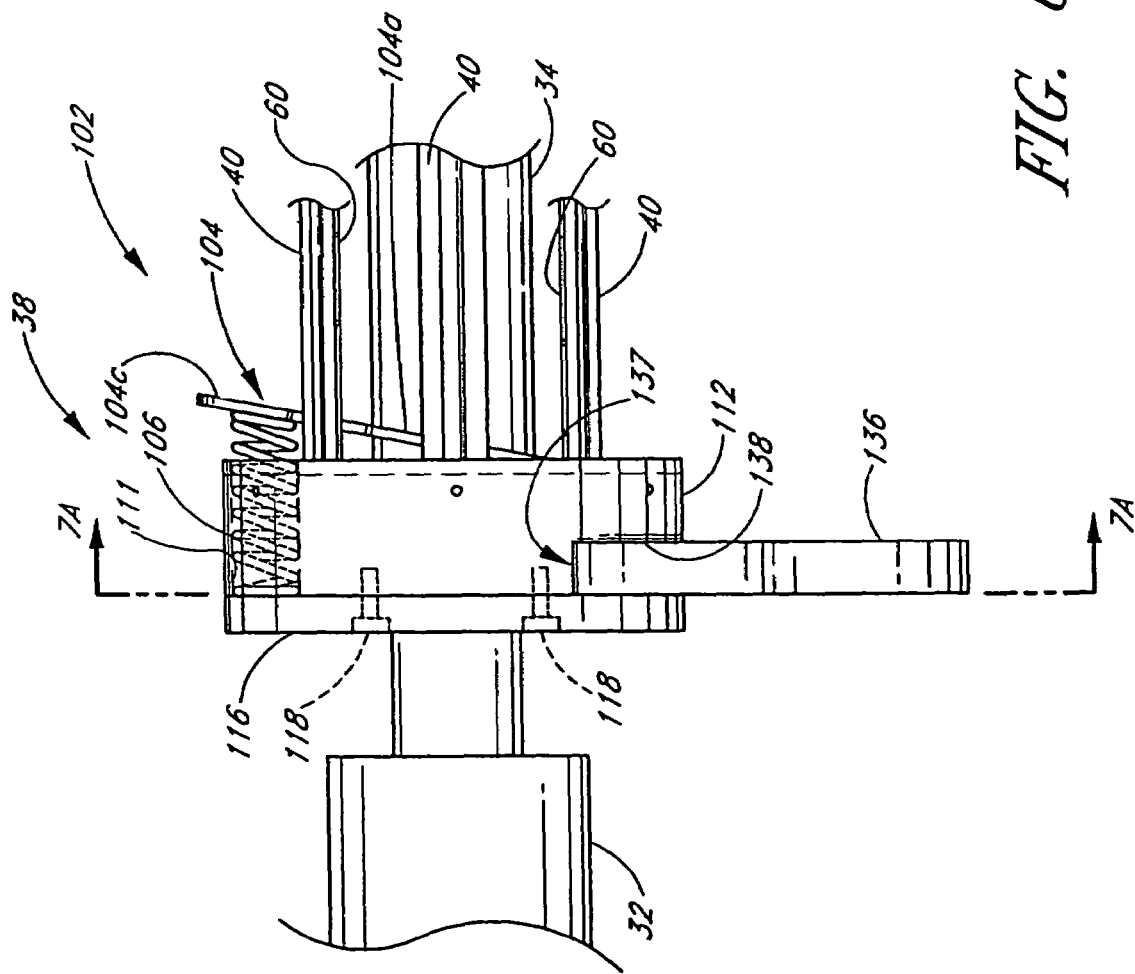

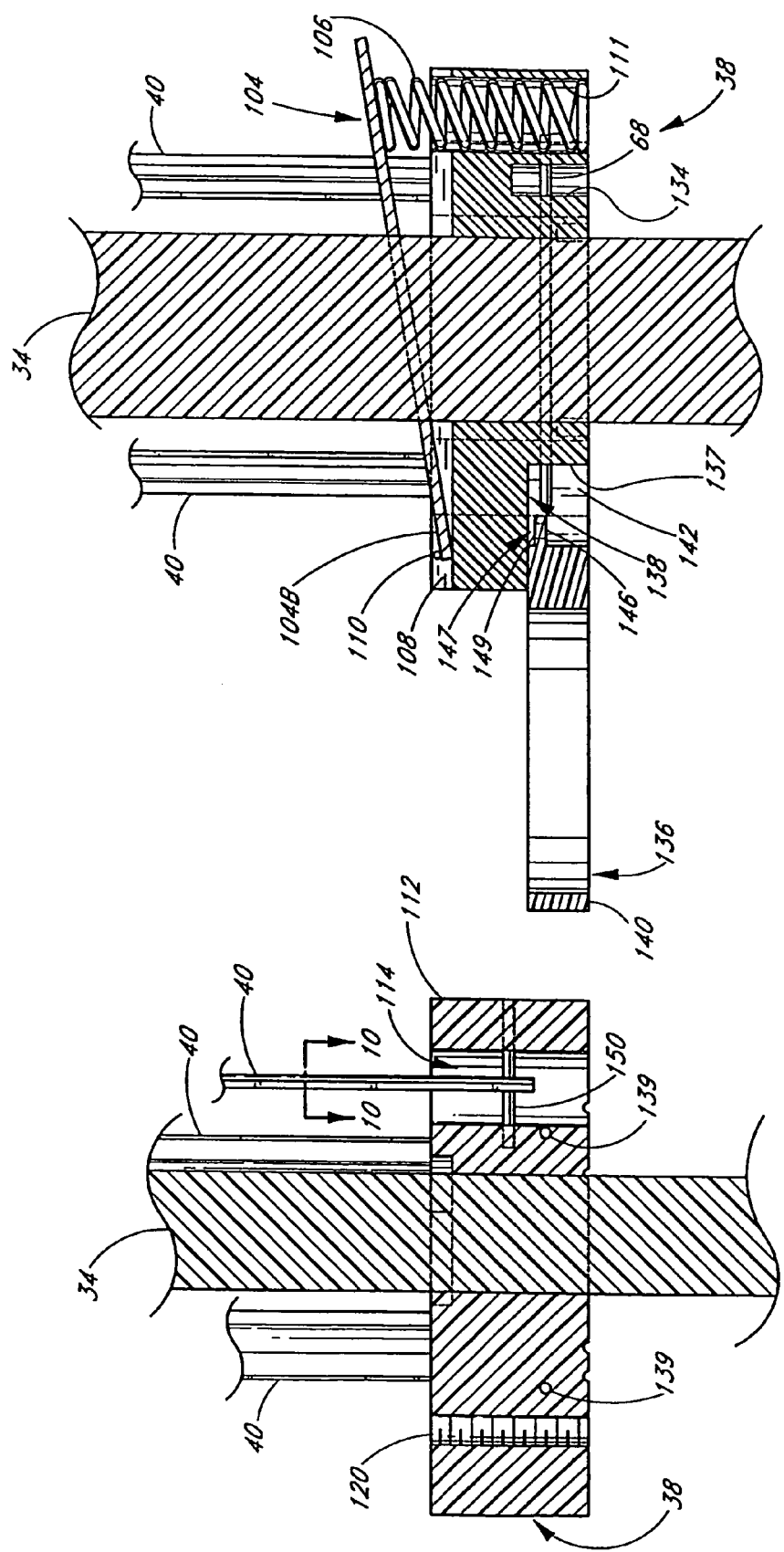

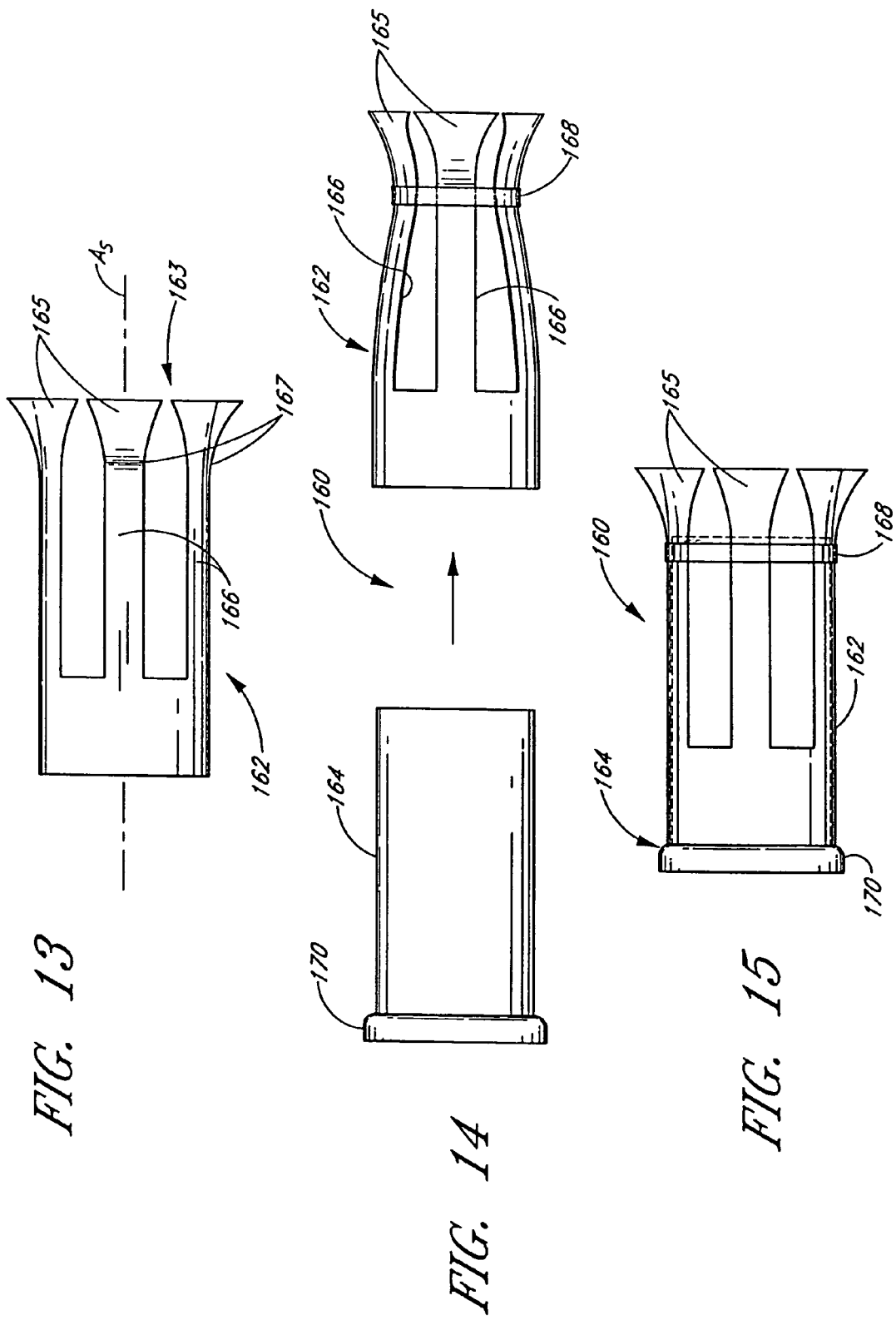

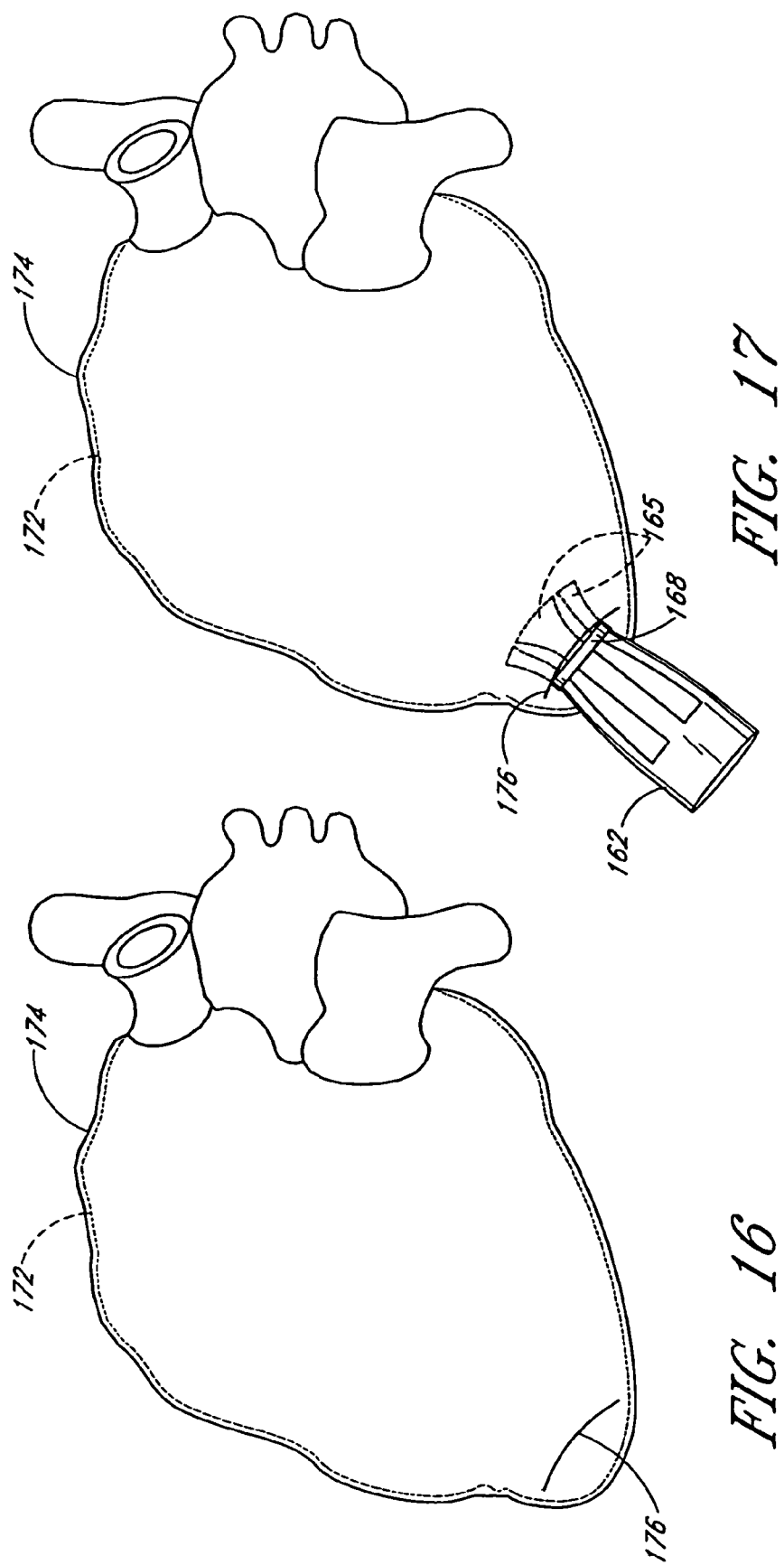

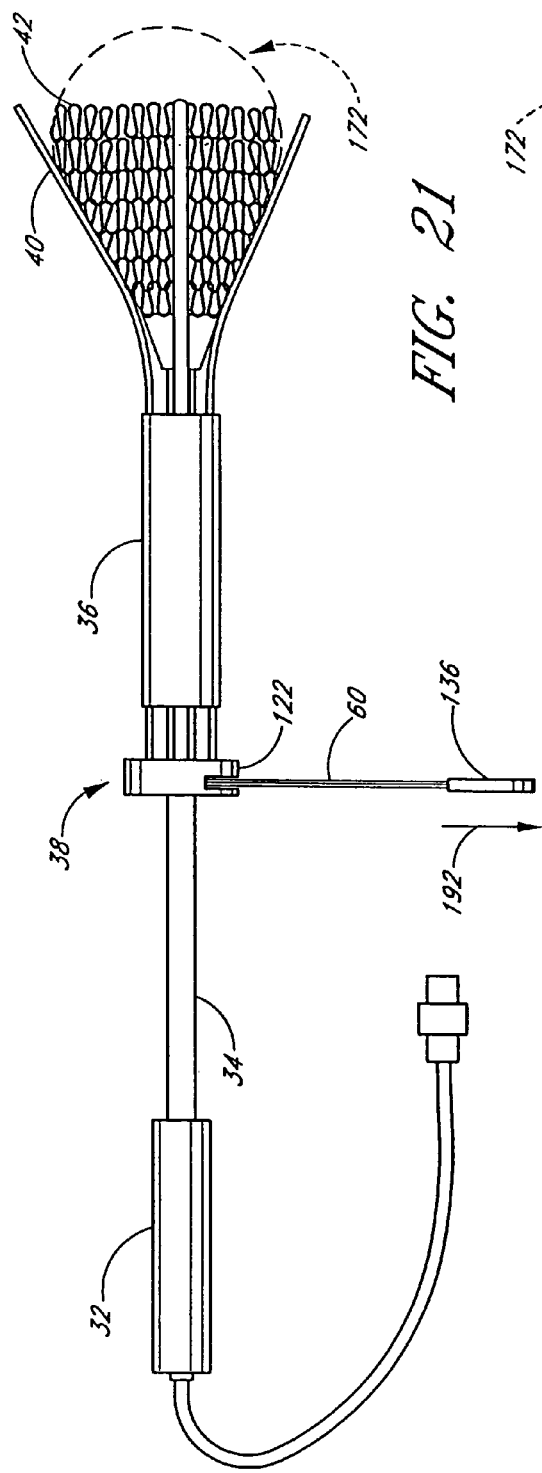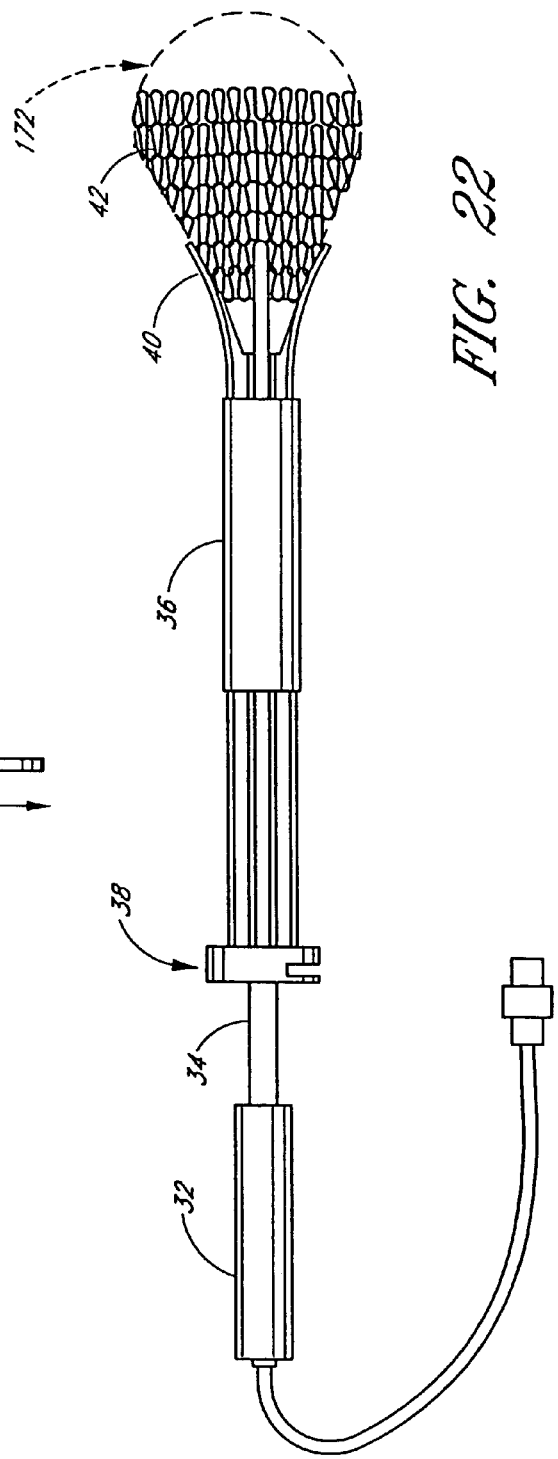

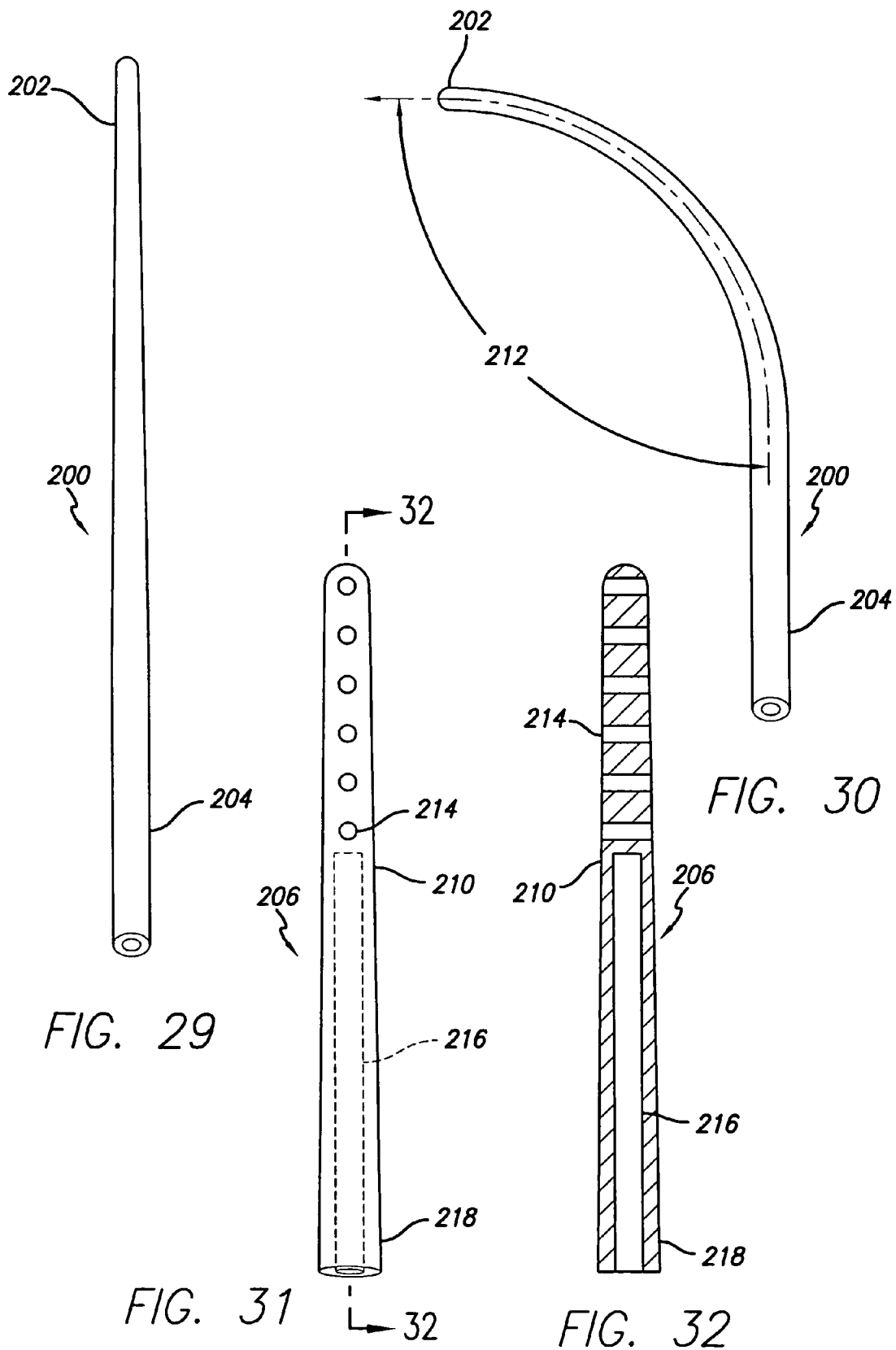

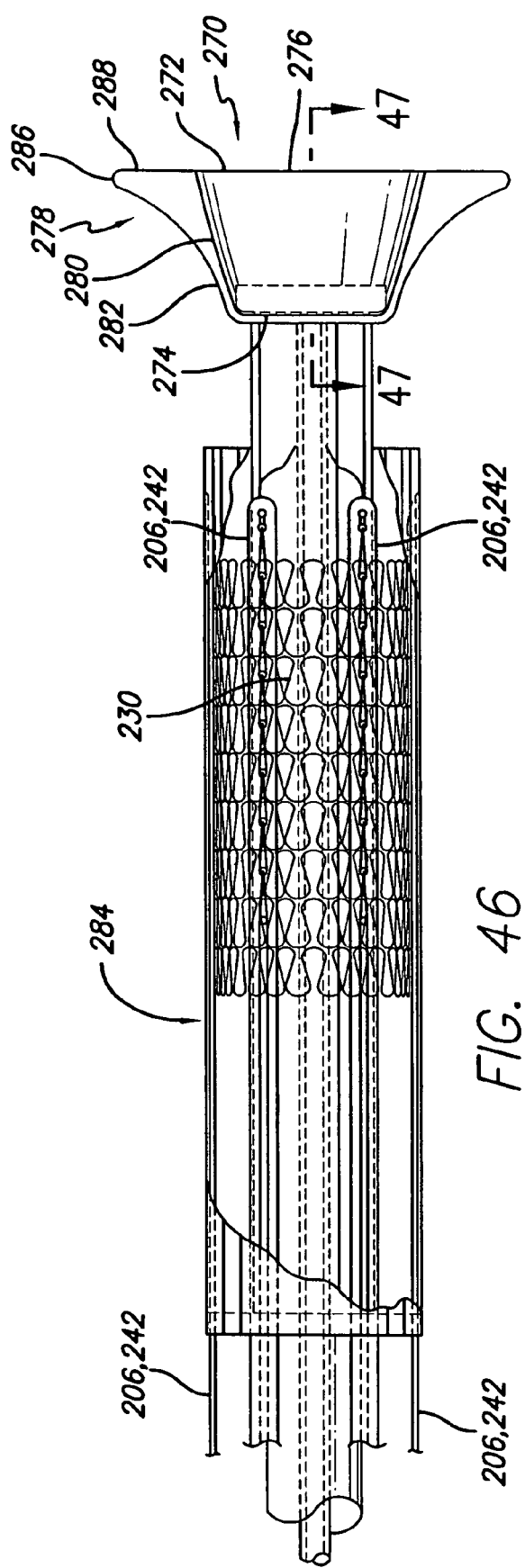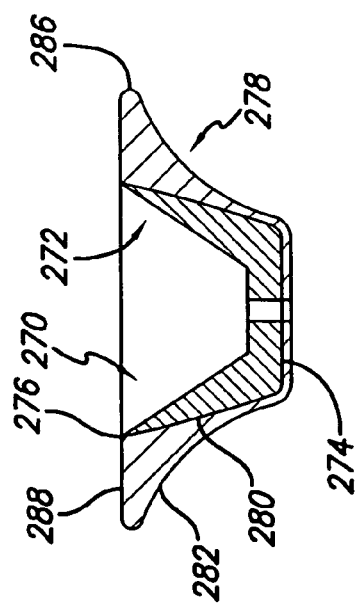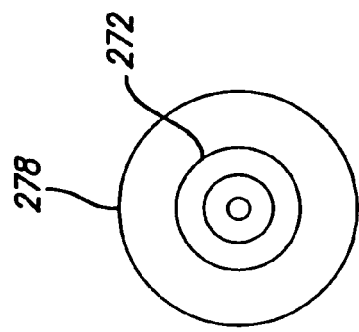

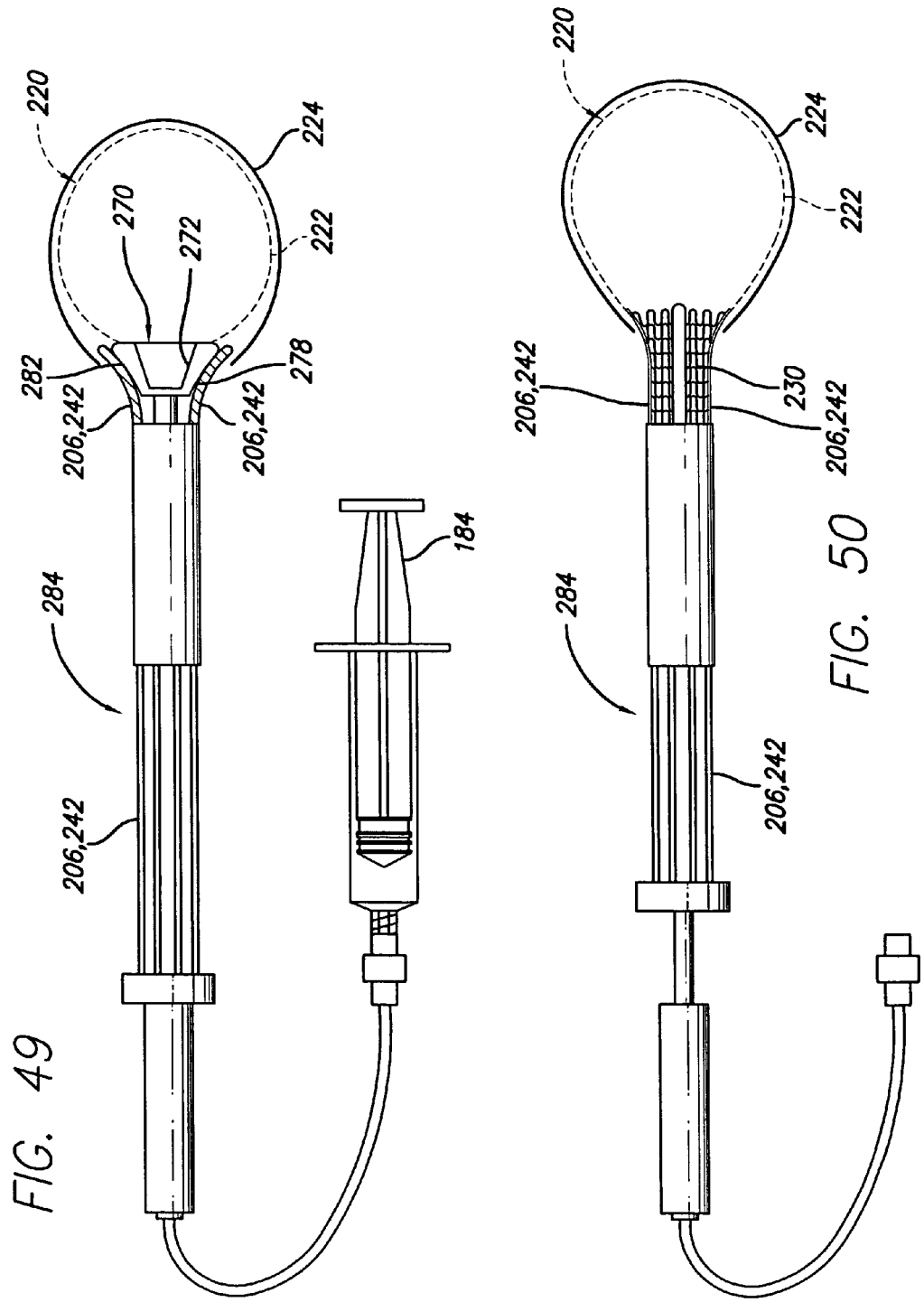

CARDIAC HARNESS DELIVERY DEVICE AND METHOD OF USE

CROSS-REFERENCES TO RELATED APPLICATIONS

The present application is a continuation-in-part of U.S. Ser. No. 10/715,150 filed Nov. 17, 2003 which is related to, and claims priority from, U.S. Provisional Patent Application No. 60/427,079, filed Nov. 15, 2002, the entirety of each of which is hereby incorporated by reference.

FIELD OF THE INVENTION

The present invention relates generally to a device and method for delivering a cardiac harness onto the heart of a patient.

BACKGROUND OF THE INVENTION

Congestive heart failure ("CHF") is characterized by the failure of the heart to pump blood at sufficient flow rates to meet the metabolic demand of tissues, especially the demand for oxygen. It has been determined that a passive wrap, or cardiac harness, may increase the efficiency of a heart affected by congestive heart disease. While advances have been made in cardiac harness technology, a satisfactory device and method for delivering and positioning the cardiac harness onto a patient's heart has yet to be provided.

In one method, access to a patient's heart is achieved through an open chest procedure, wherein the sternum is split and separated to allow access to the heart. The cardiac harness is then positioned over the heart by manual manipulation. Such an open chest procedure is highly traumatic to the patient and, thus, remains a relatively undesirable option for cardiac harness delivery. Present cardiac harness delivery devices do not both adequately retain the cardiac harness onto the delivery device and permit the harness to be easily released from the delivery device. For example, one delivery device utilizes sutures positioned around a circumference of the cardiac harness to secure it to the delivery device. Such arrangements render the cardiac harness difficult to release from the delivery device, especially on the rearward side of the heart. This is because the sutures have to be severed in order to release the cardiac harness from the delivery device. Such an arrangement would not be well suited for a minimally invasive procedure because an additional instrument would have to be introduced to sever the sutures. Furthermore, attaching the cardiac harness to the delivery device only along a circumference tends to apply a localized load to the cardiac harness, which may cause damage to the device.

SUMMARY OF THE INVENTION

Experience has shown that patients having congestive heart failure have hearts that are very globular or spherical, the pericardium may be very tight to the epicardium, and there may be very little space between the heart and ribs due to the size of the enlarged heart. In these instances, it is difficult to deploy a cardiac harness minimally invasively since the initial turn or bend to push the harness onto the heart can be anywhere from 10° to 90°. For example, a cardiac harness that is delivered using push arms to push the cardiac harness out of a delivery device may have to flex and bend radially outwardly at up to 90° in order to begin pushing the cardiac harness onto the heart. Thus, the present invention addresses the need to deliver a cardiac harness where the heart is somewhat spherical and the initial bend is quite severe in placing the harness on the heart. Accordingly, a delivery device is configured, in one orientation, to support the cardiac harness in a compacted configuration to permit minimally invasive delivery of the cardiac harness through a relatively small incision in the patient and deliver the harness onto a more spherical shaped heart.

In one embodiment, a cardiac harness is delivered onto an enlarged heart where the initial radius of pushing the cardiac harness onto the heart is high. In other words, the cardiac harness is pushed out of a delivery device and immediately must turn outwardly anywhere from approximately 10° up to approximately 90°. In this embodiment, the cardiac harness is attached to push arms that have a longitudinal lumen extending for at least a portion of the push arms. A stylet can be shaped or bent according to the particular need for each patient and inserted into the longitudinal lumen of the push rods. Each stylet is bent radially outwardly and will bias the push rods radially outwardly in order to assist the push rods in making the initial turn around the apex of the heart. The stylet also can have a second bend or turn in order to assist the push rod to follow the contour of the geometry of the heart from the initial steep bend to a more gradual curving as the push rod travels along the heart.

In one embodiment, the delivery device includes a plurality of push rods inserted into sheaths on the cardiac harness. With such an arrangement, the applied load is spread along the length of the cardiac harness, thereby reducing the possibility of damaging the harness during delivery, especially when advancing over the apex region of the heart which may be a very tight radius to negotiate. After the harness is mounted on the heart, the push rods are withdrawn from their respective sheaths on the cardiac harness.

In another embodiment, the cardiac harness includes one or more electrodes associated therewith for the purpose of providing a defibrillating shock, or for providing pacing/sensing therapy to a patient. A cardiac delivery device allows release of the cardiac harness and associated electrodes from a remote location. The delivery device is configured to support the cardiac harness in a compacted configuration to permit minimally invasive delivery of the cardiac harness through a relatively small incision in the patient. The delivery device includes push rods inserted into sheaths formed integrally with electrodes mounted on the cardiac harness. With such an arrangement, the applied load during delivery is spread along the length of the electrodes and the cardiac harness, thereby reducing the possibility of damaging the harness or the electrodes during delivery and mounting of the cardiac harness on the heart. Again, this embodiment permits the push rods to bend up to 90° to negotiate the initial very severe bend in the apex region of the heart.

In a further embodiment, the present invention involves an assembly for delivering a cardiac harness including an elongate body having a proximal portion and a distal portion. The body has a cavity sized to contain the harness in a compacted configuration. A plurality of elongate push rods are longitudinally movable with respect to the body. The cardiac harness is releasably connected to each of the push rods such that advancement of the push rods in a distal direction moves the harness from the compacted configuration in the cavity to an expanded configuration outside the cavity.

In another embodiment, an assembly for delivering a cardiac harness includes an elongate body having a proximal portion and a distal portion. The elongate body has a cavity sized to contain the cardiac harness in a compacted configuration. A plurality of elongate push rods are longitudinally movable with respect to the elongate body to deliver the cardiac harness onto the heart. The distal end of the push rods are configured to have a predetermined bend angle relative to the longitudinal axis of the push rod, the bend angle being radially outwardly and predisposed to flex more radially outwardly than other portions of the push rod. The distal end of the push rod is radially outwardly more flexible than other portions of the push rod in order for the distal end to make the initial bend near the apex of the heart as the cardiac harness is pushed onto the heart by advancement of the elongate push rods. Further, a distal region of the push rods have varying flexibility in order for the distal region to make an S turn while the push rods are advanced distally to mount the cardiac harness onto the heart.

In another embodiment, an elongate body has a proximal portion and a distal portion for delivering a cardiac harness to the heart. A plurality of elongate push rods are longitudinally movable with respect to the elongate body and are removably attached to the cardiac harness in order to push the cardiac harness onto the heart. In this embodiment, a suction cup at the distal end of the elongate body assists the distal ends of the push rods to flare radially outwardly during initial contact with the apex region of the heart as the elongate push rods are advanced onto the heart to deliver the cardiac harness. The suction preferably has first and second diameters. The first diameter engages the apex of the heart, and the second diameter acts as a ramp to flare the push rods radially outwardly to help make the turn around the apex region of the heart as the cardiac harness is advanced out of the delivery device.

In a further embodiment, an elongate body has a proximal portion and a distal portion, and a cavity size to contain a cardiac harness in a compacted configuration. A plurality of elongate push rods are longitudinally movable with respect to the elongate body to deliver the elongate harness onto the heart. The elongate push rods have a proximal end having a predetermined stiffness in all directions. The push rods have a central section having a stiffness that is different than that in the proximal region. Further, the elongate push rods have varying stiffness in the distal region so that the push rods are stiff laterally but more flexible in a radial direction, however, not so flexible so that the push rods will buckle when flexed.

In another embodiment, the present invention involves an assembly for delivering a cardiac harness including an elongate body having a proximal portion and a distal portion. The body has a cavity sized to contain the harness in a compacted configuration. A plurality of elongate push rods are longitudinally movable with respect to the elongate body and to deliver and mount the cardiac harness onto the heart. The elongate push rods have a distal end having a predetermined bend to form an atraumatic tip so that the distal end of the push rods do not dig into or otherwise harm the surface of the heart. During aging and storage, the curvature in the distal ends in the elongate push rods can flatten, thereby reducing the effectiveness of the predetermined bend. In this embodiment, the distal ends of the push rods can be bent by the doctor in order to return the predetermined bend in the distal end of the push rod. Further, during storage, a donut-shaped device or tip spreader is formed around the distal ends of the push rods in order to maintain the predetermined bend and to eliminate the possibility of the distal ends flattening during storage.

BRIEF DESCRIPTION OF THE DRAWINGS

These and other features, aspects and advantages of the present invention are described with reference to drawings of a preferred embodiment, which are intended to illustrate, but not to limit, the present invention.

FIG. 6 is an enlarged, side view of the control assembly of the delivery device of FIG. 1 indicated by line 6-6 of FIG. 3. The illustrated control assembly includes a body portion, a cover and a release member.

FIG. 7A illustrates a plurality of channels defined by the body portion of the control assembly. The channels are configured to receive portions of the line associated with each push rod.

FIG. 8 is a cross-sectional view of the control assembly of FIGS. 6 and 7, taken along line 8-8 of FIG. 7A.

FIG. 9 is a cross-sectional view of the control assembly of FIGS. 6 and 7, taken along line 9-9 of FIG. 7A.

FIG. 13 is a side elevational view of an introducer sleeve portion of an introducer assembly for facilitating introduction of the delivery device of FIGS. 1-12 through the pericardium surrounding the heart of a patient.

FIG. 14 is a side elevational view of the introducer assembly, illustrated in an unassembled condition and including the introducer sleeve and a dilator sleeve.

FIG. 15 is a side elevational view of the introducer assembly in an assembled condition, with the dilator sleeve disposed within the introducer sleeve.

FIG. 16 is a perspective view of a heart having a small incision in the pericardium to permit the delivery device to access the heart.

FIG. 17 is a perspective view of the heart of FIG. 16 with the introducer sleeve of the introducer assembly of FIG. 14 positioned within the incision in the pericardium.

FIG. 21 is a side elevational view of the delivery device of FIG. 19 with the cardiac harness in a fully advanced position and the releasing member being actuated to release the cardiac harness from the delivery device.

FIG. 22 is a side elevational view of the delivery device of FIG. 19 with the cardiac harness being completely released and the plurality of push rods being retracted.

FIG. 29 is an elevational view depicting a stylet for forming a bend in a push rod.

FIG. 30 is an elevational view depicting a stylet having a bend in the distal end therein.

FIG. 31 is an elevational view depicting a push rod having a longitudinal lumen for slidably receiving a stylet.

FIG. 32 is a partial transverse cross-sectional view taken along lines 32-32 depicting a push rod having a longitudinal lumen for receiving a stylet.

FIG. 46 is a partial side elevational view of a delivery device with a suction cup member having a flared portion for assisting the push rods in bending upon delivery of the cardiac harness.

FIG. 47 is a cross-sectional view taken along lines 47-47 depicting the suction cup and the flared portion.

FIG. 48 is a side view of the suction cup depicted in FIG. 46.

FIG. 49 is a side elevational view depicting the delivery device advancing the push rods past the flared portion of the suction cup.

FIG. 50 is a side elevational view of the delivery device advancing the push rods past the flared portion of the suction cup so that the push rods slide along the epicardial surface of the heart.

DETAILED DESCRIPTION OF THE PREFERRED EMBODIMENTS

Figure 1:
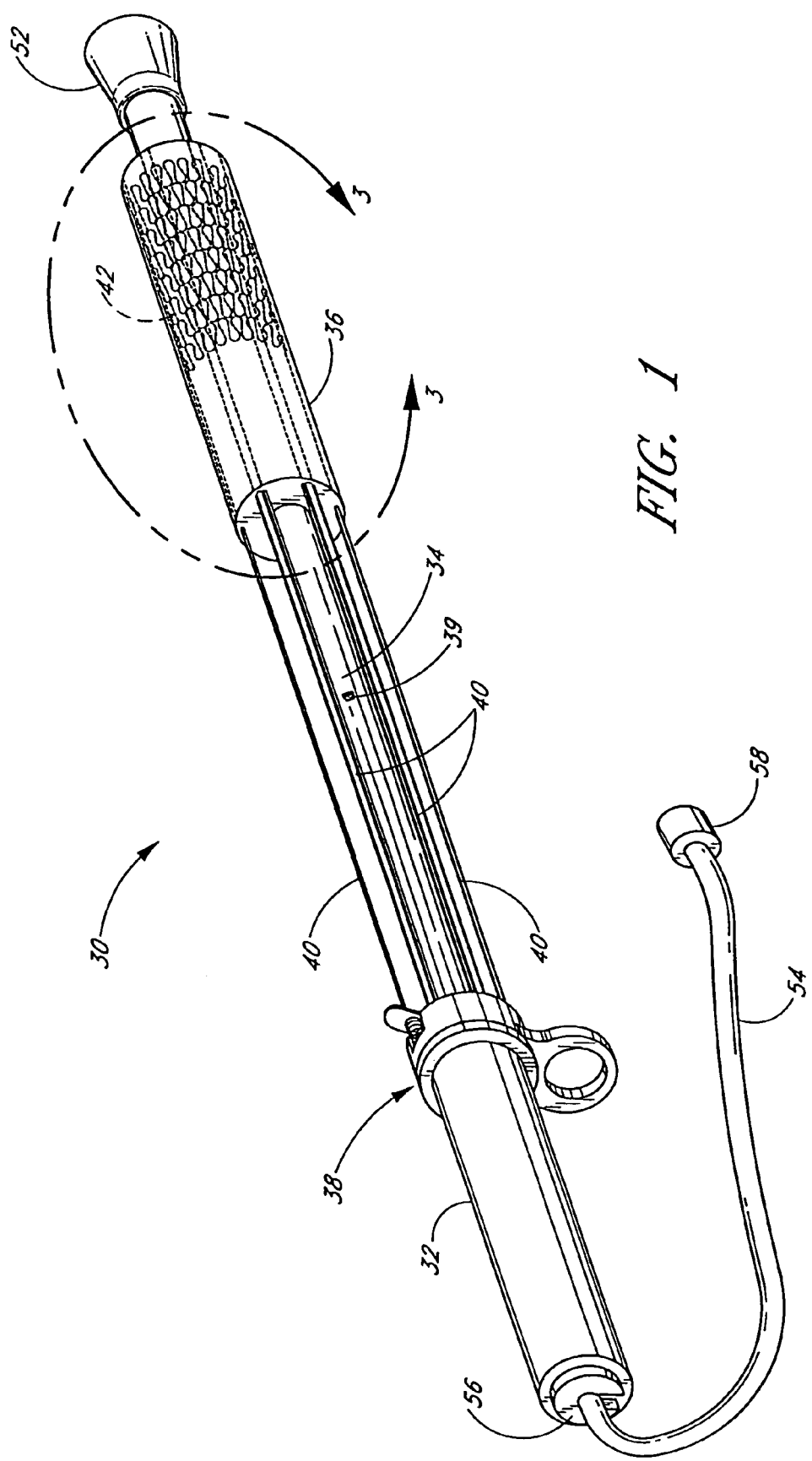
FIG. 1 is a perspective view of a cardiac harness delivery device constructed in accordance with certain features, aspects and advantages of the present invention. The illustrated delivery device comprises a body portion, including an elongate shaft and a housing, and a movable portion, including a control assembly and a plurality of elongate push rods. A cardiac harness is carried by distal end portions of the plurality of push rods.

FIGS. 1-11 illustrate a preferred embodiment of a cardiac harness delivery device, which is generally referred to by the reference numeral 30. In a preferred embodiment, the delivery device 30 is configured to releasably support a cardiac reinforcement device (CRD), such as a cardiac harness, and assist in the advancement of the cardiac harness over the heart of a patient. Once the cardiac harness is positioned on the heart, the delivery device 30 preferably is configured to release the harness and be retractable without causing undesired shifting of the cardiac harness relative to the heart.

In the illustrated arrangement, the delivery device 30 permits delivery of a cardiac harness in a minimally invasive manner. That is, preferably the device 30 permits accurate delivery, positioning, and release of the cardiac harness through a relatively small incision in a patient. However, the preferred, or alternative, embodiments of the delivery device 30 may also be used to deliver a cardiac harness in an open chest, or other minimally invasive procedure. Further, an embodiment preferably is configured to enable indirect visualization of at least portions of the device 30 during surgery. For example, portions of the device may be radio-paque so as to be visualized and guided by fluoroscopy or other methods.

With specific reference to FIG. 1, the illustrated delivery device 30 generally includes a body portion comprised of a handle 32 affixed to the proximal end of a hollow, elongate shaft 34. Preferably, a housing 36 is affixed to a distal end of the elongate shaft 34. The illustrated delivery device 30 also includes a movable portion comprised of a control assembly 38 and a plurality of elongate push rods 40. The control assembly 38 and, thus, the push rods 40, are axially slidable along the shaft 34.

Figure 2:
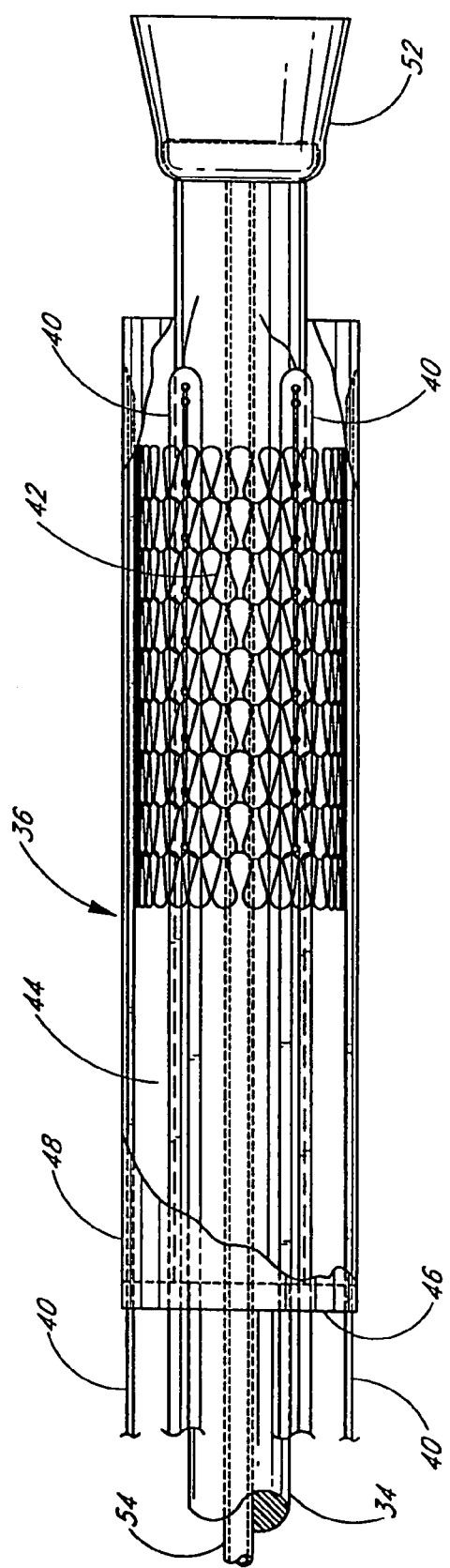
FIG. 2 is an enlarged, partial cutaway view of a distal portion of the delivery device of FIG. 1 showing the cardiac harness in a compacted configuration within a cavity defined by the housing.

Preferably, the plurality of push rods 40 extend in a distal direction from the control assembly 38 and pass through the housing 36. With reference also to FIG. 2, a cardiac harness 42 is releasably supported on the distal end portions of the elongate push rods 40 in a compacted configuration within the housing 36. Preferably, the cardiac harness 42 comprises an elastic sleeve configured to fit around the heart and to exert a compressive force on the heart. In the illustrated embodiment, the harness 42 comprises several interconnected rows of undulating elastic members. Preferred cardiac harnesses are described in greater detail in U.S. patent application Ser. No. 09/634,043, filed Aug. 8, 2000 now U.S. Pat. No. 6,702,732; U.S. application Ser. No. 10/242,016, filed Sep. 10, 2002 now U.S. Pat. No. 6,723,041; U.S. application Ser. No. 10/287,723, filed Oct. 31, 2002; and U.S. application Ser. No. 10/656,722, filed Sep. 5, 2003, the entirety of each of which are incorporated by reference herein. It is to be understood that aspects of the delivery device 30 discussed herein can be used in connection with several other types of cardiac harnesses.

The term "cardiac harness" as used herein is a broad term that refers to a device fit onto a patient's heart to apply a compressive force on the heart during at least a portion of the cardiac cycle. A device that is intended to be fit onto and reinforce a heart and which may be referred to in the art as a "girdle," "sock," "jacket," "CRD," or the like is included within the meaning of "cardiac harness."

Figure 3:
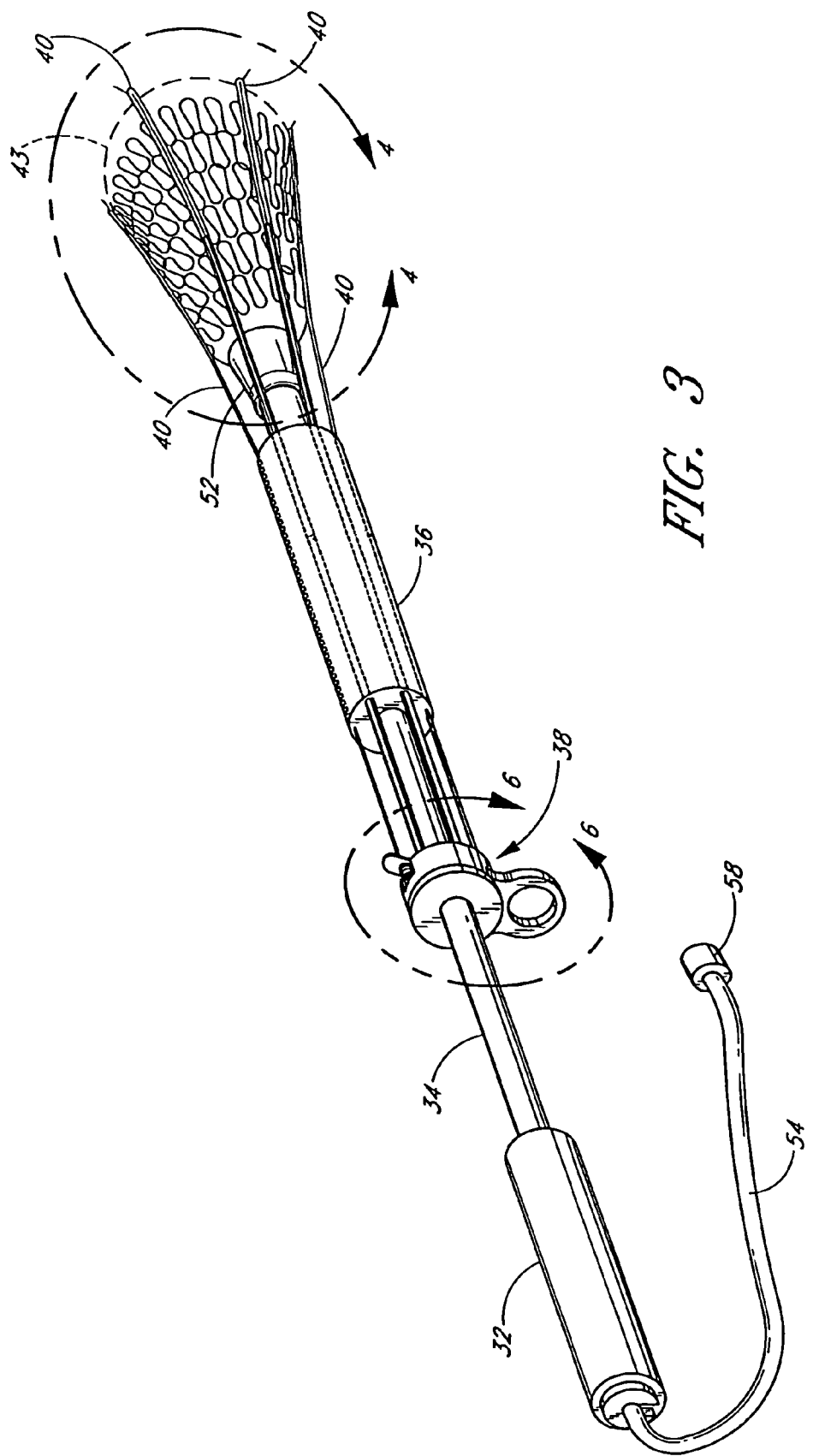
FIG. 3 is a perspective view of the delivery device of FIG. 1 with the movable portion in an advanced position relative to the body portion.
Figure 4:
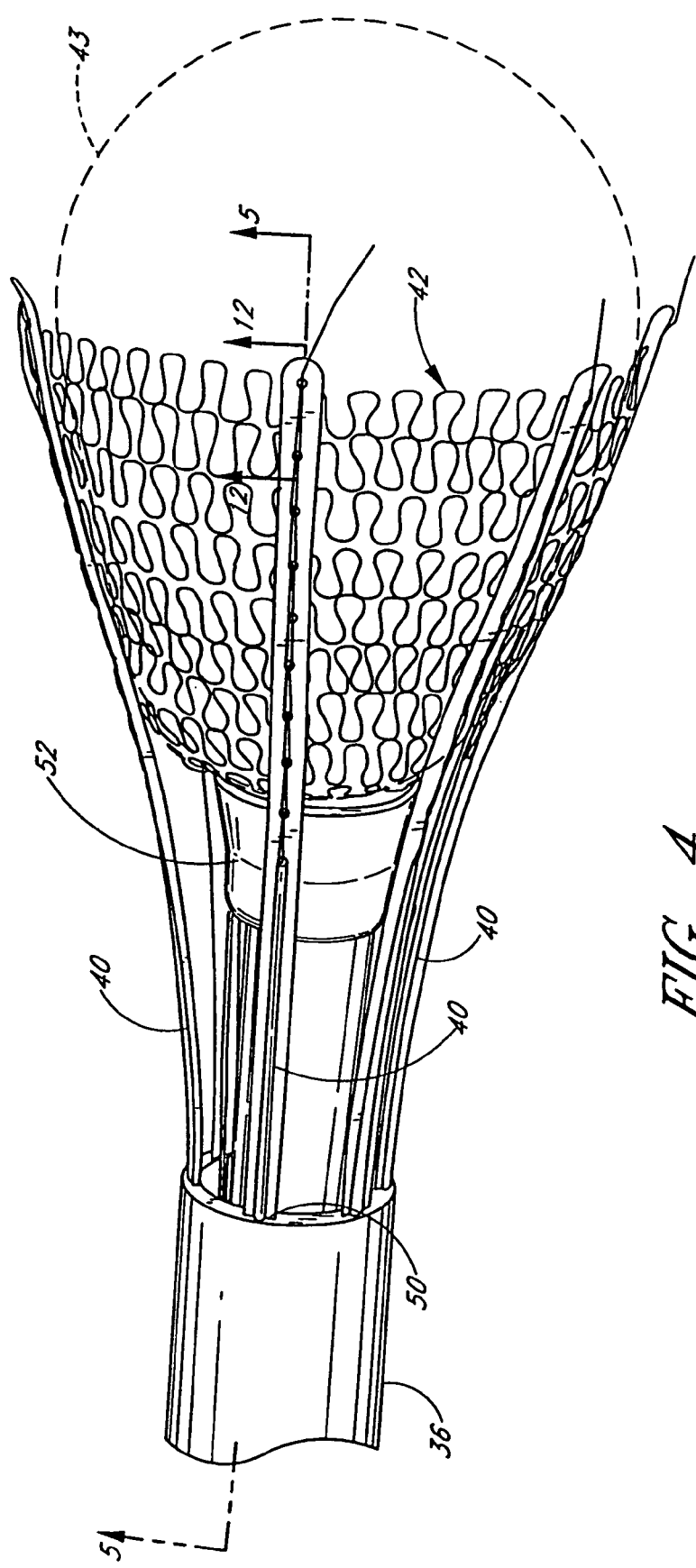
FIG. 4 is an enlarged view of a distal portion of the delivery device of FIG. 1 indicated by line 4-4 of FIG. 3.

The control assembly 38 and plurality of push rods 40 are movable axially with respect to the shaft 34 from the retracted position illustrated in FIG. 1 to an advanced, or deployed position, as illustrated in FIGS. 3 and 4. Thus, the delivery device 30 is configured to deploy the cardiac harness 42 from a compacted configuration within the housing 36 to an expanded position outside of the housing 36 thereby delivering the cardiac harness 42 onto a heart 43 (FIGS. 3 and 4), as is described in greater detail below.

The handle 32 is fixed to the shaft 34 in the illustrated embodiment. However, it is to be understood that in other arrangements the handle 32 may be movable relative to the shaft 34 along with the control assembly 38. Additionally, another embodiment may not employ a handle 32. Further, with reference to FIG. 1, a stop 39 preferably is provided on the shaft 34. The stop 39 comprises a raised portion that engages the control assembly 38 so that the assembly 38 cannot move distally over the shaft 34 beyond the stop 39. As such, the harness 42 is not advanced too far over the heart 43.

With reference again to FIG. 2, the housing 36 preferably is a relatively thin-walled, tubular member. Desirably, the housing 36 is supported substantially concentric with the shaft 34 to define an interior cavity 44 between an inner surface of the housing 36 and an outer surface of the shaft 34. Preferably, the cavity 44 is sized and shaped to contain the cardiac harness 42 in a compacted configuration therein.

As indicated above, preferably the device 30 is configured to deliver the cardiac harness 42 in a minimally invasive procedure. Accordingly, a preferred housing 36 has a nominal outer diameter of less than about 2 inches and, more preferably, less than about 1.5 inches. However, in additional, non-minimally invasive embodiments, the housing 36, if provided, may be larger than the values given above. In such arrangements, the harness 42 may be supported by the device 30 in a configuration substantially similar to the configuration of the harness 42 when positioned on a heart. That is, the cardiac harness does not have to be supported in a "compacted" configuration by the device, but may be supported in a configuration closer to its relaxed size and shape.

In the embodiment shown in FIGS. 1-3, the housing 36 is generally cylindrical. It is to be understood that, in another preferred embodiment, the housing is elliptical. As such, the housing may have a major axis and minor axis. This configuration may be especially beneficial for advancing the housing through body passages having relatively narrow clearance, such as advancing the housing between the ribs.

With continued reference to FIG. 2, a base portion 46 of the housing 36 preferably defines a closed end of the cavity 44 and supports the housing 36 relative to the shaft 34. The base end 46 may be secured to the shaft 34 by mechanical fasteners, adhesives or other suitable methods apparent to one of skill in the art. In one embodiment, the base end 46 is rotatable relative to the shaft 34. Preferably, the distal end of the housing is open to define an open, distal end of the cavity 44 to permit the cardiac harness 42 to be advanced from the cavity 44.

Preferably, an outer wall 48 of the housing 36 defines a plurality of channels 50 (FIG. 4) extending axially throughout the length of the housing 36. Each of the channels 50 preferably is sized and shaped to slidably receive one of the plurality of push rods 40. Thus, preferably, the number of channels 50 is equal to the number of push rods 40. Further, each channel 50 preferably opens into a cavity 44 along at least a portion of the length of the channel 50.

In the illustrated embodiment, six push rods 40 and channels 50 are provided and are substantially equally spaced around the circumference of the housing 36. In an additional arrangement, however, the channels 50 may be omitted and the push rods 40 may simply be restrained from moving radially outwardly by the sidewall 48 of the housing 36. Other suitable arrangements to guide the push rods 40 and house the cardiac harness 42 may also be used.

With continued reference to FIGS. 1-4, the delivery device 30 preferably includes a positioning arrangement configured to hold the delivery device 30 in a desired position relative to the heart 43. In the illustrated arrangement, the positioning arrangement comprises a suction cup member 52 supported on a distal end of the shaft 34. A tube 54 extends through the shaft 34 and is connected to the suction cup member 52. A distal end of the tube 54 opens into an interior space defined by the suction cup member 52. The proximal end of the tube 54 includes a connector 58 that allows connection of the tube 54 to a pump member such as a syringe or other source of vacuum. Accordingly, once the delivery device is properly positioned, air may be withdrawn from within the tube 54 to create a vacuum condition within the interior space of the suction cup member 52, thereby permitting the suction cup member 52 to securely hold the heart of a patient.

A clip 56 secures the tube 54 relative to the handle 32 to prevent the proximal end of the tube 54 from passing through the shaft 34. Thus, the clip 56 also operates to secure the suction cup member 52 to the delivery device 30. In a preferred embodiment, the tube 54 and suction cup member 52 are not rigidly affixed to the shaft 34 so that the shaft 34 may be moved relative to the tube 54 and suction cup 52. In another embodiment, the shaft 34 and a proximal end of the suction cup 52 are threaded so that the suction cup may be threaded onto the shaft. In still other embodiments, other structure may be used to releasably connect the suction cup to the shaft.

Figure 5:
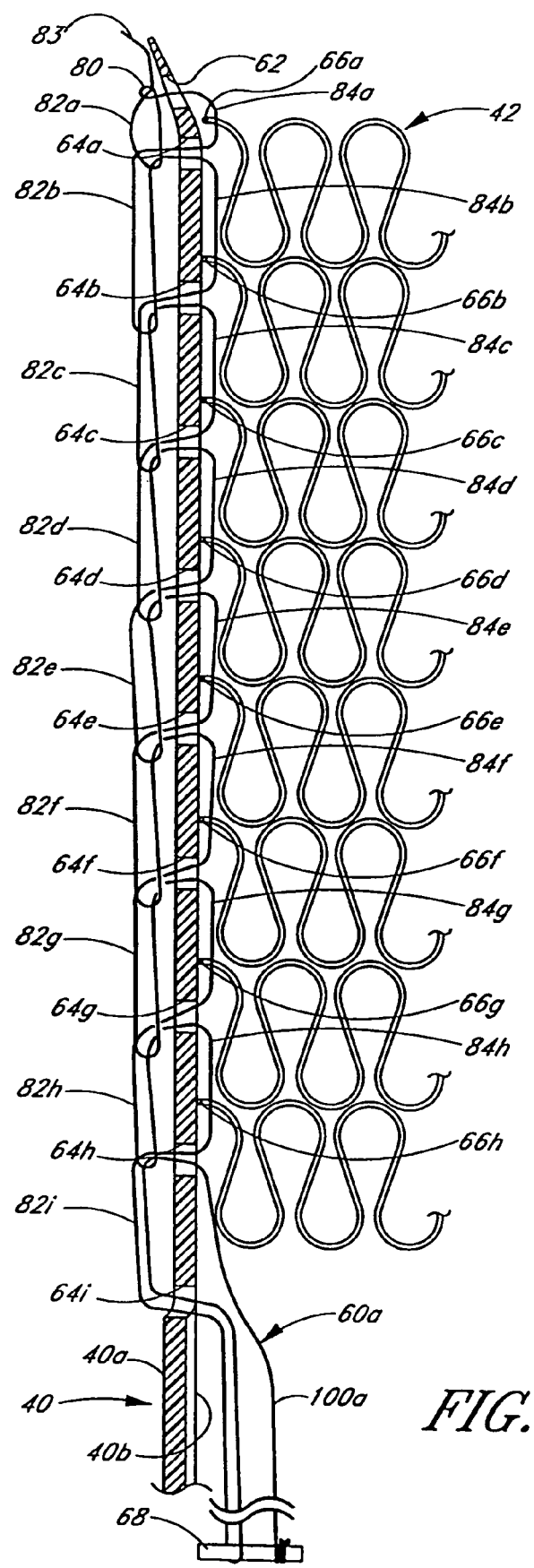
FIG. 5 is a cross-sectional view of one of the plurality of push rods taken along line 5-5 of FIG. 4 depicting a line, forming a releasable stitch, to secure the cardiac harness to the push rod.

With reference next to FIG. 5, preferably the cardiac harness 42 is secured to a distal end portion of each of the plurality of push rods 40 by a line, generally referred to by the reference numeral 60, that is configured into a releasable stitch. As shown in FIG. 5, a line 60a is associated with one of the plurality of push rods 40 and is arranged into a releasable stitch configured to secure the cardiac harness 42 to the push rod 40. Although not individually illustrated, preferably, each of a plurality of such lines 60b-f secure the cardiac harness 42 to a corresponding one of the remainder of push rods 40 in a manner similar to line 60a, which is illustrated in FIG. 5. Desirably, the line 60a is arranged into a series of interconnected loops that are releasable by actuation of the control assembly 38 in a manner described in greater detail below. Release of the interconnected loops, in turn, releases the cardiac harness 42 from the push rod 40.

The illustrated push rod 40 includes a plurality of throughholes, or openings 62, 64a-i, extending from an outward facing surface 40a of the push rod 40 to an inward facing surface 40b of the push rod 40. In the illustrated embodiment, ten openings 62, 64a-i are provided, however, other numbers of openings may be provided to permit other types and sizes of cardiac harnesses to be secured to the delivery device 30. Desirably, the openings 64a-i are equally spaced from one another, with the space between the distal most opening 62 and the opening 64a being less than the equal spacing between openings 64a-i. Preferably, the space between the openings 62 and 64a is sufficient to accommodate the diameter of an individual wire, which forms an uppermost row 66a of the illustrated cardiac harness 42. In addition, preferably the remainder of the openings 64a-i are spaced from one another a distance substantially equal to a height of one row 66b-h of the cardiac harness. Such an arrangement permits positioning of the wire of a single row 66b-h of the cardiac harness 42 between each pair of openings 64a-i.

Although the line 60a is shown as being spaced from both the outward facing surface 40a and inward facing surface 40b in FIG. 5, preferably, the line 60a is pulled tight after passing through the openings 62, 64a-i to secure the cardiac harness 42 directly against the inward facing surface 40b of the push rod 40. The spaced orientation of the line 60a depicted in FIG. 5 is merely for the purpose of clearly illustrating the configuration of the releasable stitch.

In a preferred embodiment of the releasable stitch, a first end of the line 60a is arranged into a slip knot 80, which defines a first loop 82a positioned on the outward facing surface 40a side of the push rod 40. The slip knot 80 desirably is created near one end of the line 60a such that, along with the first loop 82a, a short end portion 83 of the line 60a is created. The remainder of the line 60a is arranged into interconnecting loops to create the releasable stitch, as is described below.

The line 60a passes through the distal most opening 62 to the inward facing surface 40b side of the push rod 40. Preferably, the line 60a then passes around the wire of the uppermost row 66a of the cardiac harness 42 before passing through the opening 64a back to the outward facing surface 40a side of the push rod 40. Thus, between the openings 62 and 64a, the line 60a creates a securing portion 84a that holds the row 66a of the cardiac harness 42 against the inward facing surface 40b of the push rod 40.

Once on the outward facing surface 40a side of the push rod 40, the line 60a passes through the first loop 82a and is arranged to form a second loop 82b. Preferably, the second loop 82b is large enough so that it extends toward the proximal end of the push rod 40 a sufficient distance to pass beyond the next adjacent opening 64b. The line 60a then passes back through the first loop 82a and the opening 64a to the inward facing surface 40b side of the push rod 40. The line 60a creates another securing portion 84b, which secures a wire of a second row 66b of the cardiac harness 42 to the push rod 40.

Preferably, in a similar manner, interconnected loops 82c through 82h are formed. Each of the loops 82c-h are positioned on the outward facing surface 40a side of the push rod 40 and correspond with respective securing portions 84c-84h, which secure a respective wire of each row 66c-h of the cardiac harness 42 against an inward facing surface 40b of the push rod 40. Although, preferably, each securing portion 84a-h of the line 60a secures a single row 66a-h of the cardiac harness 42 to the push rod 40, in other configurations more or less than one row of the harness 42 may be secured by a single securing portion 84a-h. Further, although in the illustrated embodiment, one hole 64 of the push rod 40 generally corresponds to one row 66 of the associated harness 42, it is to be understood that, in other embodiments, one row 66 may correspond with more or less than one hole 64 and more or less than one securing portion 84.

In accordance with this arrangement, the cardiac harness 42 is secured to each push rod 40 at at least two longitudinally-spaced locations. In the illustrated embodiment, the harness 42 is secured to each push rod 40 at eight longitudinally-spaced locations, or each of the eight rows 66a-h of the cardiac harness 42 is secured to each of the push rods 40.

Preferably, a proximal-most, or retaining, loop 86a is arranged to inhibit the remaining loops 82a-h from unraveling prematurely. In a preferred arrangement, the retaining loop 86a passes through the next distal loop 82h in a manner similar to the arrangement of loops 82a-h as described above. The retaining loop 86a, however, has a sufficient length to extend in a proximal direction along the push rod 40 to the control assembly 38. Preferably, the loop 86a passes through the lowermost opening 64i to the inward facing surface 40b side of the push rod 40 and is extended along the push rod 40 in a proximal direction. Within the control assembly 38, the loop 86a is looped around a retaining rod 68 (shown schematically in FIG. 5).

The remaining end portion 100a of the line 60a, after forming the retaining loop 86a, is passed through the loop 82h and the opening 64h to the inward facing surface 40b side of the push rod 40. The end portion 100a of the line 60a also extends in a proximal direction along the push rod 40 and is tied off on the retaining rod 68. Thus, in the illustrated arrangement, unravelment of the releasable stitch is prevented by the combination of the retaining loop 86a being looped around the retaining rod 68, and the end portion 100 of the line 60a being tied onto, the retaining rod 68. Although shown tied onto the retaining rod 68, desirably, the end portion 100 is tied off onto a releasable portion of the control assembly 38, rather than the retaining rod 68 itself, as will be described in greater detail below.

In an alternative arrangement, the retaining loop 86a may not be looped around the retaining rod 68, but may be inhibited from unraveling by an alternatively suitable arrangement. For example, it is contemplated that the retaining loop 86a may be formed approximately the same size as the remainder of the interconnected loops 82a-h and may be tucked between the adjacent loop 82h and the outward facing surface 40a of the push rod 40. Thus, the retaining loop 86a is inhibited from unraveling by a frictional force of the adjacent loop 82h holding the retaining loop 86a against the outward facing surface 40a. When a sufficient pulling force is applied to the end portion 100, the retaining loop 86a overcomes the frictional force of the loop 82h and the outward facing surface 40a and is drawn through the opening 64h, thus permitting unraveling of the releasable stitch.

With reference next to FIGS. 6-9, a preferred embodiment of the control assembly 38 is described in greater detail. As indicated above, the control assembly 38 is movable axially relative to the shaft 34 of the delivery device 30. Preferably, the control assembly 38 includes a position-retaining arrangement, such as a friction brake assembly 102, for example. The friction brake assembly 102 is configured to permit the control assembly 38 to be selectively retained in a desired position relative to the shaft 34. Preferably, the friction brake assembly 102 is configured to be easily actuatable, along with movement of the control assembly 38, by one hand of a user of the device 30.

With particular reference to FIGS. 6 and 9, the illustrated friction brake assembly 102 includes a brake element 104 and a biasing member, such as a spring 106. The brake element 104 includes an annular central portion 104a surrounding the shaft 34. Opposing end portions 104b, 104c extend in an outward direction from the central portion 104a substantially opposite from one another. The first end portion 104b is retained within a channel 108 of the control assembly 38, preferably by a pin 110. The pin 110 is supported within cavities (not shown) of the control assembly 38 on each side of the channel 108. Thus, the brake element 104 is pivotable generally about an outer surface of the pin 110.

The spring 106 is retained within a cavity 111 and is arranged to bias the second end 104c of the brake element 104 away from the control assembly 38. Preferably, the spring 106 biases the brake element 104 such that an inner diameter-defining surface of the central portion 104a is in frictional contact with the shaft 34 so as to secure the control assembly 38 in a desired position relative to the shaft 34. The brake element 104 may be pivoted toward the control assembly 38 by pushing the end 104c toward the control assembly 38 to disengage the brake element 104 from the shaft 34 and permit relative movement between the control assembly 38 and the shaft 34. In another embodiment, two such brake elements 104 are provided. However, each brake element is oriented to pivot in an opposite direction. As such, one brake element better prevents distal movement of the assembly relative to the shaft, and the other brake element better prevents proximal movement of the assembly relative to the shaft.

With particular reference to FIGS. 6 and 8, the control assembly 38 preferably includes a substantially cylindrical body portion 112. A plurality of passages, generally referred to by the reference numeral 114, extend axially through the body portion 112 of the control assembly 38. In the illustrated embodiment, the passages 114 are substantially cylindrical in shape and are equally distributed in a circular arrangement coaxial with the shaft 34. Preferably, the passages 114 are generally aligned with corresponding channels 50 formed in the housing 36.

A cover 116 is fixed to a proximal end of the body portion 112. The cover 116 closes a proximal end of the passages 114 and the cavity 111. A plurality of fasteners, such as screws 118, engage corresponding threaded apertures 120 (FIG. 7A) of the body portion 112 to secure the cover 116 to the body portion 112.

Figure 7A:
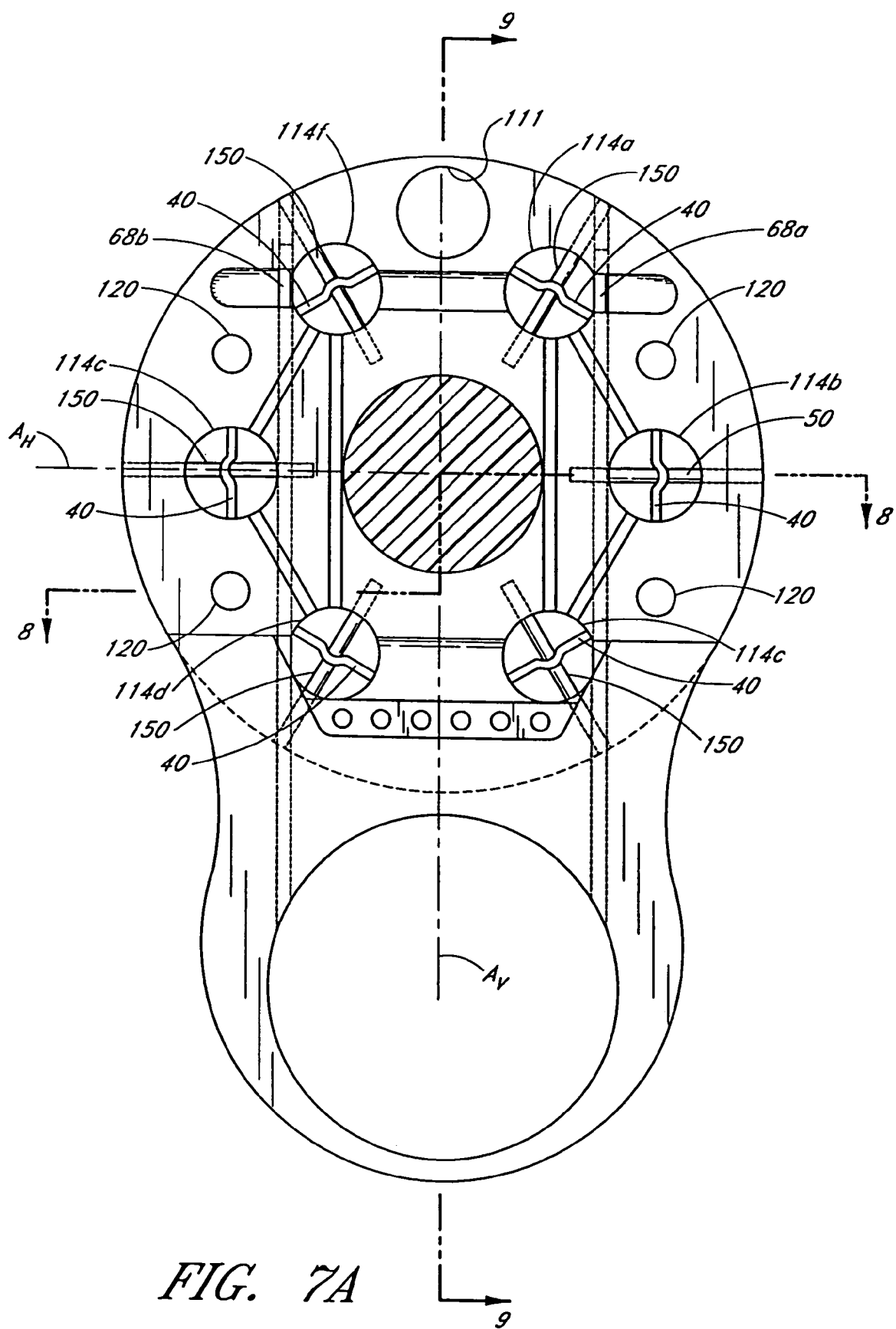
FIG. 7A is a plan view of the body portion of the control assembly of FIG. 6, taken along line 7-7 of FIG. 6.
Figure 7B:
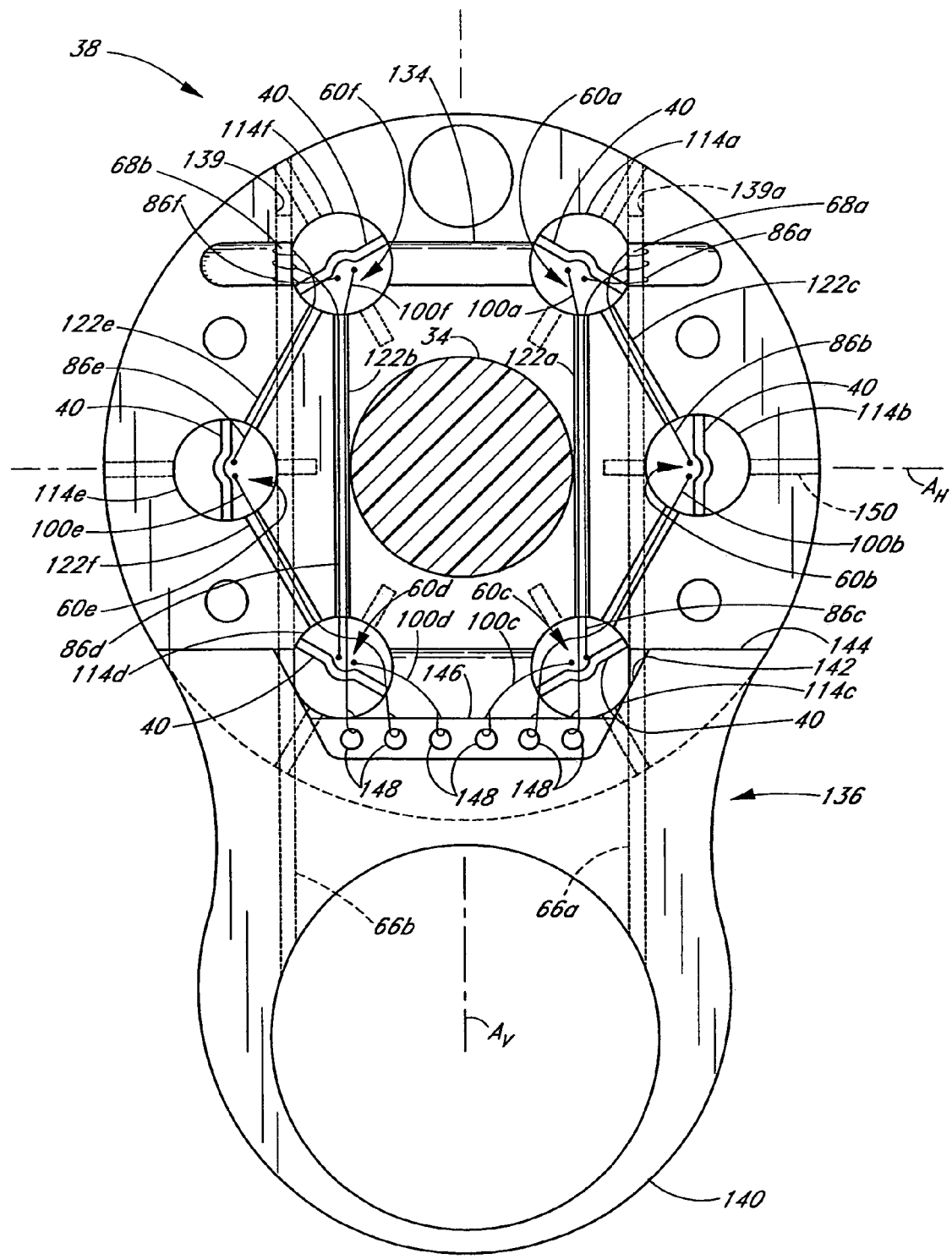
FIG. 7B is an enlarged view of the body portion of the control assembly of FIG. 7A illustrating the routing of the line portions within the channels of the control assembly.
Figure 7C:
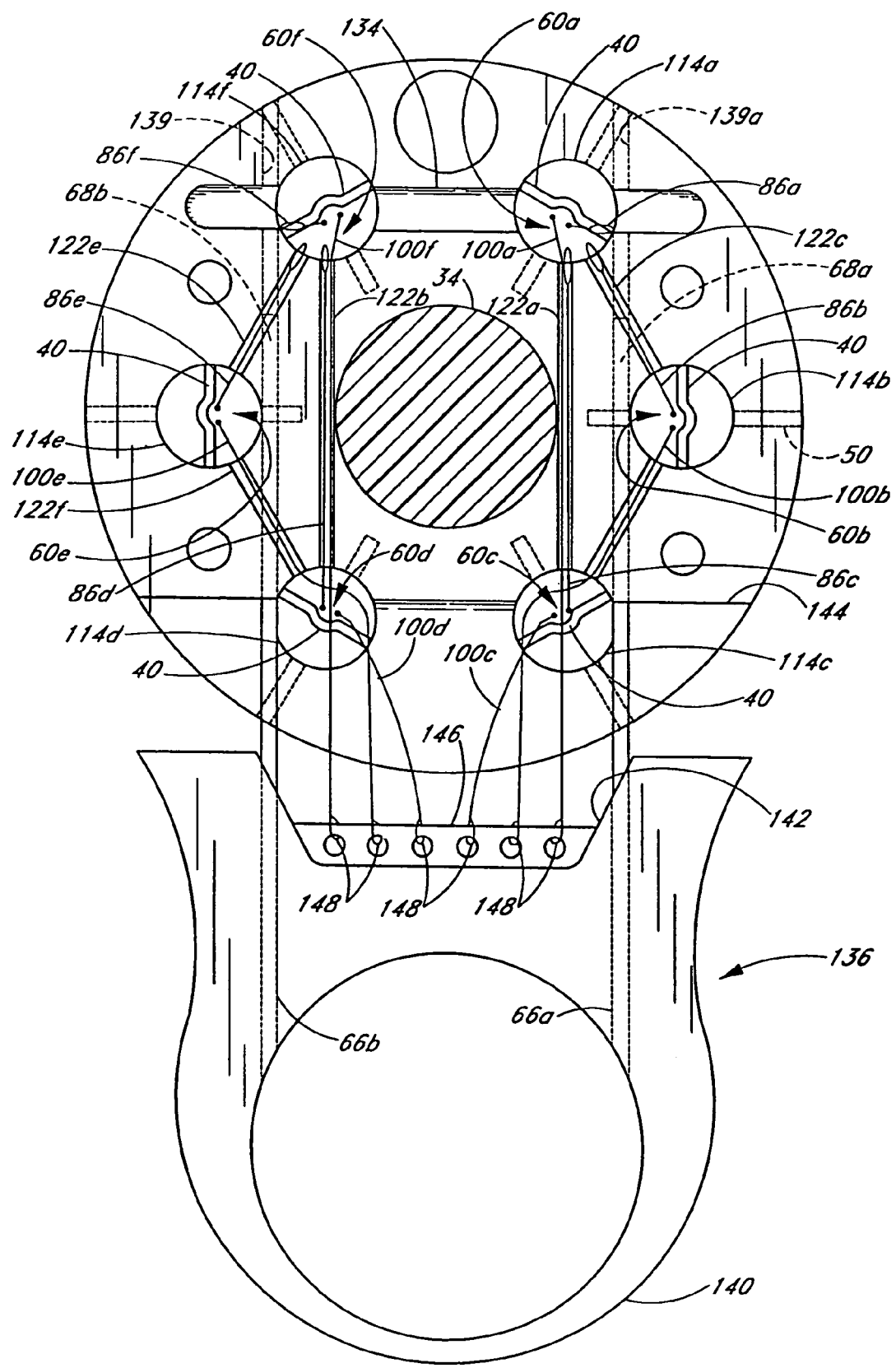
FIG. 7C is an enlarged view of the arrangement of FIG. 7B, showing a release member being pulled away from a body portion of the control assembly.

With reference also to FIG. 7A, in a preferred embodiment, the body portion 112 includes six passages 114, referred to specifically by the reference numerals 114a-114f. As a matter of convenience, the passages 114a-114f are referred to herein by their relative positions as depicted in FIGS. 7A-C. As such, passages 114a and 114f comprise an upper pair of passages, passages 114b and 114e comprise a central pair of passages and passages 114c and 114d comprise a lower pair of passages. Passage 114a is positioned to the right of a vertical axis $A_v$ passing through the center of the shaft 34 in FIGS. 7A and 7B. The remaining passages 114b-114f are distributed in a clockwise direction in an equally spaced relation to one another.

With particular reference to FIGS. 7A and 8, each of the above-described passages 114a-f are configured to receive a proximal end of one of the push rods 40. The push rods 40 are secured within their respective passages 114a-f by a shaft 150 passing through an opening (not shown) within the push rod 40 and being supported by the body portion 112 of the control assembly 38. Thus, as described above, the push rods 40 are fixed for axial movement with the control assembly 38.

Figure 10:
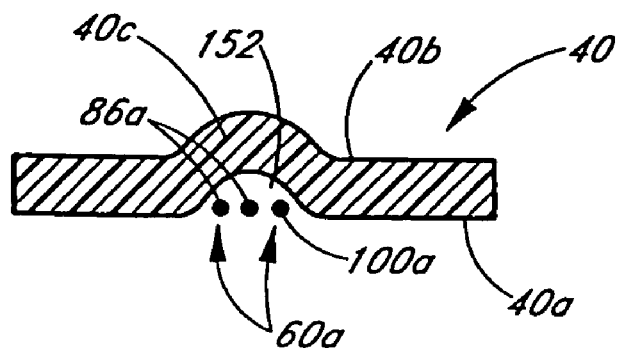
FIG. 10 is a cross-sectional view of one of the plurality of elongate push rods, taken along line 10-10 of FIG. 8.

In the illustrated embodiment, the push rods are supported generally in the center of the passages 114a-f, with their respective inner surfaces 40a arranged generally tangentially to the center axis of the shaft 34. In addition, with reference also to FIG. 10, a center portion 40c of each push rod 40 is generally semicircular in cross-section such that the inward facing surface 40a defines a recess 152. Preferably, the recess 152 is configured to accommodate one of the lines 60a-f, respectively, as described above in relation to FIG. 5. As shown in FIG. 10, the line 60a consists of the retaining loop 86a and the free end 100a, as is also described above in relation to FIG. 5.

With reference next to FIGS. 7A-C, a plurality of channels, referred to generally by the reference numeral 122, are defined by a proximal end surface of the body portion 112 of the control assembly 38. Each of the channels 122 interconnect two of the passages 114a-114f and are configured to accommodate a portion of one or more lines, such as the line 60a, as is described in greater detail below. Specifically, in a preferred arrangement, a first channel 122a extends generally parallel to the vertical axis $A_v$ and interconnects the passages 114a and 114c. Similarly, a second channel 122b extends generally parallel to the channel 122a and interconnects the passages 114d and 114f. Third and fourth channels 122c, 122d interconnect the passages 114a and 114b and passages 114b and 114c, respectively. Similarly, fifth and sixth channels 122e, 122f interconnect passages 114f and 114e and passages 114e and 114d, respectively.

Preferably, each of the channels 122a-f are arranged to generally intersect a center of the passages 114 that they interconnect. The channels 122a, 122c and 122d form a triangular shape on the right-hand side of the vertical axis $A_v$. The channels 122b, 122e and 122f form a triangular shape on the left-hand side of the vertical axis $A_v$, which shape is a mirror image of the triangular shape defined by channels 122a, 122c and 122d.

An additional channel 134 interconnects the passages 114a and 114f and extends in a direction generally parallel to a horizontal axis $A_H$ as depicted in FIGS. 7A-C. The channel 134 is defined by a proximal surface of the body portion 112 and, preferably, is substantially larger in both width and depth than the channels 122a-f. Preferably, the channel 134 has a width approximately one-half the diameter of the passages 114a, 114f and is semicircular in cross-sectional shape. Desirably, the channel 134 passes approximately through the centers of the passages 114a, 114f.

The control assembly 38 also includes a release member 136 that preferably is configured to selectively release the releasable stitch, thereby releasing the cardiac harness 42 from the delivery device 30. With reference also to FIG. 9, a portion of the release member 136 preferably is received within a cavity 137 of the body portion 112, which is located on an opposite side of the horizontal axis $A_H$ from the channel 134. The cavity 137 defines a support surface 138 which, along with a corresponding portion of the distal surface of the cover 116 (see FIG. 6), supports a portion of the release member 136.

Desirably, the retaining rod 68, illustrated schematically in FIG. 5, comprises a pair of rods 68a,b that are part of the release member 136 as shown in FIGS. 7A-C and 9. The pair of rods 68a,b extend outwardly (depicted vertically in FIGS. 7A-C) from the release member 136 and are slidably received in corresponding bores 139 formed within the body portion 112 of the control assembly 38. Preferably, the bores 139 are spaced on opposing sides of the vertical axis $A_v$. The rods 68a,b preferably are long enough such that distal end portions of the rods 68a,b pass through the channel 134.

The release member 136 defines a pull portion 140, which extends in an outward direction away from the body portion 112. The pull portion 140 preferably is generally annular in shape, such that a user of the delivery device 30 can grasp the release member 136 with one or more fingers extending through a hole defined by the pull portion 140. It is to be understood that other suitable constructions may also be used to permit a user of the device 30 to grasp and pull the release member 136 away from the body portion 112, such as providing a pull tab, for example.

The release member 136 also includes a preferably trapezoidal shaped cavity 142 extending inwardly from an inward facing surface 144 of the release member 136. The cavity 142 preferably is sized and shaped to avoid closing off the passages 114c and 114d.

The release member 136 preferably includes an attachment portion 146 that extends from a wall of the cavity 142 and toward the body portion 112. Preferably, the attachment portion 146 is arranged so that, as shown on FIGS. 7B and 9, a space 147 is disposed between the attachment portion 146 and the support surface 138 of the body portion 112. As shown more particularly in FIG. 9, the attachment portion 146 preferably is not as thick as the release member 136 and, desirably is about one-quarter or less of the thickness of the release member 136. As shown particularly in FIG. 9, an upper surface 149 of the attachment portion 146 preferably is spaced 147 from the support surface 138 of the body portion 112.

With reference again to FIGS. 7A-C and 8, the attachment portion 146 preferably includes a plurality of holes 148 extending therethrough in a direction generally parallel to a longitudinal axis of the shaft 34. In the illustrated embodiment, there are six holes 148, one hole 148 corresponding to each of the passages 114a-f.

With particular reference to FIG. 7B, the free ends 100 of the lines 60 preferably are tied to corresponding holes 148 of the attachment portion 146. As a more specific example, free end 100a of line 60a extends downwardly along the corresponding rod 40 (see FIG. 10) and enters passage 114a, from which it is directed into channel 122a and into the cavity 142. The free end 100a is then tied onto one of the holes 148 of the attachment portion 146. Thus, the free end 100a of the line 60a is affixed to the release member 136.

The retention loop 86a portion of line 60a also extends downwardly along the corresponding rod 40 (see FIG. 10) and into the passage 114a. From the passage 114a the loop 86a is directed into the channel 134 and, as illustrated in FIG. 7B, is looped about the right-most rod 68a of the release member 136. Looping the retention loop 86a around the rod 68a anchors the loop 86a and thus prevents the line 60a from unraveling. Note that for convenience in illustration, the retention loop 86a, which actually comprises two portions of line as shown in FIG. 10, is illustrated in FIG. 7B as a single line. This is done to present a less-cluttered drawing.

The other free ends 100b-f and retention loops 86b-f preferably are arranged similarly, although they are customized for their respective positions in the device. For example, free end 100b extends from passage 114b through channel 122d into the cavity 142 and is affixed to a hole 148. Free end 100c is directed directly from passage 114c into the cavity 142 and is affixed to a hole 148. Free end 100d also extends directly from the passage 114b into the cavity 142 and is affixed to a hole 148. Free end 100e extends out of passage 114e through channel 122f into the cavity 142 and is affixed to a hole 148. Free end 100f extends from passage 114f and through channel 122b into the cavity 142 and is affixed to a hole 148.

With regard to the retention loops 86, retention loop 86b extends from passage 114b through channel 122c into channel 134 and is looped around the tight rod 68a. Loop 86c extends from passage 114c through channel 122a into channel 134 and is looped about the right rod 68a. Retention loop 86d extends from passage 114d through channel 122b into channel 134 and is looped about the left rod 68b. Retention loop 86e extends out of passage 114e through channel 122e into channel 134 and is looped about the left rod 68b. Retention loop 86f extends from passage 114f into channel 134 and is looped about the left rod 68b.

In operation, the release member 136 is configured to release loops 86a-f, unravel the lines 60a-f from the push rods 40 and thereby release the cardiac harness 42 from the push rods 40. More specifically, and with reference to FIG. 7C, as the release member 136 is pulled away from the body 112 of the control assembly 38, the rods 68a-b are also pulled through the channel 134 such that the retention loops 86a-f are released from the rods 68a-b. Simultaneously, because the free ends 100a-f of the lines 60a are tied onto one of the holes 148 of the attachment portion 146, the release member 136 pulls on the free ends 100a-f. Since the retention loops 86a-f are released from the rods 68a-b, pulling of the free ends 100a-f unravels the lines 60a-f, thereby releasing the cardiac harness 42 from the push rods 40, as is described further below in connection with FIGS. 11A-C.

Figure 11A:
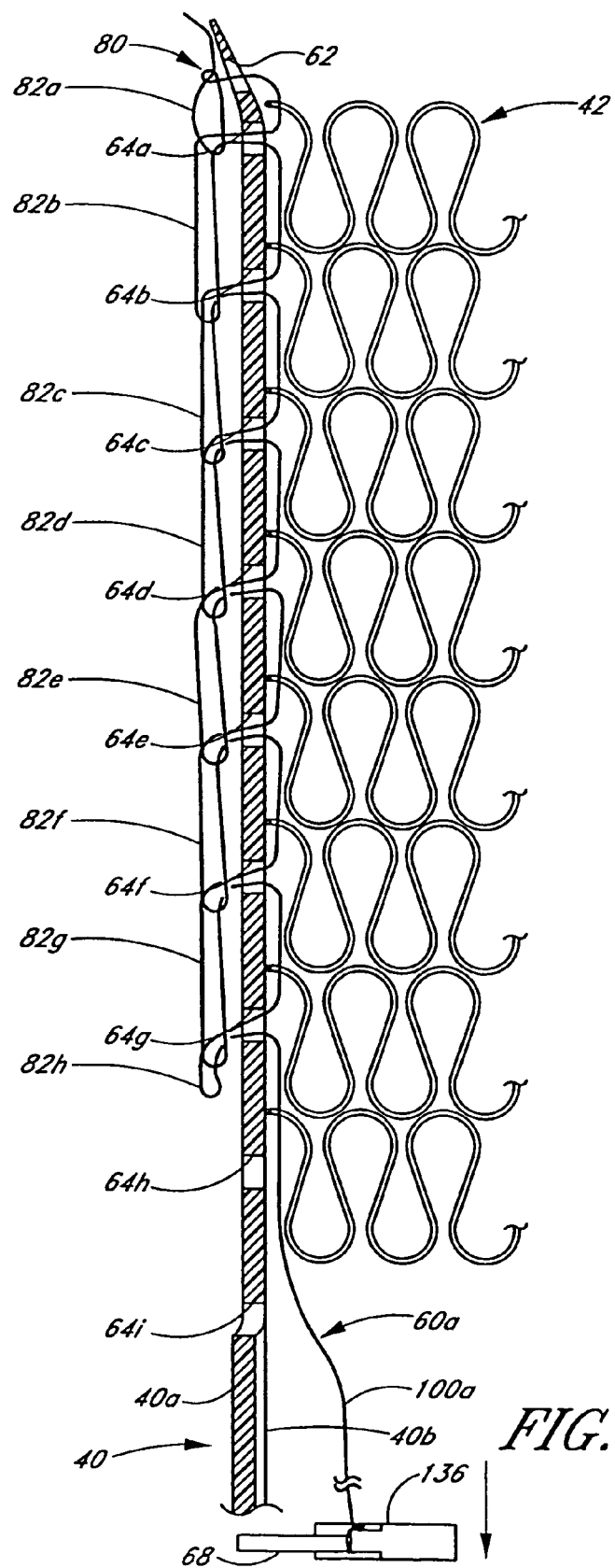
FIG. 11A is a cross-sectional view of one of the plurality of push rods, illustrating the releasable stitch of FIG. 5 being unraveled to release the cardiac harness from the push rod.
Figure 11B:
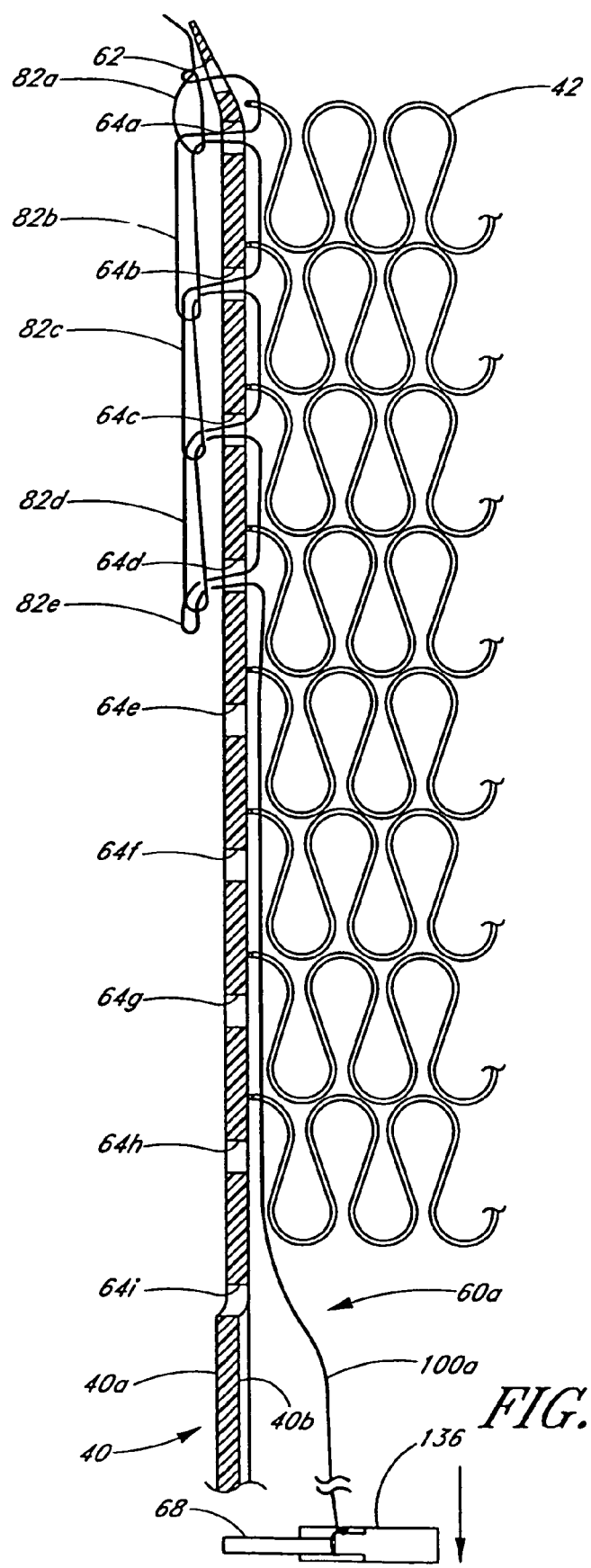
FIG. 11B is a cross-sectional view of the push rod of FIG. 11A, illustrating the releasable stitch in a further unraveled condition.
Figure 11C:
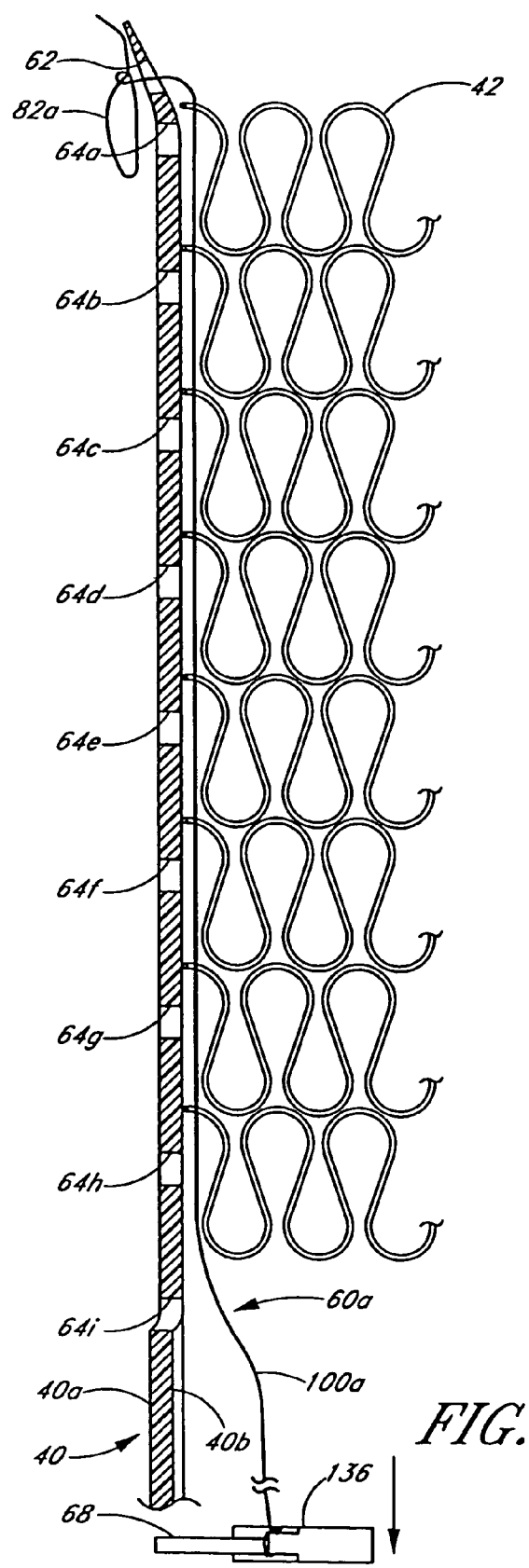
FIG. 11C is a cross-sectional view of the push rod of FIG. 11A, illustrating the releasable stitch in a substantially released condition.

FIGS. 11A through 11C illustrate a preferred sequence of unravelment of the releasable stitch of line 60a. With additional reference to FIG. 5, as described above, in a secured position of the releasable stitch, preferably the retaining loop 86a is looped around the rod 68 of the release member 136 to inhibit unravelment of the stitch. However, when the rod 68 is retracted to release the retaining loop 86a, and the free end 100a is pulled by the release member 136, the retaining loop 86a is pulled through the loop 82h by the free end 100a.

Returning to FIG. 11A, as the release member 136 continues to be pulled away from the main body 112 of the control assembly 38, the loop 82h is pulled through the loop 82g in a manner similar to that described above. With reference to FIG. 11B, as the free end 100a continues to be pulled, each successive loop 82g, 82f, 82e, 82d, 82c, 82b, 82a is pulled through its distally-adjacent loop. In FIG. 11B, loop 82e is illustrated as being pulled through loop 82d. Subsequently, loop 82d is pulled through loop 82c, which is then pulled through loop 82b. Finally, loop 82b is finally pulled through the initial loop 82a, as illustrated in FIG. 12C.

The initial loop 82a, which preferably comprises a slip knot 80, preferably completely unties itself and is pulled through the distal-most opening 62 to release the cardiac harness 42 from the push rod 40. In a similar manner, because the remainder of the lines 60b-f are also secured to the release member 136, the cardiac harness 42 preferably is simultaneously released from each of the plurality of push rods 40.

Figure 12:
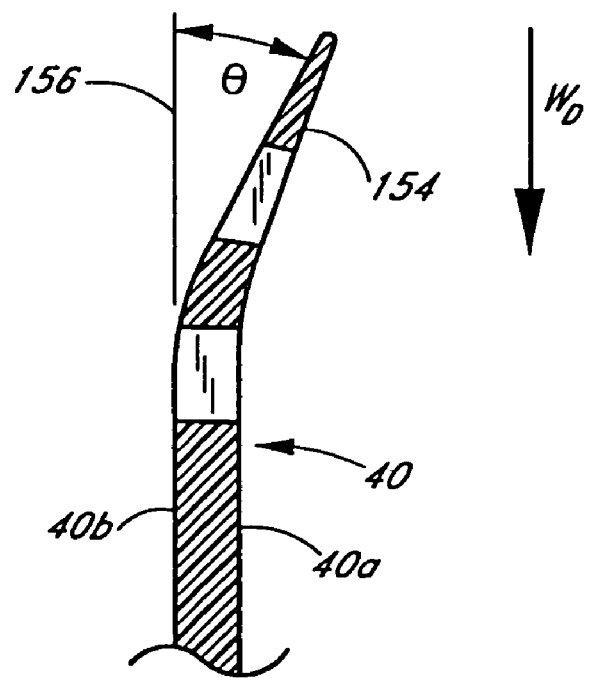
FIG. 12 is a cross-sectional view of a distal tip of one of the plurality of elongate push rods, taken along line 12-12 of FIG. 4.

With next reference to FIG. 12, a distal end of one of the plurality of push rods 40 is shown in section. As described above, the push rod 40 has an inward facing surface 40b, which faces a center axis of shaft 34, and an outward facing surface 40a, which laces away from a center axis of the shaft 34. Thus, in operation, the inner surface 40b of each of the push rods 40 is positioned adjacent to, and preferably in contact with, the cardiac harness 42.

The distal end of the push rod 40 includes a tip portion 154 that, in a preferred arrangement, is canted outwardly away from a center axis of the shaft 34. Thus, the inner surface 40b of the tip portion 154 defines an angle θ with respect to a line 156 extending from the inner surface 40b of the remainder of the push rod 40. In a preferred arrangement, the angle θ is between about 5-60 degrees, and more preferably is between about 10-45 degrees. Most preferably, the angle is between about 15-35 degrees.

As will be appreciated by one of skill in the art, although preferably the inner surface 40b is generally planar in a relaxed orientation, the push rod 40 is configured to be deflectable so as to splay outwardly from a distal end of the housing 36 so as to conform to an outer surface of a patient's heart while in use. Accordingly, the push rod 40 is not always oriented such that the inner surface 40b is necessarily planar. However, when the push rod 40 is in a splayed orientation, any given point on the surface 40b preferably is either the same perpendicular distance from a center axis of the shaft 34, or a greater distance, than any point on the surface 40b proximal to the given point. That is, preferably, the inward facing surface 40b does not have any inwardly extending portions when moving from a proximal end of the push rod 40 toward a distal end of the push rod 40.

In operation, once the cardiac harness 42 has been positioned on a patient's heart, the control assembly 38 is retracted relative to the shaft 34 such that the plurality of push rods 40 are also retracted relative to the cardiac harness 42. Upon retraction of the delivery device 30, relative motion is experienced between the inner surface 40b and the cardiac harness 42. That is, the inner surface 40b of the push rod 40 slides along the cardiac harness 42 along a withdrawal path in a withdrawal direction $W_D$, as indicated by the arrow in FIG. 12.

Preferably, the tip 154 is configured with an angle such that upon sliding motion of the push rod 40 relative to the cardiac harness 42, no force is exerted by the inner surface 40b tending to drag the cardiac harness 42 from its position on the heart. That is, the construction of the inward facing surface 40b of the push rods 40 is such that non-frictional force components parallel to the withdrawal path and attributable to forces exerted by the inner surface 40b on the cardiac harness 42 are directed distally, without substantial frictional force components directed proximally, or in the withdrawal direction $W_D$. Advantageously, once the cardiac harness 42 is properly positioned on the heart, retraction of the push rods 40 does not disturb the positioning of the harness 42.

With next reference to FIGS. 13-17, an introducer assembly 160 assists in creating an access opening in the pericardium of a patient's heart to permit access of the delivery device 30 to the heart. In the illustrated embodiment, the introducer assembly 160 includes an introducer sleeve 162 and a dilator sleeve 164.

With particular reference to FIG. 13, the introducer sleeve 162 preferably is a thin-walled, tubular element having a substantially circular cross-sectional shape. A distal end 163 of the sleeve 162 comprises a plurality of flared portions 165 that are biased outwardly from a longitudinal axis $A_s$ of the sleeve 162. In the illustrated embodiment, a portion of the sleeve 162 is divided into several elongate strips 166. Preferably, the elongate strips 166 are spaced apart from each other. In a preferred arrangement, about the distal-most two-thirds of the length of the introducer sleeve 162 is divided into the spaced apart elongate strips 166. Preferably, six such strips 166 are provided. However, other suitable numbers of strips may also be used.

With continued reference to FIG. 13, the strips 166 preferably extend generally parallel to the longitudinal axis $A_s$ of the sleeve, except that at the distal end of each strip, a flared portion 165 is biased generally outwardly. Preferably, the strip 166 bends at a transition portion 167 to transition from the generally straight portion of the strip to the flared portions 165. In the illustrated embodiment, the flared portions 165 also extend somewhat in a direction generally transverse to the longitudinal axis $A_s$.

Preferably, a resilient annular member, such as an elastic ring 168, is positioned toward the distal end 163 of the introducer sleeve 162 at or adjacent the transition portions 167 of the elongate strips 166. Desirably, the elastic ring 168 is configured to bias the strips 166 into a reduced-diameter portion, which is operable to ease insertion of the introducer sleeve 162 into an incision in the pericardium, as is described in greater detail below.

With particular reference to FIG. 14, the dilator sleeve 164 preferably is a thin-walled, tubular member, which is also substantially circular in cross-section. An outer diameter of the dilator sleeve 164 is configured to be slightly smaller than an inner diameter of the introducer sleeve 162. Accordingly, the dilator sleeve 164 may be slidably inserted within the introducer sleeve 162, as illustrated in FIG. 15. The dilator sleeve 164 may also have an enlarged diameter portion 170 on its proximal most end to limit the insertion within the introducer sleeve 162. Further, a releasable locking system may be provided so that the dilator sleeve 164 may be releasably engaged with the introducer sleeve 162.

In the assembled condition illustrated in FIG. 15, the dilator sleeve 164 presses against an inner surface of the reduced-diameter portion of the introducer sleeve 162 to force the reduced-diameter portion outward against the biasing force provided by the elastic ring 168. Thus, in the assembled configuration, the reduced diameter portion of the introducer sleeve 162 is enlarged and the introducer assembly 160 is configured to provide an access pathway for the delivery device 30. Preferably, an inner diameter of the sleeve 164 is greater than an outer diameter of the delivery device 30 so that the device can be advanced through the sleeve 164.

FIG. 16 illustrates a human heart 172, which is enclosed within a pericardium 174. To permit introduction of the delivery device 30 to within the pericardium 174, preferably, a small incision 176 is made in the pericardium 174 adjacent the apex of the heart. With reference next to FIG. 17, the introducer sleeve 162, in its contracted orientation, is introduced into and through the incision 176. In practice, one side of the distal end of the introducer sleeve 162 may be inserted into the incision 176 first, followed by the remaining side.

Figure 18:
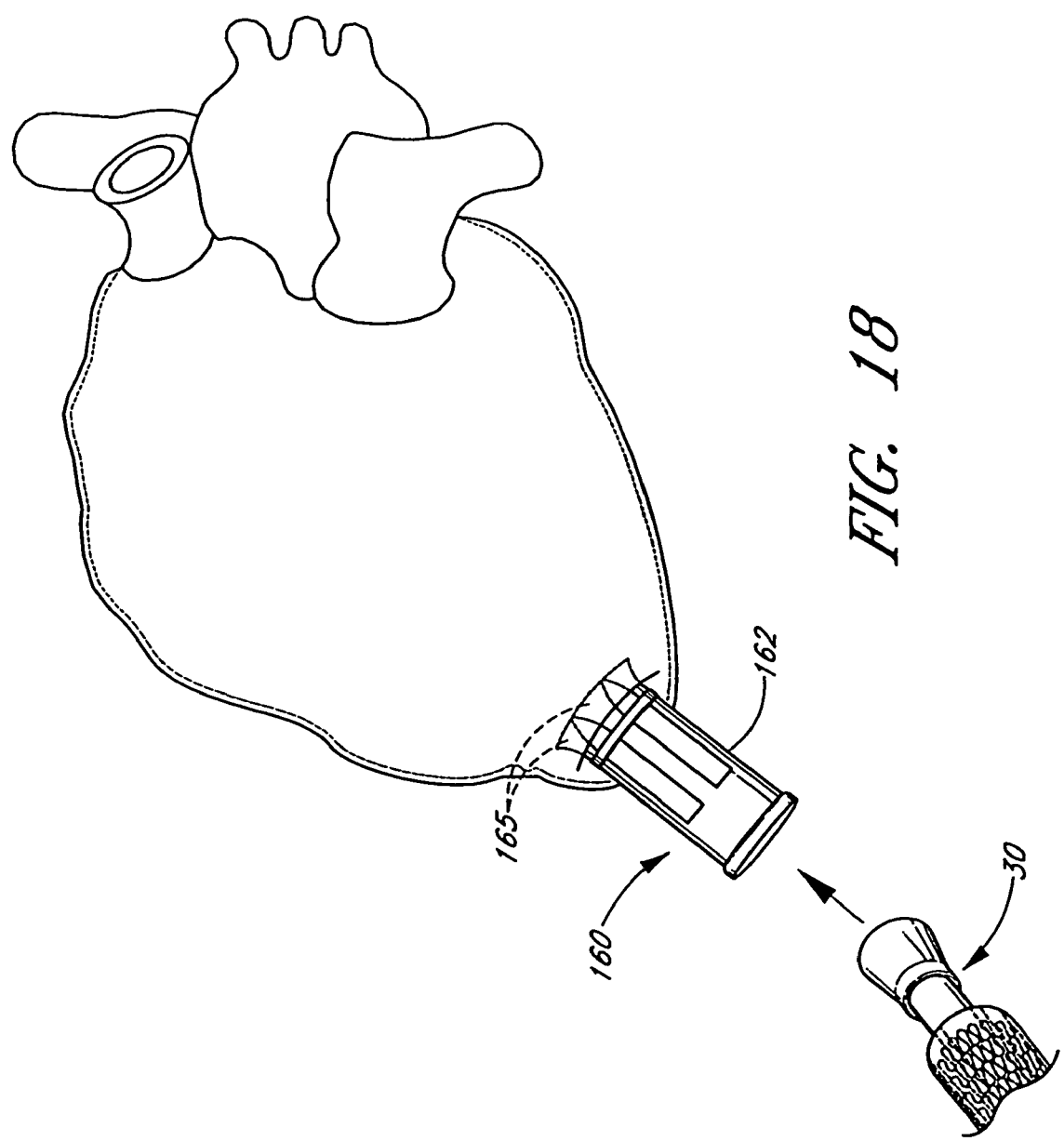
FIG. 18 is a perspective view of the heart of FIG. 16 with the introducer assembly, in an assembled condition, providing an access pathway through the pericardium for introduction of the delivery device.

With reference next to FIG. 18, once the flared portions 165 of the introducer sleeve 162 have been advanced through the slit 176, the dilator sleeve 164 is then introduced within the introducer sleeve 162 to urge the introducer sleeve 162 into its expanded configuration. In this configuration, the flared portions 165 are expanded to a diameter greater than the diameter of the rest of the introducer sleeve 162 and preferably greater than the size of the incision 176. As such, the flared portions 165 press upon and open the incision 176 and the surrounding portion of the pericardium so as to create a space between at least part of the pericardium and the heart. Further, the flared portions 165 function as a lock to resist pulling the introducer out of the incision 176. Accordingly, the introducer assembly 160 is effectively locked in place between the heart 172 and the pericardium 174.

Since the dilator sleeve 164 dilates the introducer sleeve 162, an access pathway is created to allow the delivery device 30 to be advanced therethrough and through the pericardium. The delivery device 30 is advanced through the pathway so as to deliver the cardiac harness 42 onto the heart 172. When the procedure is completed, the delivery device 30 is retracted through the access pathway and the introducer arrangement 160 is removed in generally the reverse order of the insertion.

As discussed above, in an additional embodiment the housing 36 is generally elliptical. It is to be understood that, in still further embodiments, the introducer sleeve 162 and dilator sleeve 164 are also elliptical, having a major axis and a minor axis. Further, each of these components may have any desired cross-sectional shape. As such, they may have a shape that is customized for any desired type or shape of minimally invasive surgical entry path.

FIGS. 19-23 illustrate the use of a delivery device 30, preferably configured substantially as described above, to deliver a cardiac harness 42 onto a heart 172. Preferably, the delivery device 30 is configured to locate and grasp the heart 172, accurately position the cardiac harness 42 onto the heart 172, and permit withdrawal of the delivery device 30 without disturbing the positioning of the cardiac harness 42.

Figures 19, 20:
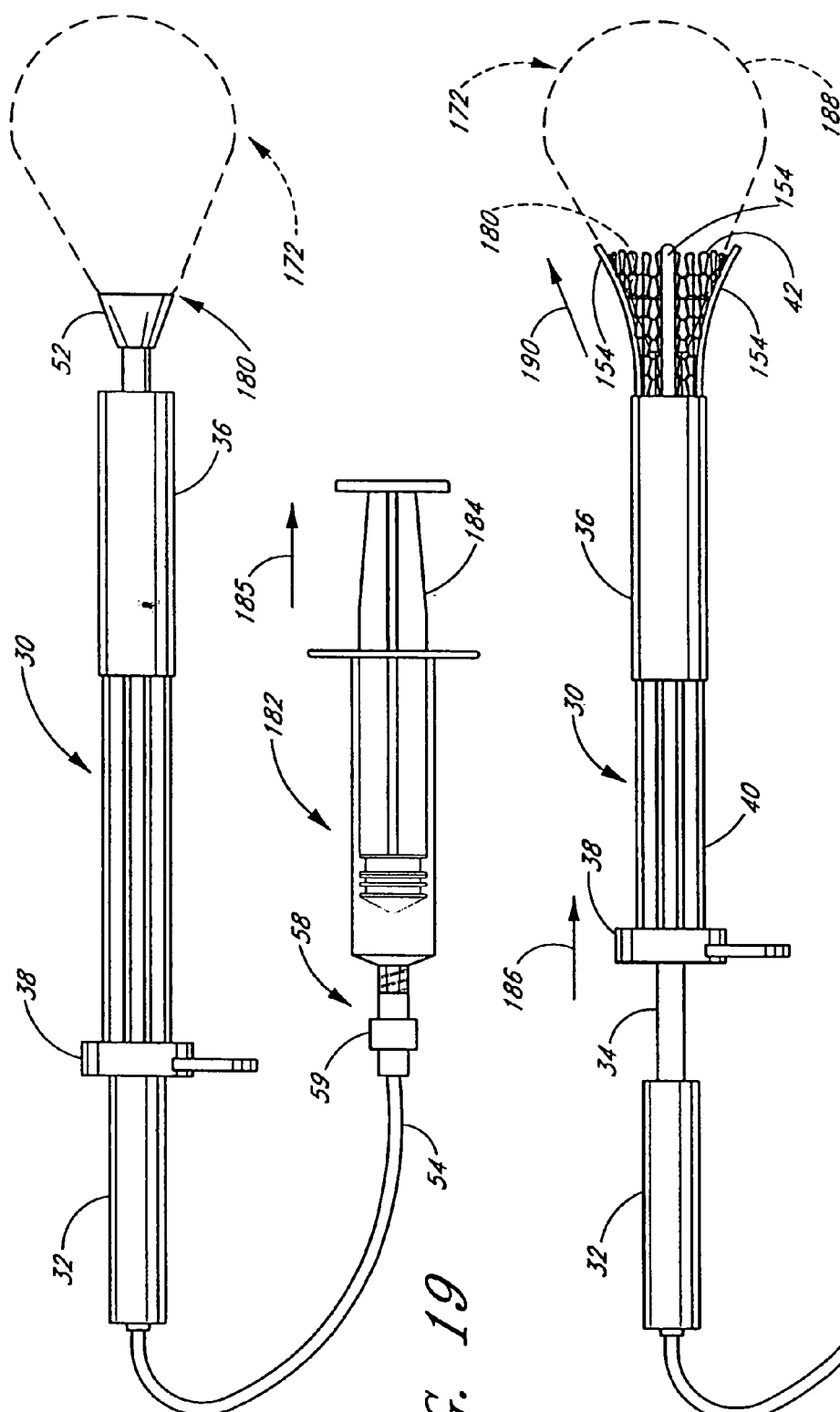
FIG. 19 is a side elevational view of the delivery device of FIGS. 1-12, with a pump member, or, specifically, a syringe, attached to a suction assembly of the delivery device. The suction assembly includes a suction cup member, which is configured to securely hold the heart relative to the delivery device during advancement of the cardiac harness over the heart.
FIG. 20 is a side elevational view of the delivery device of FIG. 19 with the cardiac harness in a partially advanced position.

With reference to FIG. 19, preferably, the suction cup 52 of the delivery device 30 engages an apex portion 180 of the heart 172, which is illustrated schematically in FIGS. 19-23. The distal end of the delivery device 30 may access the heart 172 through any suitable method, but preferably through a minimally invasive procedure such as that described in relation to FIG. 16-18. In FIGS. 19-23, the pericardium 174 (FIG. 16) is omitted to ease illustration.

A pump device, such as a syringe 182, is connected to the hose 54 through the connector 58. Desirably, the syringe 182 is connected to the hose 54 with the plunger 184 in a compressed position. Once connected, the plunger 184 is retracted (as indicated by the arrow 185 in FIG. 19) to create a vacuum condition within the hose 54 and, thus, within the space defined by the interior of the suction cup member 52. Due to the vacuum condition, the suction cup member 52 grasps the apex 180 such that the heart 172 is held in a desired position relative to the delivery device 30.

Preferably, the connector 58 includes a one-way valve 59 that is configured to inhibit air from flowing from the syringe to the tube 54 through the connector 58. Accordingly, the syringe 182 may be removed from the tube 54 once a vacuum condition has been created. Although a syringe 182 is preferred as a dump member due to its simplicity and low cost, other suitable pump devices may also be used to create a vacuum within the tube 54, as will be appreciated by one of skill in the art.

With reference next to FIG. 20, once the delivery device 30 has been properly secured to the base 180 of the heart 172, the control assembly 38 may be advanced, relative to the shall 34, toward the heart 172, as indicated by the arrow 186 in FIG. 20. The plurality of push rods 40 are advanced toward the heart 172 with the control assembly 38 thereby advancing the cardiac harness 42 from its compacted configuration within the housing 36 onto the heart 172 in a direction from the base 188 to the apex 180, as indicated by the arrow 190 in FIG. 20. As shown, the harness 42 preferably stretches elastically to fit over the heart. However, it is to be understood that a substantially non-elastic harness embodiment can also be delivered by this device and method.

As illustrated in FIG. 20, the plurality of push rods 40 splay outwardly to conform to the shape of the heart 172 as they are advanced relative to the shall 34 of the delivery device 30. As described above, preferably the tips 154 of the push rods 40 are canted at an outward angle θ relative to the remainder of the push rod 40 such that contact of the tip 154 with the heart 172 is generally avoided, thereby preventing trauma to the heart 172.

With reference to FIG. 21, the control assembly 38 continues to be advanced until the cardiac harness 42 is properly positioned on the heart 172. Once the cardiac harness 42 is properly positioned, the release member 136 is pulled away from the main body 112 of the control assembly 38, as indicated by the arrow 192. Accordingly, the cardiac harness 42 is released from the plurality of push rods 40, preferably in a manner similar to that described above with reference to FIG. 11A-C.

With reference to FIG. 22, once the cardiac harness 42 has been released from the plurality of push rods 40, the generally-elastic harness preferably contracts onto the heart. The control assembly 38 is then retracted relative to the shaft 34 to retract the plurality of push rods 40 from the cardiac harness 42, which remains on the heart 172. As noted above, preferably, the push rods 40 are configured such that retraction of the push rods 40 does not tend to pull the cardiac harness 42 from its desired position on the heart 172. Specifically, in the illustrated embodiment, the outwardly canted tips 154 of the plurality of push rods 40 help prevent the push rods 40 from exerting a pulling force on the cardiac harness 42.

Figure 23:
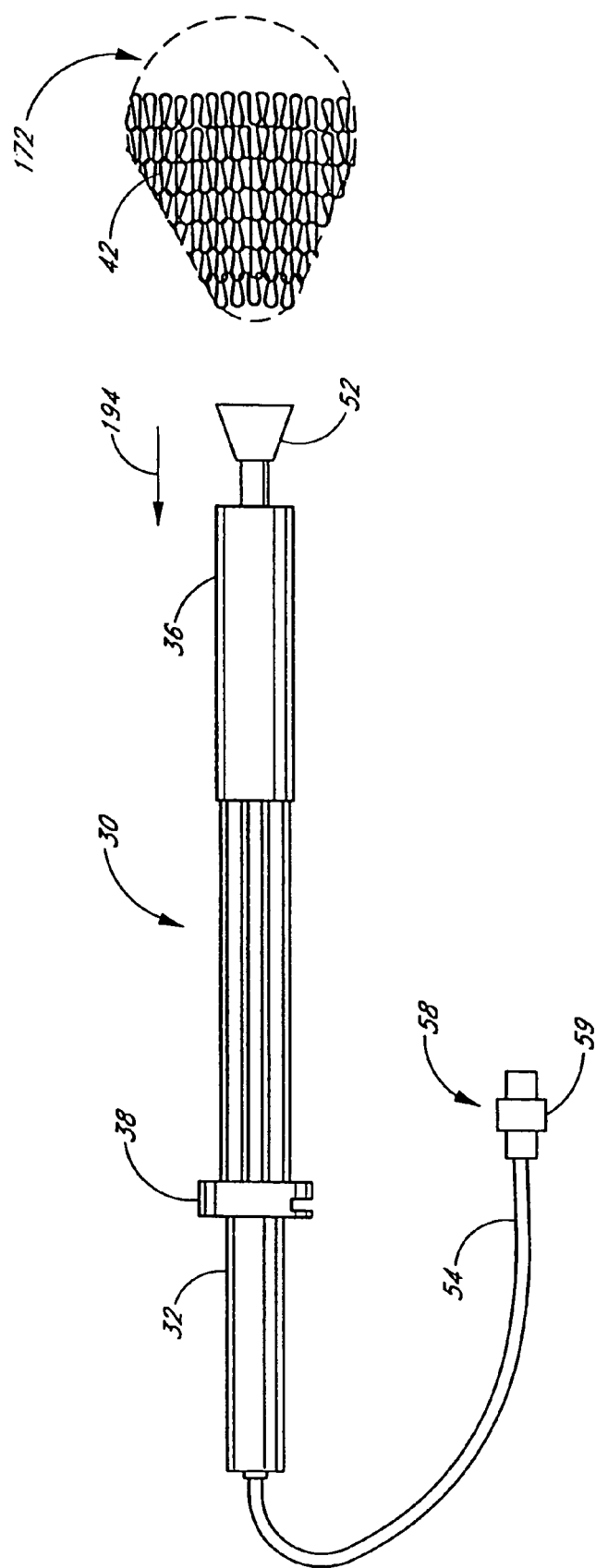
FIG. 23 is a side elevational view of the delivery device of FIG. 19 with the cardiac harness completely released and illustrating the delivery device being withdrawn from the heart.

With reference to FIG. 23, once the plurality of push rods have been fully retracted from the cardiac harness 42 and the heart 172, the one-way valve 59 within the connector 58 may be opened to release the vacuum condition with the tube 54. As a result, the delivery device 30 may be removed from the heart 172, as indicated by the arrow 194 in FIG. 23, as the suction cup member 52 is no longer grasping the heart 172. Thus, the delivery device 30 is retracted from the heart, leaving the cardiac harness 42 in place.

As discussed above, the delivery device 30 holds the cardiac harness 42 at several spaced apart locations. As such, the device exerts a distributed hold on the harness 42. Due to the distributed hold, the device can be used to advance the harness 42 as discussed above and also can be used to adjust the positioning and orientation of the harness without substantially deforming the harness 42. For example, if the harness is advanced distally farther than desired, the control assembly 38 can be pulled proximally somewhat in order to fine tune the position of the harness relative to the heart. Due to the distributed hold between the device 30 and the harness 42, the harness will move proximally as desired without substantial deformation, such as folding over itself or the like. Furthermore, in another embodiment, the position of the harness can be adjusted not only distally and proximally but also rotationally without substantially deforming the harness.

Although the delivery device 30 is especially well suited for use in a minimally invasive delivery procedure, the device 30 may also be used for open chest procedures, wherein the sternum of the patient is split to provide access to the heart 172. Accordingly, the delivery device 30 may be used with or without the delivery arrangement illustrated in FIGS. 13-18. In addition, although the device 30 described herein utilizes a plurality of push rods 40, other suitable structures may also be used as support structures to support the cardiac harness 40, when being advanced over the heart. For example, an expandable sleeve can serve as a support structure. Furthermore, it is to be understood that a cardiac harness 42 may be releasably supported in an expanded, or substantially expanded, configuration to a variety of support structures by the releasable stitch described herein, or by a similar releasable stitch arrangement.

In further keeping with the invention, several embodiments are disclosed for assisting the push rods in making the initial very steep bend around the apex of the heart when initially advancing the cardiac harness over the heart. Because the patients' hearts are enlarged, they may become globular or spherical, and the apex region of the heart may present an almost flat surface, or at least rounded surface for the cardiac harness to advance over. The pericardium may be tightly adhered to the epicardium, and due to the size of the heart, there may be very little space between the heart and ribs. All of these factors contribute to difficulty in advancing the cardiac harness, using conventional push rods, to make the initial bend at the apex region without buckling or kinking the push rods which may have to bend almost 90°.

In one embodiment, shown in FIGS. 24-34, a stylet 200 initially is straight, and it can be manipulated by the doctor to form a bend in the distal portion 202 of the stylet. The proximal portion 204 of the stylet should remain relatively straight and is less flexible than the distal portion 202. In one embodiment, push rod 206 has a longitudinal lumen 208 sized for slidably receiving the stylet. The distal end 210 of the push rod preferably has an initial bend in the distal end to assist in making the turn around the apex of the heart. In this embodiment, the stylet 200 is bent substantially at its distal portion 202 so that when the stylet is inserted into the longitudinal lumen 208, the distal end 210 of the push rod 206 will take on the substantial bend of the distal portion 202 of the stylet 200. The transverse cross-section of the stylet can be any configuration such as circular, rectangular, square, or any geometric shape that will facilitate forming a bend in the distal portion 202 of the stylet so that it remains bent. Further, the transverse cross-section of the longitudinal lumen 208 of the push rod 206 should be configured to correspond to the transverse cross-sectional shape of the stylet. In one embodiment, stylet 200 is slightly tapered so that the proximal end of the stylet 204 has a transverse cross-section that is somewhat larger than the transverse cross-section of the distal portion 202 of the stylet. Further, the longitudinal lumen 208 of the push rod 206 is correspondingly tapered so that the stylet 200 is more easily inserted and removed from the longitudinal lumen during use. The bend 212 in the distal portion 202 of the stylet 200 can range from only a few degrees up to approximately 90°. In this embodiment, the cardiac harness is releasably attached to the push rods 206 by means other than the lacing disclosed herein.

Figure 24:
FIG. 24 is an elevational view of a stylet for use in shaping bends in the push rods.
Figure 25:
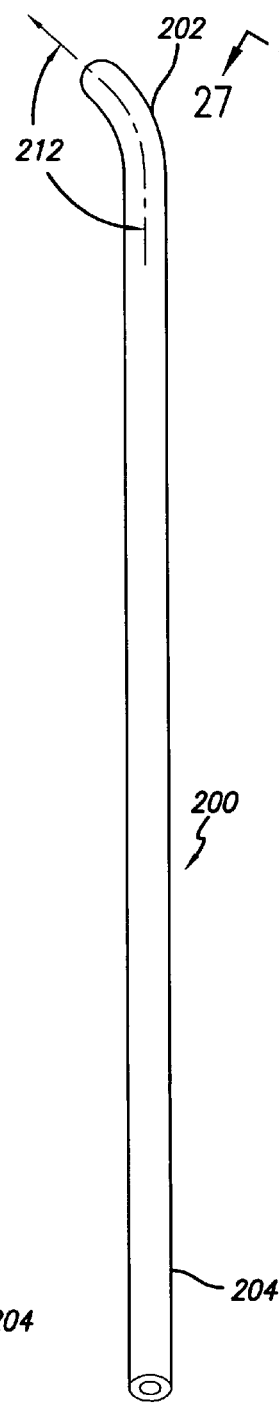
FIG. 25 is an elevational view of a stylet depicting a bend in the distal end of the stylet.
Figure 26:
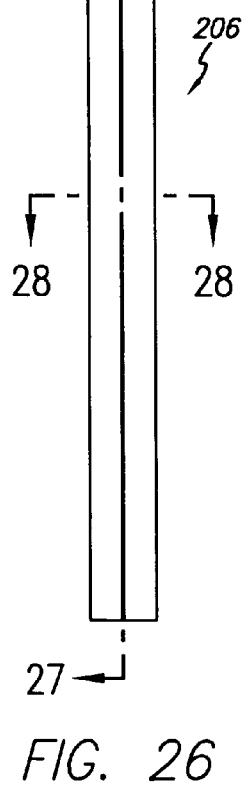
FIG. 26 is an elevational view depicting a push rod having a bend in its distal end.
Figure 27:
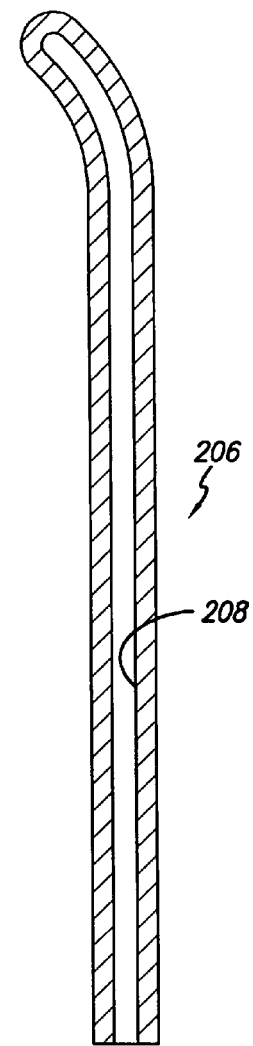
FIG. 27 is a transverse cross-sectional view taken along lines 27-27 depicting the push rod with a longitudinal lumen therein.
Figure 28:
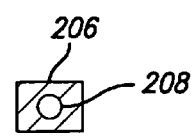
FIG. 28 is a cross-sectional view taken along lines 28-28 depicting the push rod with the longitudinal lumen therein.

With reference to FIGS. 29-32, the stylet 200 is substantially the same as that shown in FIGS. 24 and 25. The push rods 206 shown in FIGS. 30 and 31 have lacing holes 214 similar to the lacing holes disclosed in earlier embodiments of the push rods. The lacing holes are configured to receive lines to releasably attach the cardiac harness to the push rod. In this embodiment, the longitudinal lumen 216 extends from the proximal end 218 of the push rod to a point proximal of the proximal most lacing hole 214. The operation of stylet 200 in this embodiment is similar to that described in FIGS. 24-28 in which the distal portion 202 of the stylet has a bend 212 that will cause the distal end 210 of the push rod to take a similar bend when the stylet is inserted within longitudinal lumen 208. As previously stated, stylet 200 can be tapered, as well as longitudinal lumen 216, so that the stylet can be more easily inserted into and removed from the longitudinal lumen 216. The degree of bend 212 can be anywhere from a few degrees up to approximately 90°, depending upon the sphericity of the heart, especially in the apex region of the heart where it is most likely that the cardiac harness will initially engage the heart.

Figure 33:
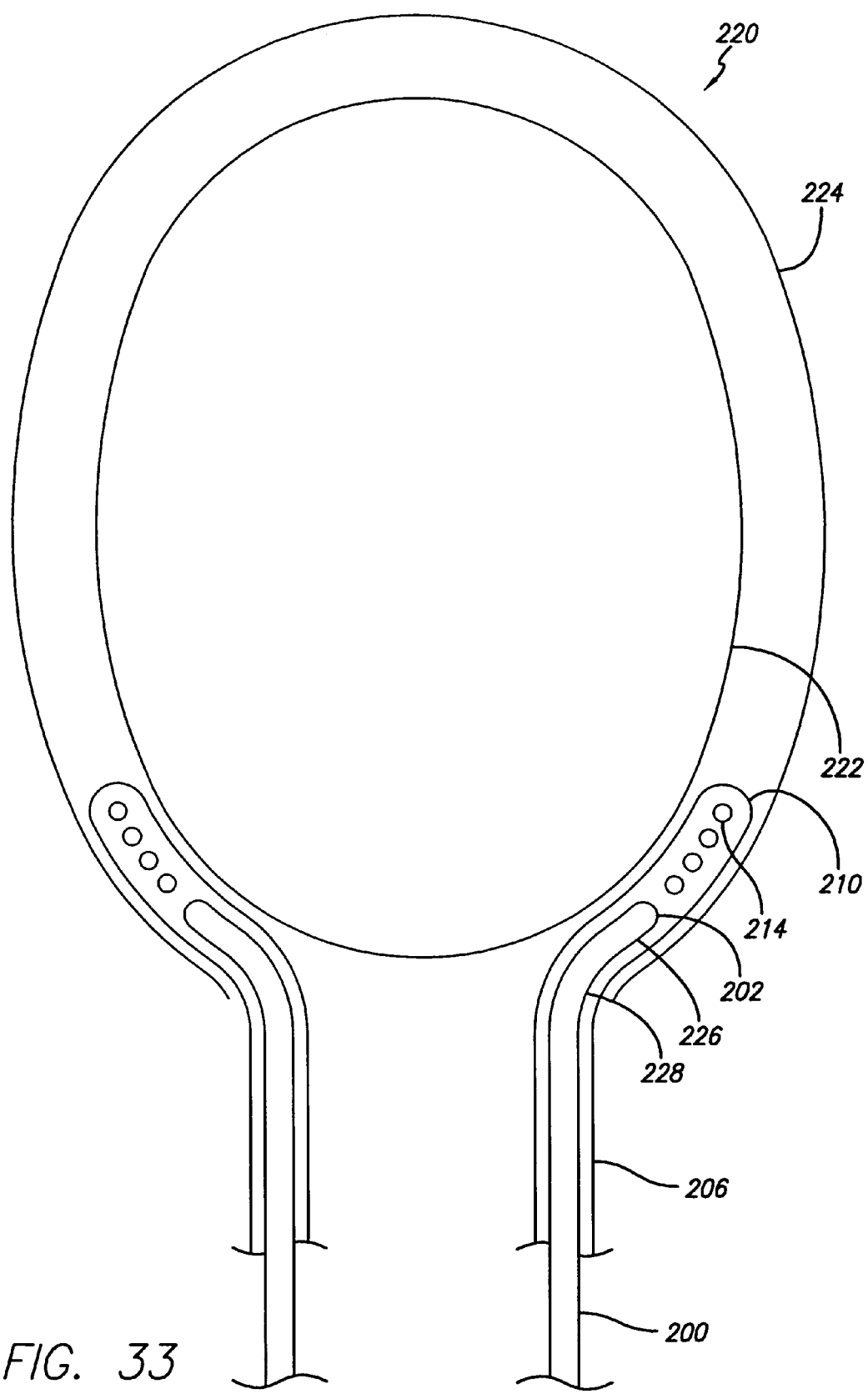
FIG. 33 is a side elevational view depicting the stylet and push rods of FIGS. 29-32 advancing onto the heart.
Figure 34:
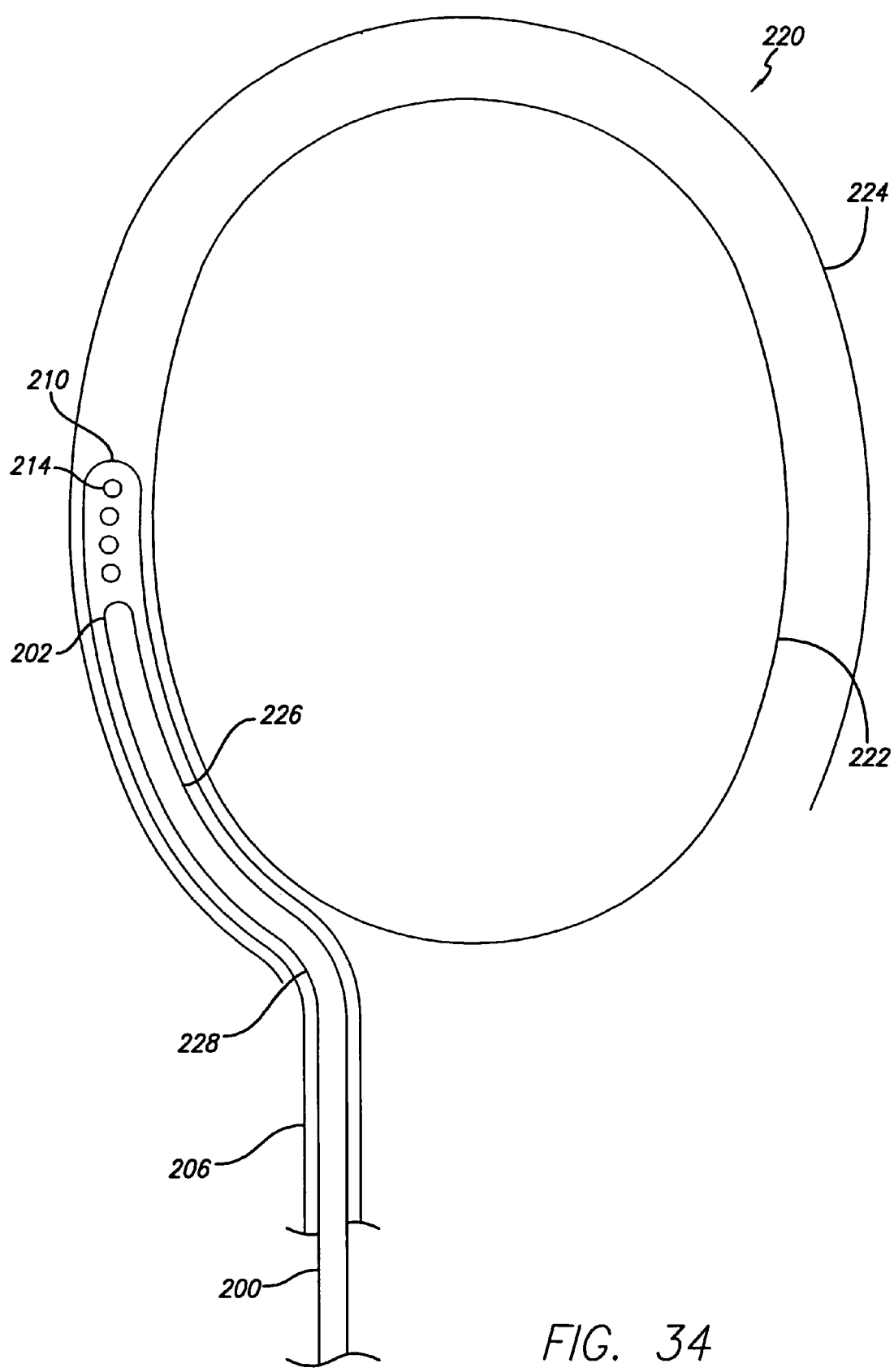
FIG. 34 is a side elevational view depicting the stylet and push rod assembly of FIGS. 29-32 where the push rod has been advanced distally onto the heart.
Figure 35A:
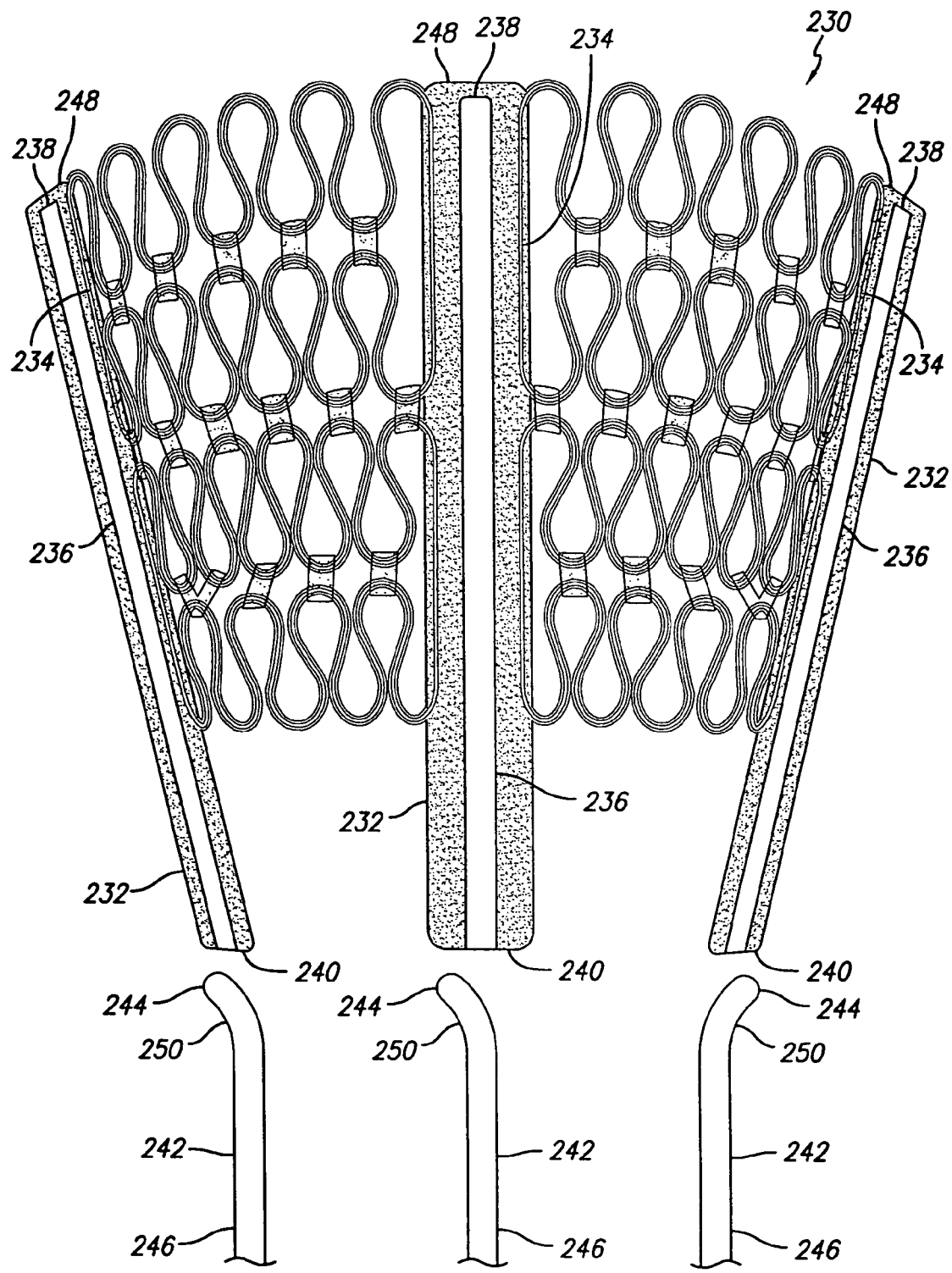
FIG. 35A is an elevational view depicting a cardiac harness mounted on push rods that slidably move in and out of sheaths attached to the cardiac harness.
Figure 35B:
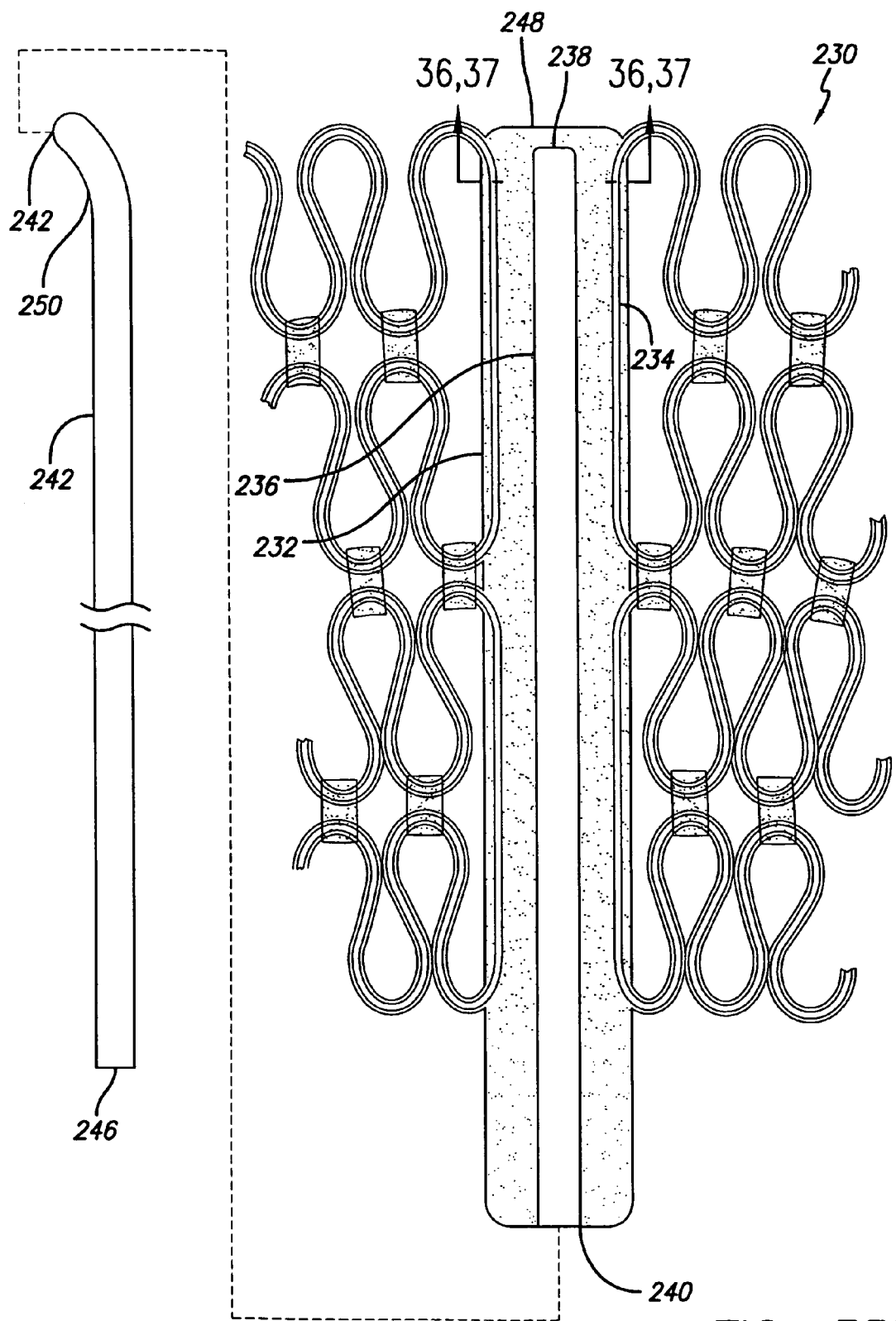
FIG. 35B is an enlarged elevational view of a portion of the cardiac harness assembly of FIG. 35A depicting the push rod configured for slidably inserting into the sheath.

As shown in FIGS. 33 and 34, the embodiments of the stylet 200 and push rods 206 shown in FIGS. 24-32 are deployed onto a heart 220. While FIGS. 33 and 34 do not show a typical heart shape, the heart can in fact be more spherical in congestive heart failure patients. The heart 220 shown in FIGS. 33 and 34 illustrate the severe curve or bend that the push rods 206 must navigate in order to slide along the epicardial surface 222 of the heart and under the pericardium 224. As shown, stylet 200 has first bend 226 (FIG. 33) in order to make the first turn as the push rod 206 comes into contact with the epicardial surface 222 of the heart 220.

The stylet 200 shown in FIG. 34 has a first bend 226 and a second bend 228 which will accommodate an advancement of the push rods 206 as they initially make the first turn when engaging the heart in the apex region and conform to a second bend as the push rods advance along the contour of the epicardial surface 222. As shown in FIG. 34, the stylet has been bent twice with different radii to accomplish what is essentially an S turn. The first bend 226 and the second bend 228 can be formed by the physician prior to inserting stylet 200 in the longitudinal lumen 216 of the push rod 206. The first bend and second bend can be anywhere from a few degrees up to approximately 90° depending upon the shape of the patient's heart.

Figure 36:
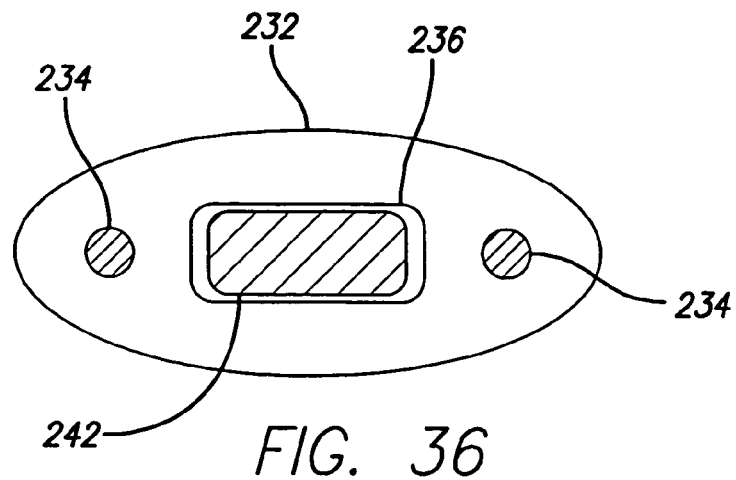
FIG. 36 is a cross-sectional view taken along lines 36-36 depicting the longitudinal lumen of the oval sheath with the push rod inserted therein.
Figure 37:
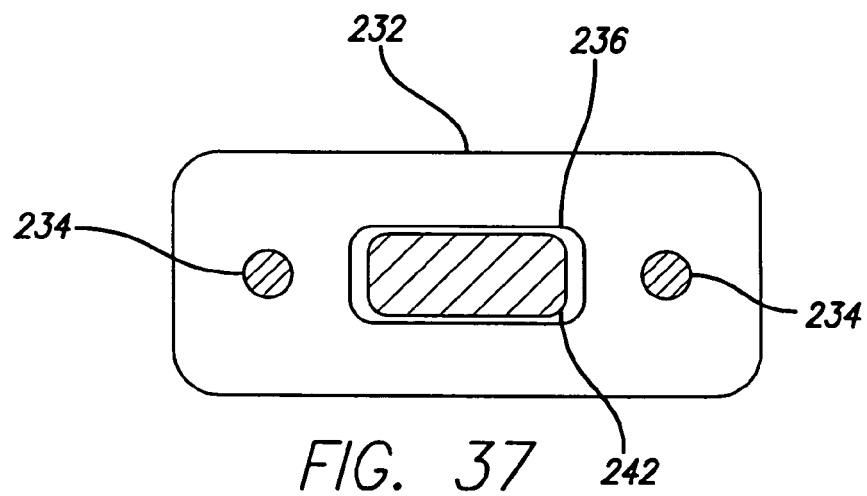
FIG. 37 is a cross-sectional view taken along lines 37-37 depicting a rectangular sheath for receiving a rectangular-shaped push rod.
Figure 38:
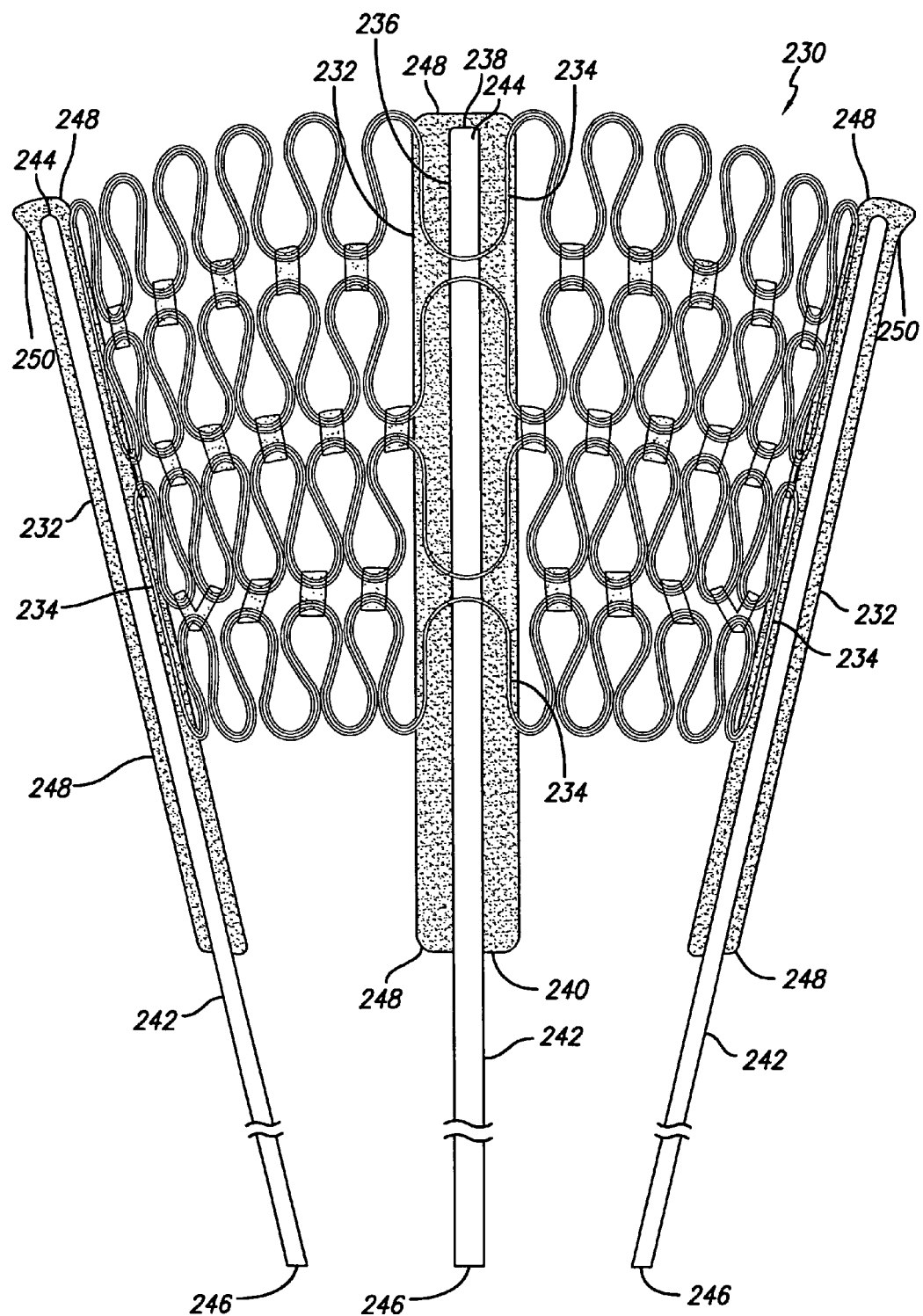
FIG. 38 is an elevational view of a cardiac harness attached to sheaths having longitudinal lumens for receiving push rods.
Figure 39:
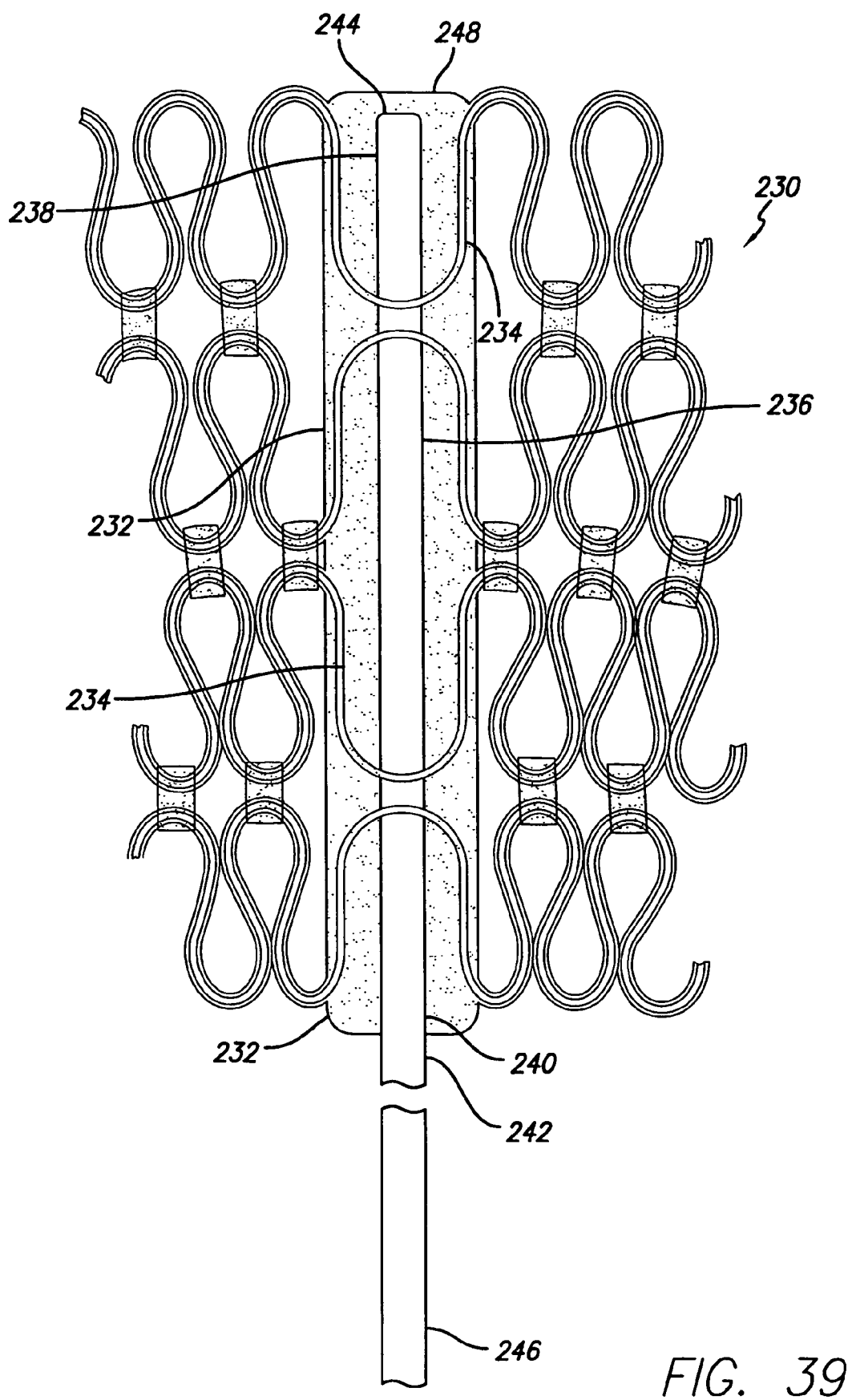
FIG. 39 is an enlarged partial elevational view of the cardiac harness assembly of FIG. 38.
Figure 40:
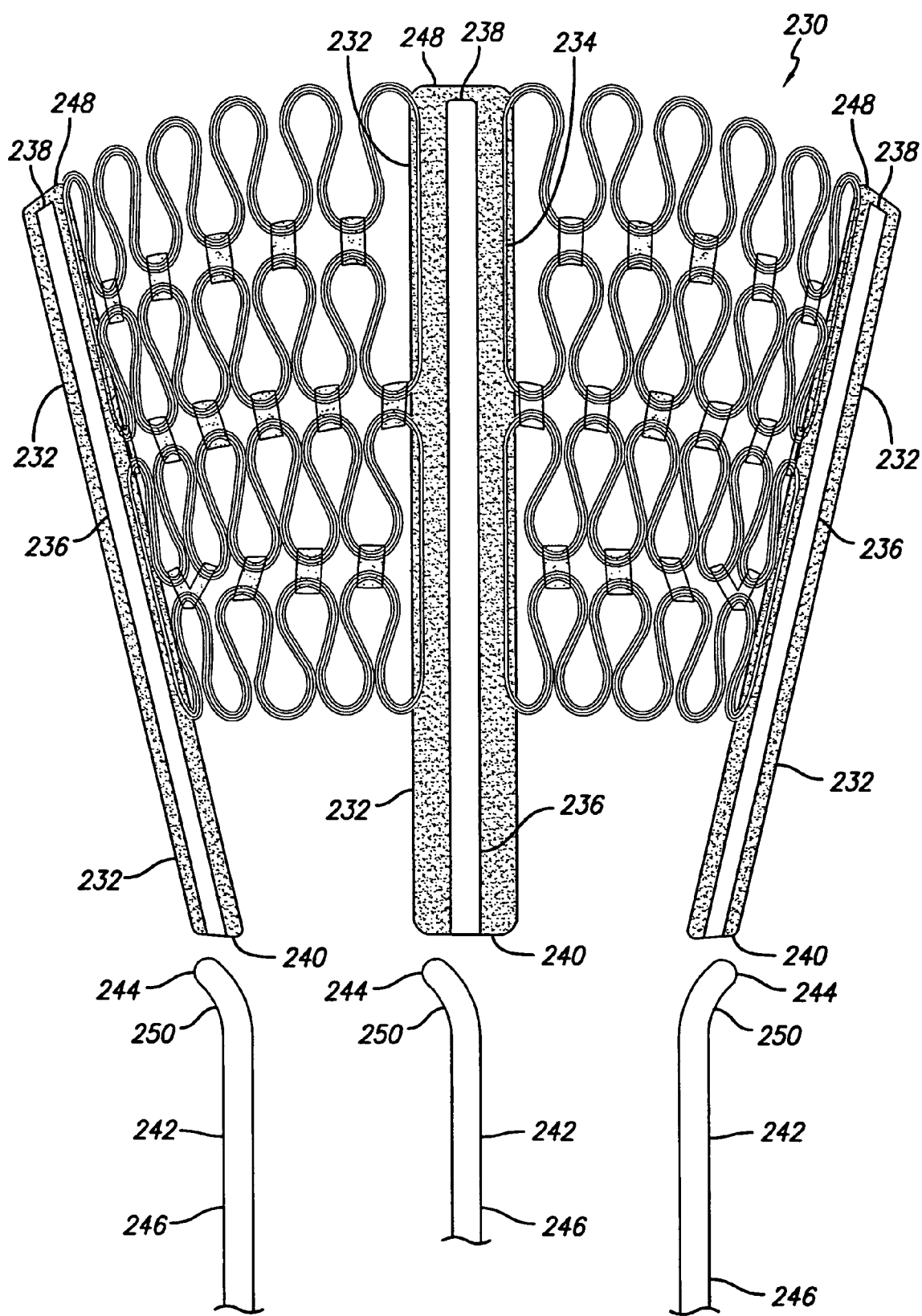
FIG. 40 is an elevational view depicting a cardiac harness attached to sheaths having longitudinal lumens for receiving push rods.
Figure 41:
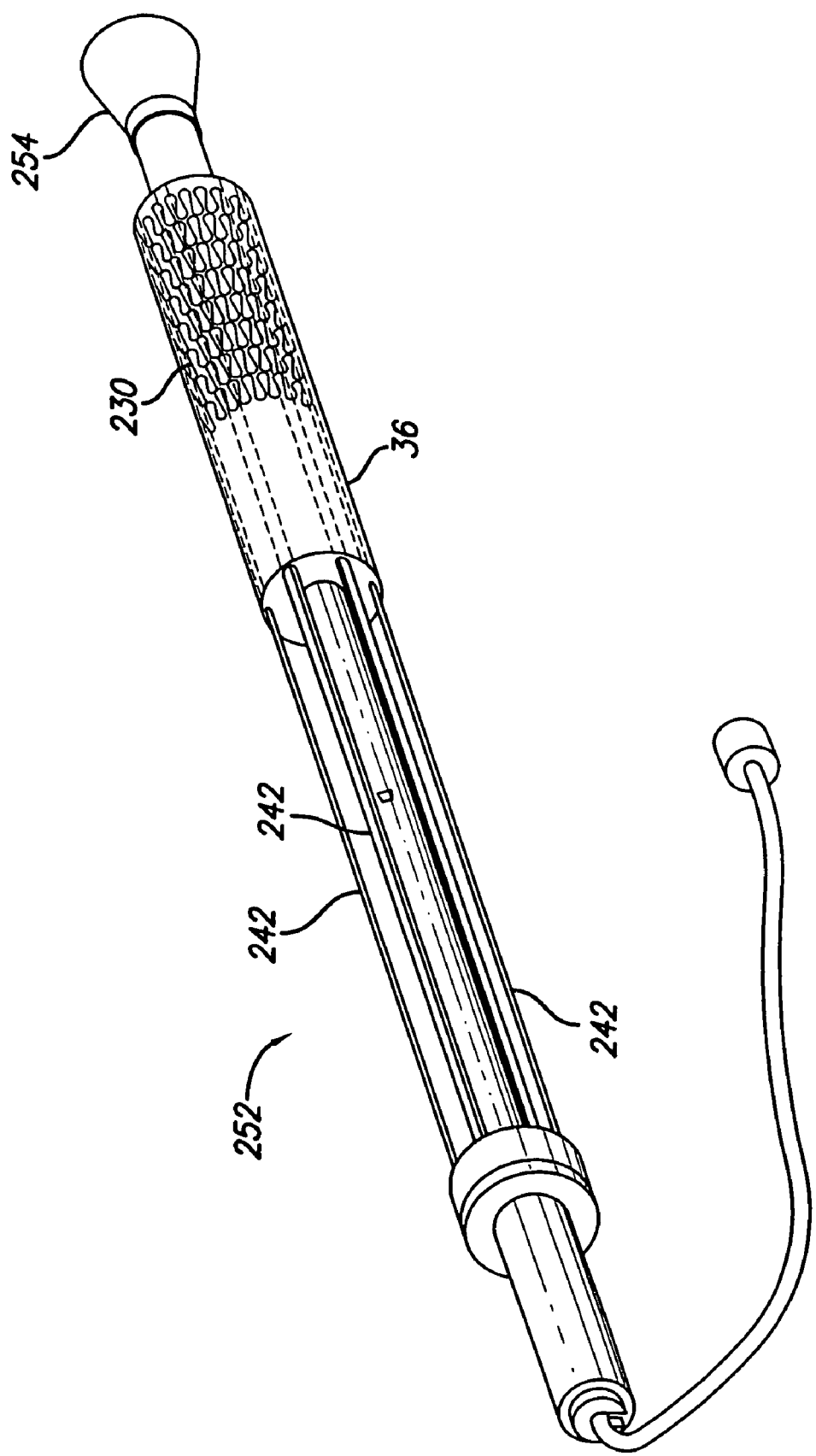
FIG. 41 is a perspective elevational view of a delivery device having a cardiac harness mounted therein.
Figure 42:
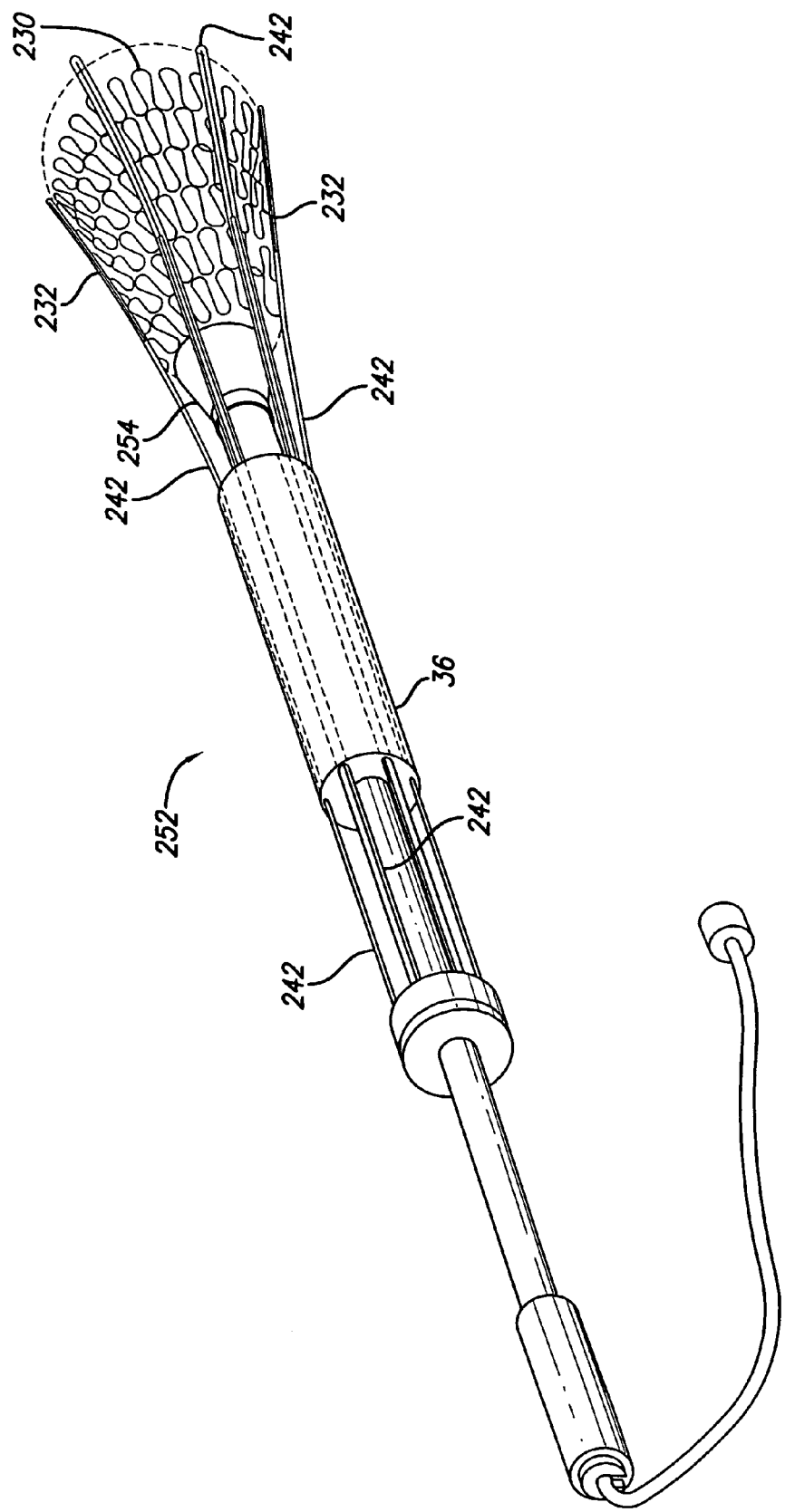
FIG. 42 is a perspective elevational view of the cardiac harness assembly being advanced distally out of the delivery device and onto the heart wherein the cardiac harness is attached to sheaths having longitudinal lumens for receiving the push rods.
Figure 43:
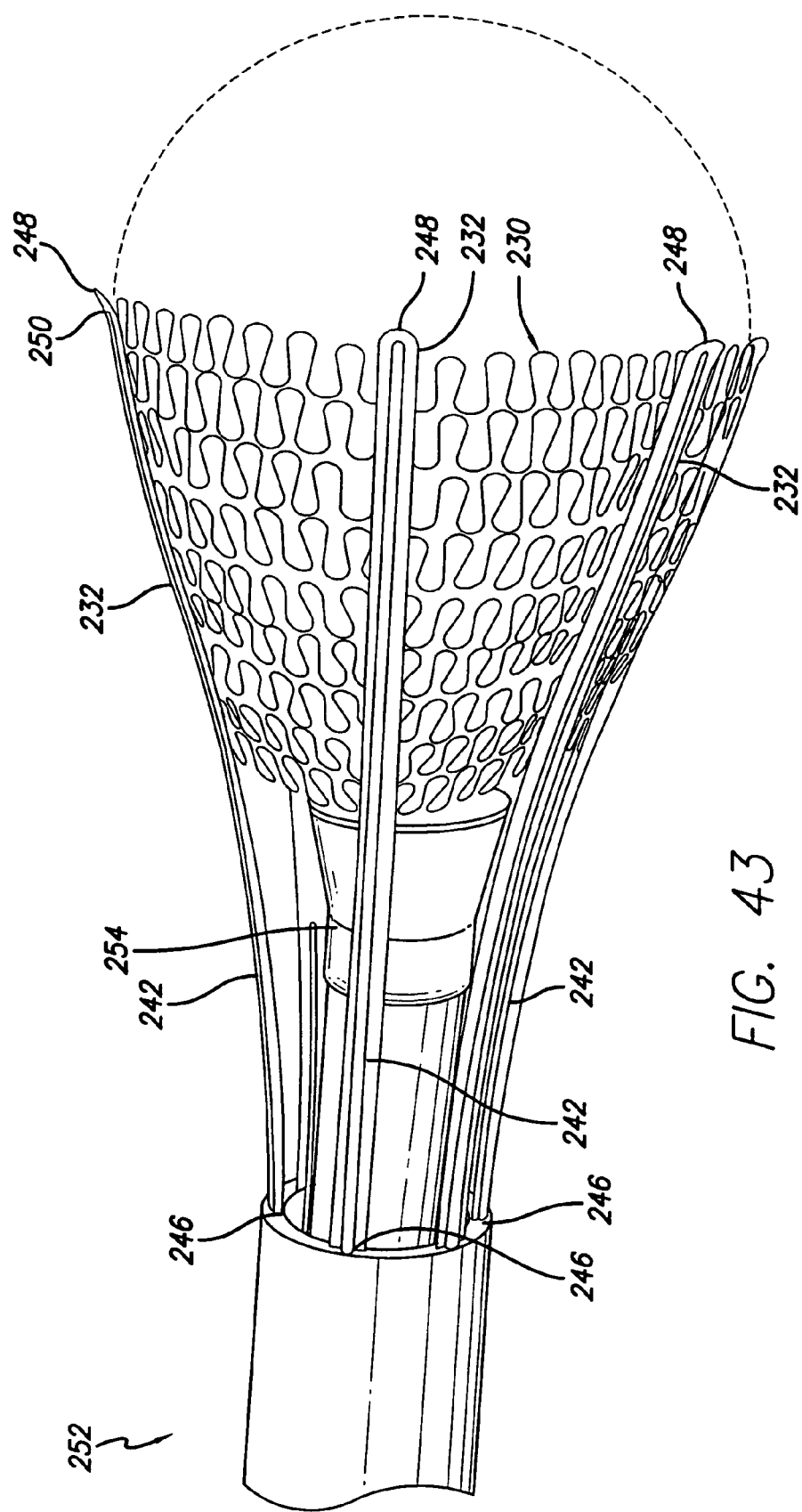
FIG. 43 is a partial elevational view of the delivery device of FIG. 41 wherein the cardiac harness is mounted on the heart and the push rods are positioned in the longitudinal lumens of the sheath.
Figure 44:
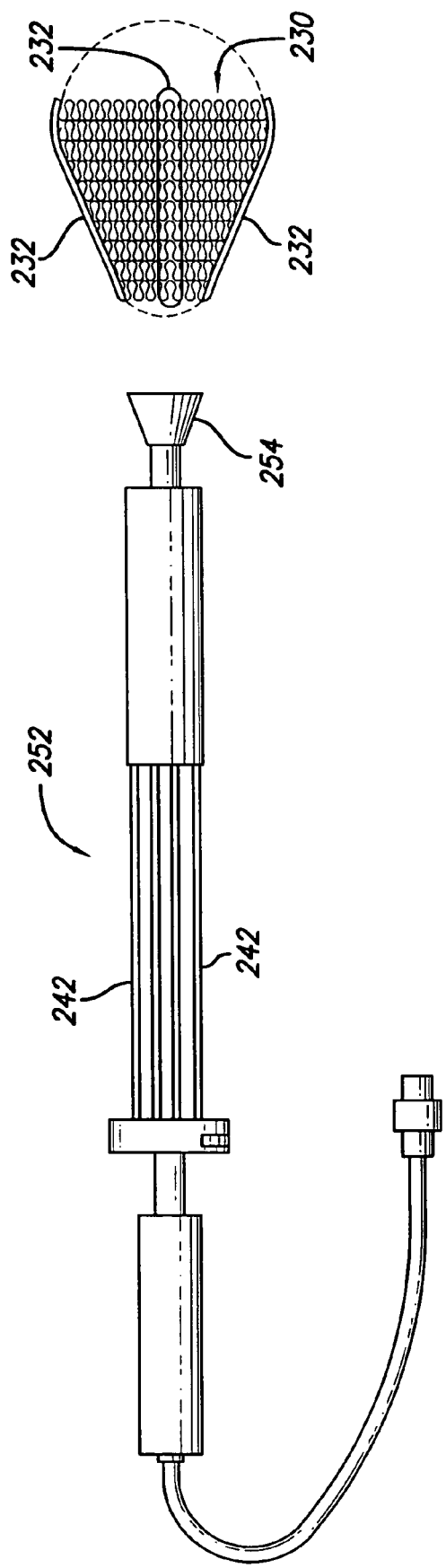
FIG. 44 is an elevational view depicting the push rods being withdrawn into the delivery device and having been withdrawn from the sheaths on the cardiac harness.

In another embodiment, as shown in FIGS. 35A-44, a cardiac harness 230 is permanently connected to sheaths 232. The sheaths are formed from a biocompatible polymer material such as silicone rubber, silicone, polyethylene, polyurethane, polyethylene, teraphthalate, and the like, and which is highly flexible. Struts 234 of the cardiac harness 230 are molded into the sheaths 232 so that the cardiac harness is permanently attached to the sheaths. At least some of the sheaths 232 have a longitudinal lumen 236 having a distal end 238 and a proximal end 240. As previously described, the longitudinal lumen 236 can be tapered so that the proximal end 240 of the longitudinal lumen has a greater transverse cross-sectional area than the distal end 238 of the longitudinal lumen 236. As shown in FIGS. 36 and 37, the transverse cross-section of the sheaths 232 can have an oval shape or a rectangular shape, or any other geometric shape that is compatible with the present invention. An oval shape and a rectangular shape (with rounded corners) is flat enough to rest against the epicardial surface of the heart and maintain a low profile when mounted on the heart. In this embodiment, push rods 242 slidably extend into the longitudinal lumen 236 for the purpose of delivering the cardiac harness to the heart. Preferably, the push rods have a distal end 244 and a proximal end 246 where the distal end has a transverse cross-section that is narrower than the transverse cross-section of the proximal end. In other words, the push rods 242 are tapered to correspond to the taper of the longitudinal lumen 236 in the sheaths 232. FIGS. 38-40 show different configurations of the cardiac harness being attached to the sheaths 232 and the associated push rods 242. In the embodiments shown in FIGS. 38-40, the sheaths 232 have a proximal end 248 that extends just past the last row of hinges at the base of the cardiac harness 230. Further, in this embodiment, the struts 234 cross over the sheaths 232, however, there is no metal to metal contact since the struts are encased in a polymer that preferably is the same as the polymer used to form sheaths 232. Thus, even though the struts 234 cross over the sheaths 232, the struts will be covered in silicone rubber and there will be no metal to metal contact. As shown for example in FIG. 38, the push rod 242 has been inserted into the longitudinal lumen 236 of the sheaths 232 so that the distal end 244 of the push rod extends all the way to the distal end 248 of the sheaths. As previously described, with respect to the stylet, the push rod 242 preferably has a bend 250 incorporated into the distal end 244 of the push rod. The bend can be anywhere from several degrees up to approximately 90° in order to assist in pushing the cardiac harness past the apex portion of the heart during delivery and mounting the harness onto the heart. In this embodiment, the cardiac harness 230 is delivered and mounted onto the heart in much the same manner as previously described. Thus, referring to FIGS. 41-44, the cardiac harness 230 is mounted in a delivery device 252 in a compact configuration with the push rods 242 extending into the longitudinal lumen 236 of the sheaths 232. After the suction cup 254 is attached to the heart, preferably at or near the apex of the heart, the push rods 242 are advanced out of the delivery device 252 and in the process push the cardiac harness 230 over the apex of the heart and onto the epicardial surface of the heart and underneath the pericardium. As the push rods 242 are further advanced in a distal direction, the push rods 242 continue to push on the sheaths 232 to provide a uniform pushing motion to advance the cardiac harness 230 onto the heart. While the number of push rods can vary, preferably six or eight push rods, and corresponding sheaths 232, are used to deliver the harness 230 and mounted onto the heart. After the cardiac harness is positioned onto the heart, the push rods 242 are withdrawn in a proximal direction back into the delivery device 252 and the suction or vacuum attaching the suction cup 254 to the heart is released so that the delivery device 252 can be removed from the patient. As previously described, the entire procedure of delivering and mounting the harness onto the heart is done in a minimally invasive manner.

In further keeping with the invention, and as shown in FIG. 40 for example, the distal end 244 of the push rods 242 can be formed with a bend 250 to facilitate advancing the cardiac harness over the heart. Thus the attending physician can form the distal end of the push rod with a bend 250 of anywhere from several degrees up to approximately 90° prior to inserting the push rods into the sheaths 232. Alternatively, the distal end 244 of the push rods 242 can come with a bend 250 that is predetermined by the manufacturer so that the physician does not have to adjust the bend 250 for a particular patient's needs. If a particular patient has a heart that is substantially spherical at or near the apex portion of the heart, it may require a bend 250 in the range of 30° to 90°. The physician can select from among various available ranges supplied by the manufacturer that would accommodate a bend of over 30°. Thus, as the push rods 242 are advanced out of the delivery device 252, the bends 250, previously restrained by packaging in the delivery device 252, will re-form as the bends 250 exit the delivery device. The bends then will correspondingly shape the distal end 248 of the sheaths 232 to accommodate the severe curve in the apex region of the heart as the push rods are advanced further to push the cardiac harness onto the heart.

Figure 45:
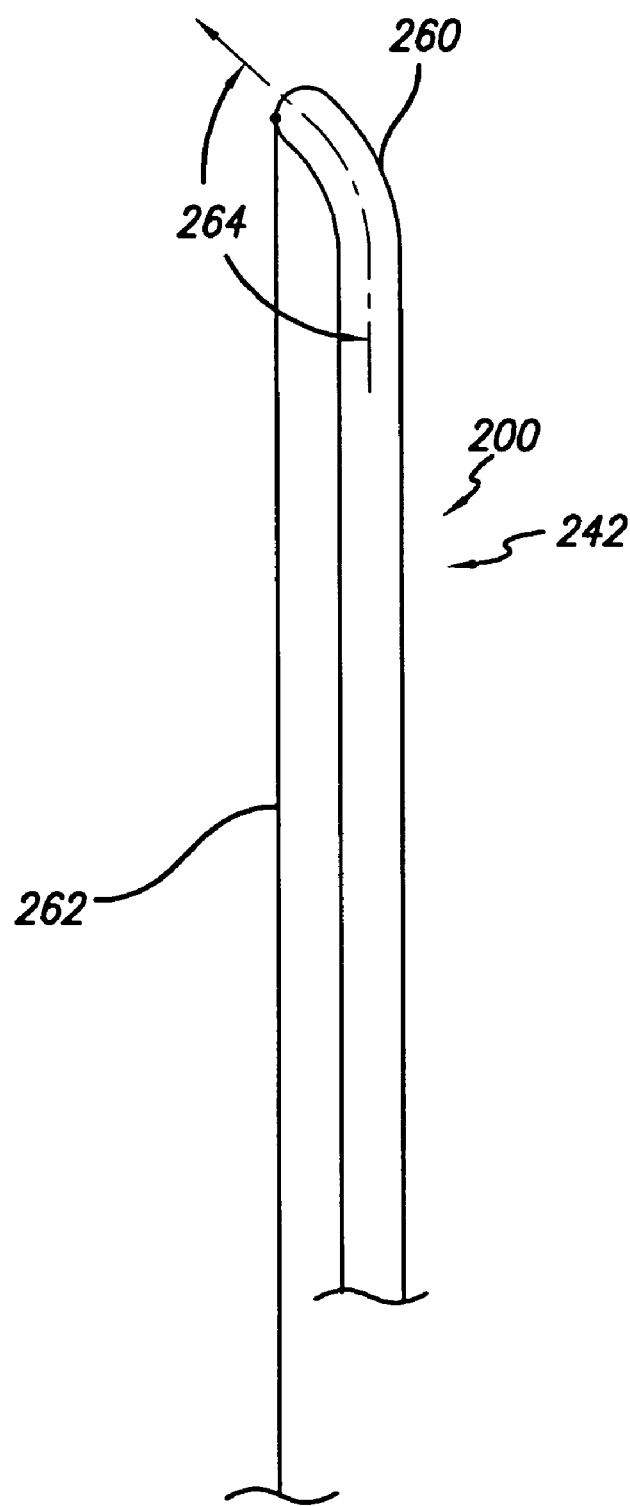
FIG. 45 is a partial elevational view depicting a push rod with a wire attached to the distal end for forming a bend in the distal end of the push rod.

In another embodiment, shown in FIG. 45, the stylet 200 or the push rods 242 have a distal end 260 that is flexible that can form bend 262. In this embodiment, a wire 262 (or suture) of biocompatible material is attached to the distal end 260 of the stylet 200 or push rods 242. The wire 262 extends out of the patient and is pulled in a proximal direction by the physician during delivery of the cardiac harness in order to form a desired bend 264 in the distal end 260. Again, the bend can 264 can range anywhere from a few degrees to approximately 90° in order to fit the particular needs of a patient.

In another embodiment, shown in FIGS. 46-51, the cardiac harness 230 is mounted on any of the push rods previously disclosed herein. In this embodiment, the section cup 270 has been modified to facilitate the bending of the push rods in order to navigate around the severe bend or curve at the apex region of the heart. More specifically, the suction cup 270 has a first flared member 272 that is formed of a soft and pliable polymer, preferably silicone rubber or a similar material, which will engage a portion of the heart, typically the apex of the heart. The first flared member 272 is somewhat tapered from its proximal end 274 to the distal end 276. The distal end 276 of the first flared member has a diameter that is greater than the diameter of the proximal end 274 of the first flared member, as can be seen in FIGS. 47 and 48. The suction cup 270 also includes a second flared member 278 that preferably is integral with and surrounding an outer surface 280 of the first flared member 272. The second flared member has an outer surface 282 that flares radially outwardly to facilitate bending of the previously described push rods 206 and 242 in bending radially outwardly as the cardiac harness is pushed onto the heart. The outer surface 282 of the second flared member 278 can be substantially flat or straight, or can have a slight curve again to assist the push rods in bending anywhere from approximately 10° up to about 90° in order to navigate around the apex region of the heart as the cardiac harness is pushed onto the heart. The second flared member 278 can be formed from any suitable polymer such as silicone rubber, polyurethane, silicone, polyethylene, polyurethane, polyethylene, teraphthalate, and the like. Further, the angle between the longitudinal axis of the delivery device and the second flared member 278 can range from approximately 30° up to about 75°, which would be sufficient to cause the push rods to flare radially outwardly at an angle from approximately 10° to about 90° as the cardiac harness is pushed onto the heart. As shown in FIGS. 49 and 50, as the cardiac harness is advanced distally out of the delivery device 284, the push rods 206, 242 slidingly engage the outer surface 280 of the second flared member 278. As the push rods slidingly engage the outer surface 282, the push rods bend radially outwardly thereby opening the cardiac harness 230 so that the push rods and the cardiac harness open up to slide over the apex region of the heart. As the push rods extend past the rim 286 of the second flared member 278 the push rods will tend to turn back onto the surface of the heart, preferably the epicardial surface 222 of the heart. Further, the pericardium 224 will have a tendency to press on the push rods so that the push rods will slidingly engage the epicardial surface 222 of the heart 220 as the push rods are further advanced past the rim 286 of the second flared member 278. In essence, the push rods will make an S turn as the push rods initially bend along the flared outer surface 282 of the second flared member 278 and then turn back onto the epicardial surface of the heart as the push rods extend distally past the rim 286 and are pressed onto the epicardial surface 222 by the pericardium 224.

The distal end 276 of the first flared member 272 preferably has a diameter in the range of about 1 cm up to about 6 cm while the distal end 288 of the second flared member 278 has a diameter in the range of about 3 cm up to about 9 cm. The diameters of the flared members can vary depending upon the application and the size of the patient's heart.

Figure 51:
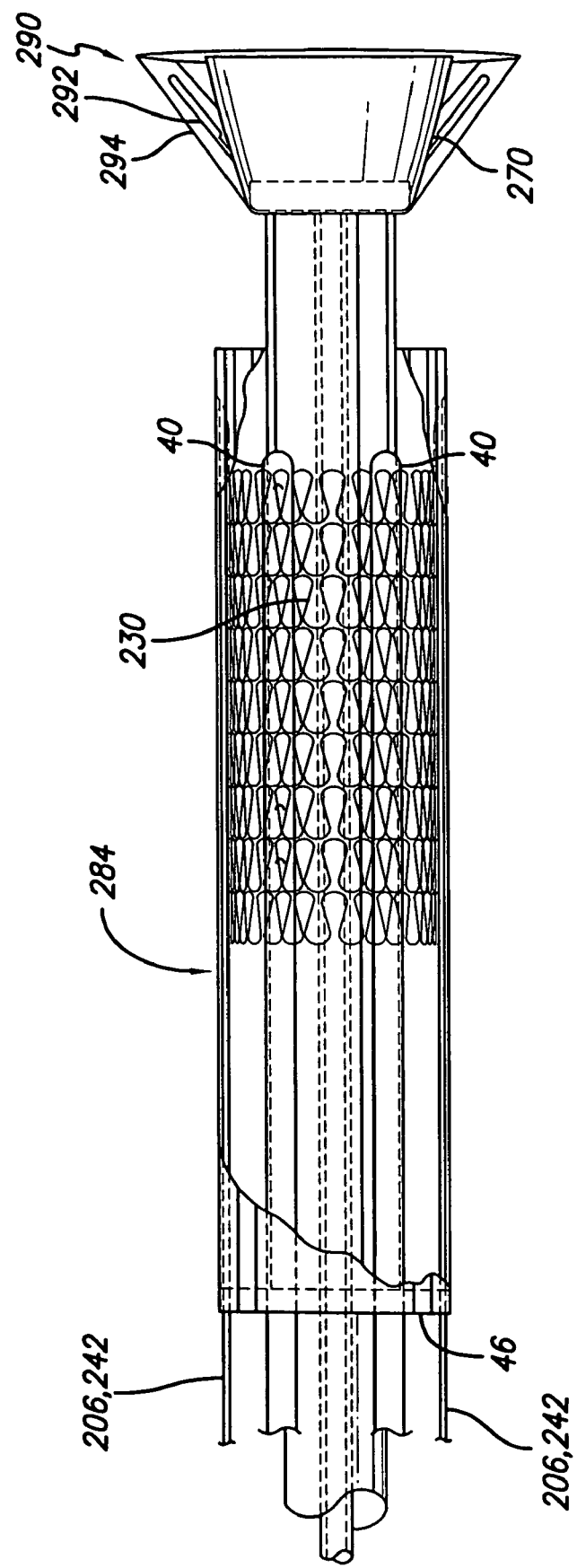
FIG. 51 is a partial side elevational view of the suction cup with an inflatable flared portion.
Figure 52:
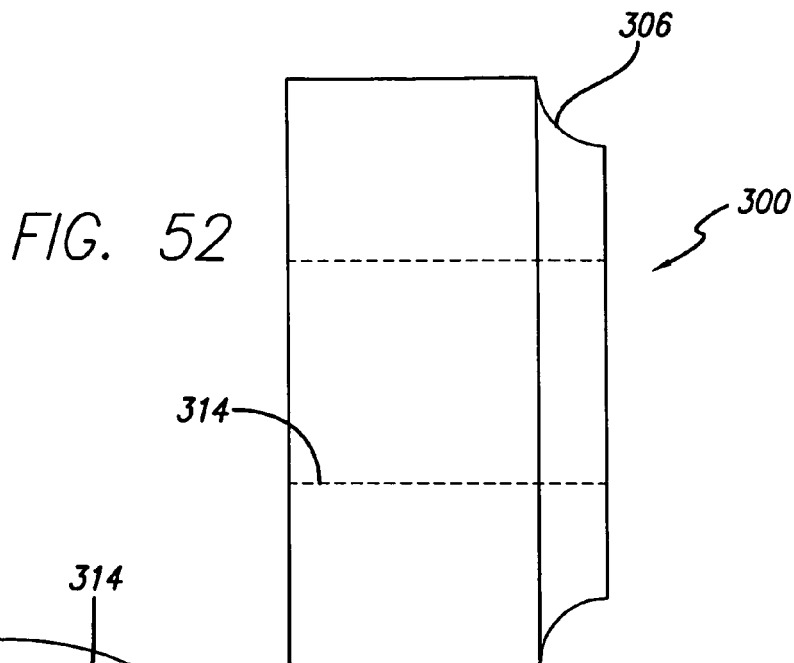
FIG. 52 is a side view depicting annular ring having a bevel edge for maintaining the bend in the distal end of the push rods.
Figure 53:
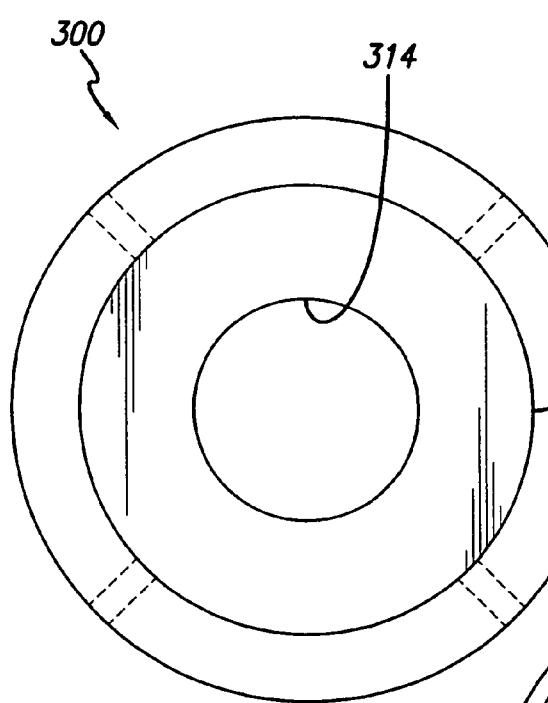
FIG. 53 is a top view of the annular ring depicting the bevel edge.
Figure 54:
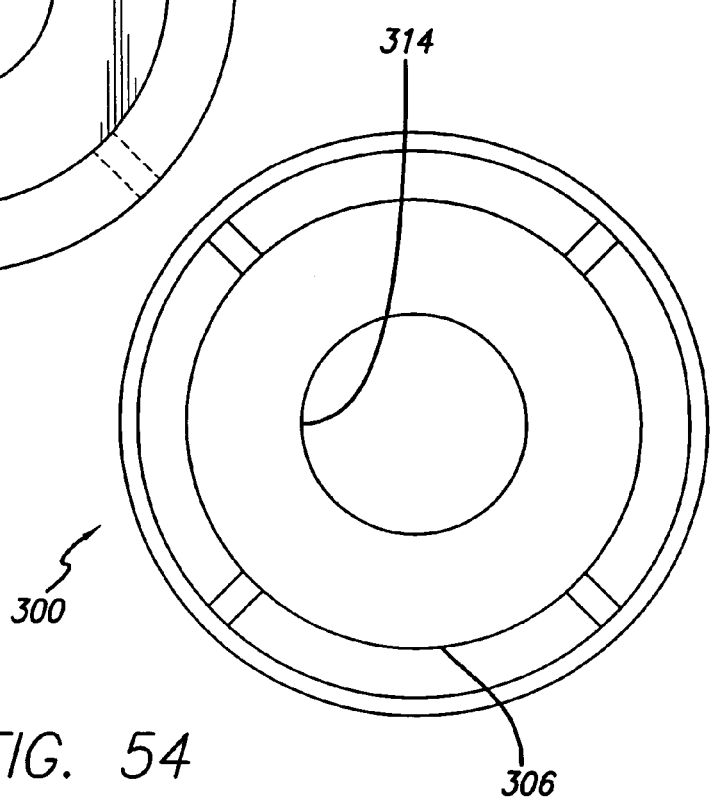
FIG. 54 is a bottom view depicting the annular ring having an opening for receiving the suction cup.
Figure 55:
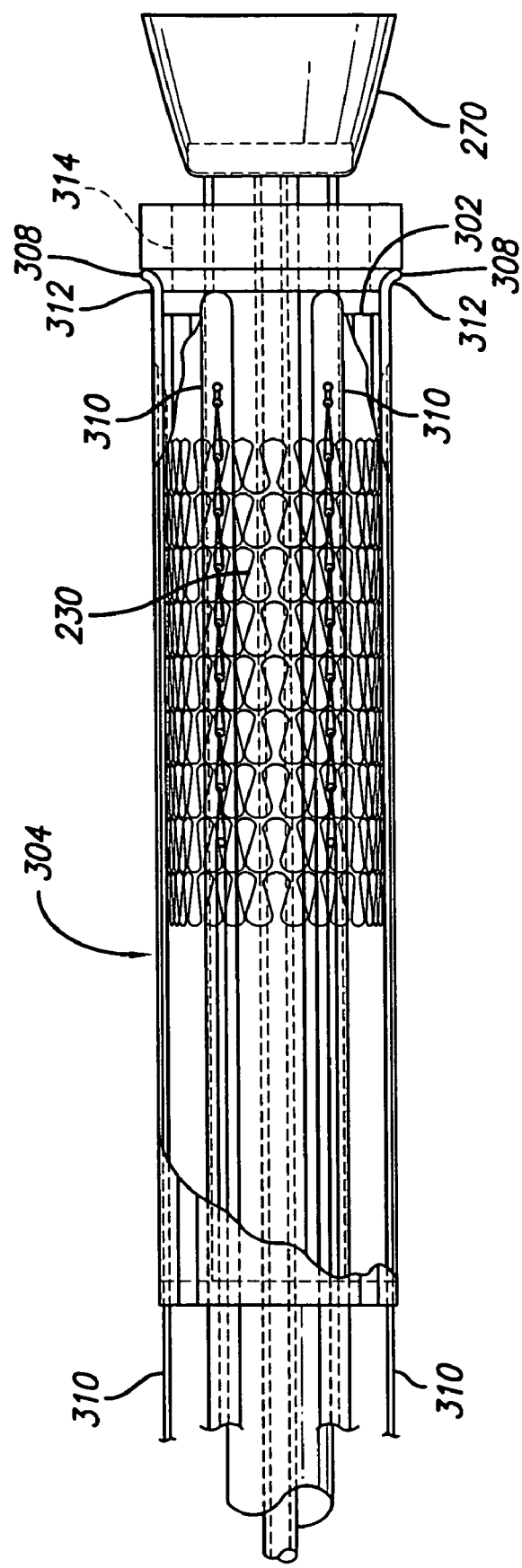
FIG. 55 is a partial side elevational view depicting the annular ring releasably attached to the delivery device.

In another embodiment, shown in FIG. 51, suction cup 270 has a first flared member 272 and an inflatable flared member 290. The inflatable flared member 290 is substantially the same a the second flared member 278, except that the inflatable flared member has a cavity 292 that can be filled with a liquid, such as saline or other non-expansible liquid, or air, in order to inflate the flared member to increase the angle between the longitudinal axis of the delivery device and the angle of the outer surface 294 of the inflatable flared member. The amount of fluid to be injected into the cavity 292 can vary, depending upon the size of the patient's heart and the angle, relative to the longitudinal axis, that is required to cause the push rods to slide along the outer surface 294 of the inflatable flared member 290. Thus, if the patient's heart is particularly enlarged, cavity 292 can be completely filled so that the maximum angle between the outer surface 294 and the longitudinal axis is created. As with the other embodiments disclosed herein, the angle can range from approximately 10° up to about 90° depending on the particular application.

In another embodiment, shown in FIGS. 52-55, an angular ring 300 is provided to maintain the curvature in the distal end of the push rods. More specifically, annular ring 300 is sized to fit on the distal end 302 of delivery device 304. The delivery device 304 is substantially the same as the other delivery devices disclosed herein, and operates substantially the same. In this embodiment, angular ring has a double edge 306 that preferably is curved and that engages the distal end 308 of the push rod 310. After the cardiac harness 230 has been mounted on the push rods 310 and loaded into the delivery device 304, the push rods will have a bend at the distal end 308 that will assist the push rods in making the initial turn or bend at the apex region of the heart when the push rods are advanced distally over the heart to deliver the cardiac harness. In order to maintain the bend 312 in the distal end 308 of the push rods, especially during packaging, the annular ring 300 is mounted on the distal end 302 of the delivery device 304. The annular ring has an opening 314 that is sized to permit the suction cup previously described, and any flared member previously described, to pass through opening 314 when the annular ring is mounted onto the delivery device. When the delivery device is removed from its packaging, annular ring 300 is advanced distally past the suction cup 270 and discarded. The bevel edge 306 of the annular ring 300 will maintain the bend 312 in the distal end of the push rods 310.

Figure 56:
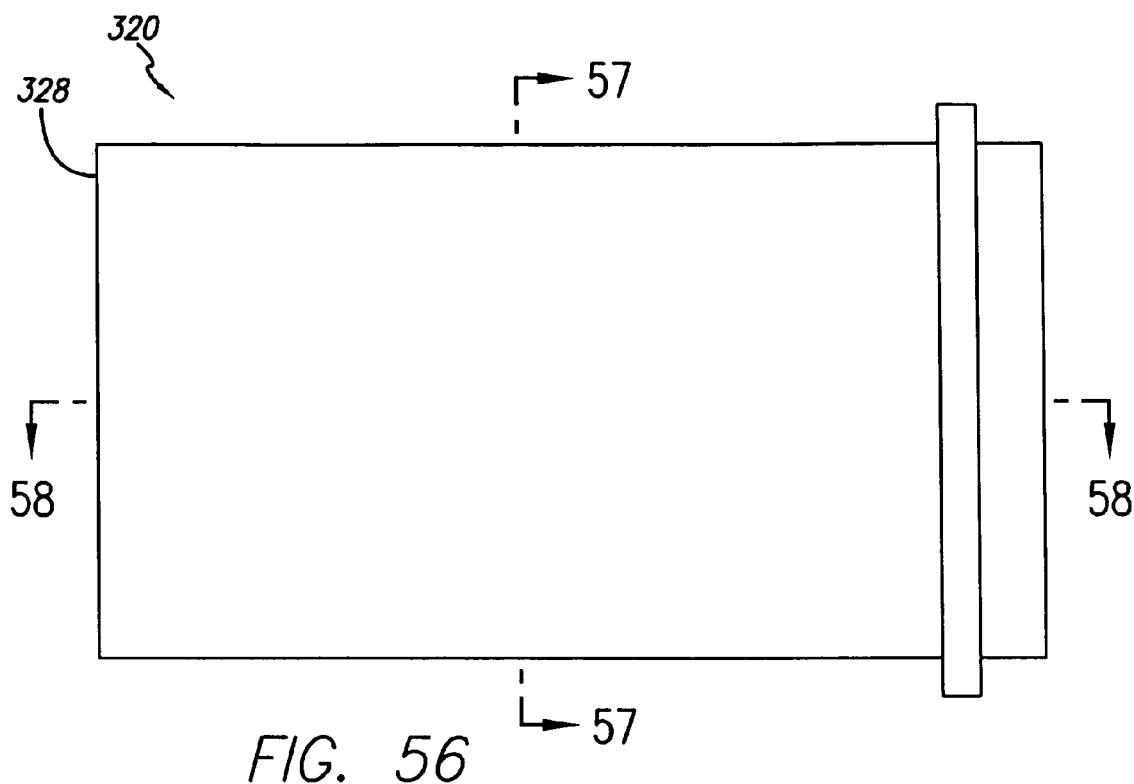
FIG. 56 is a side elevational view of a housing for slidably receiving push rods.
Figure 57:
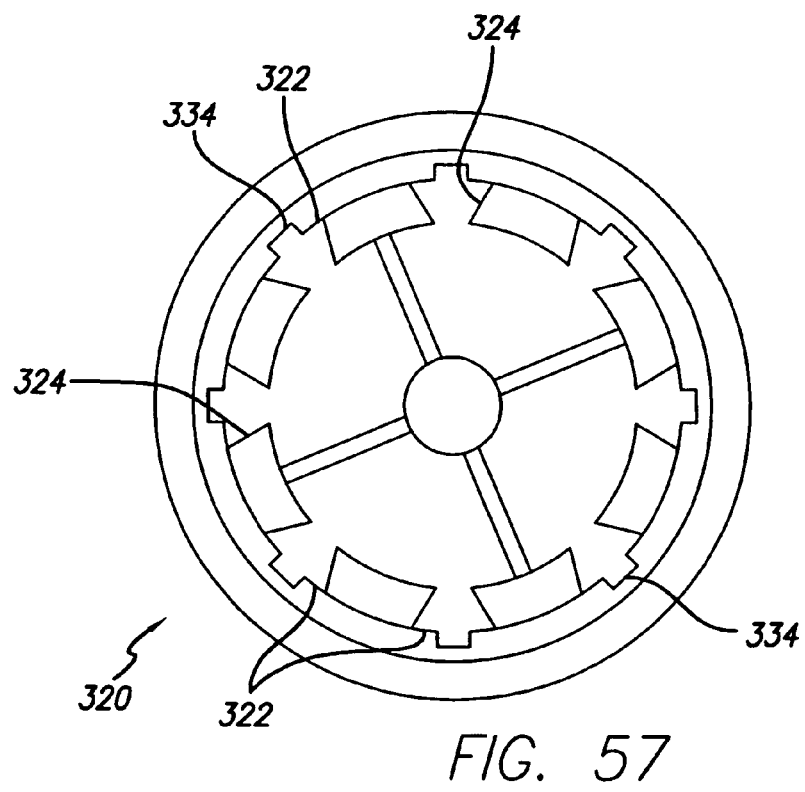
FIG. 57 is a cross-sectional view taken along lines 57-57 depicting dovetail slots for receiving dovetail-shaped push rods.
Figure 58:
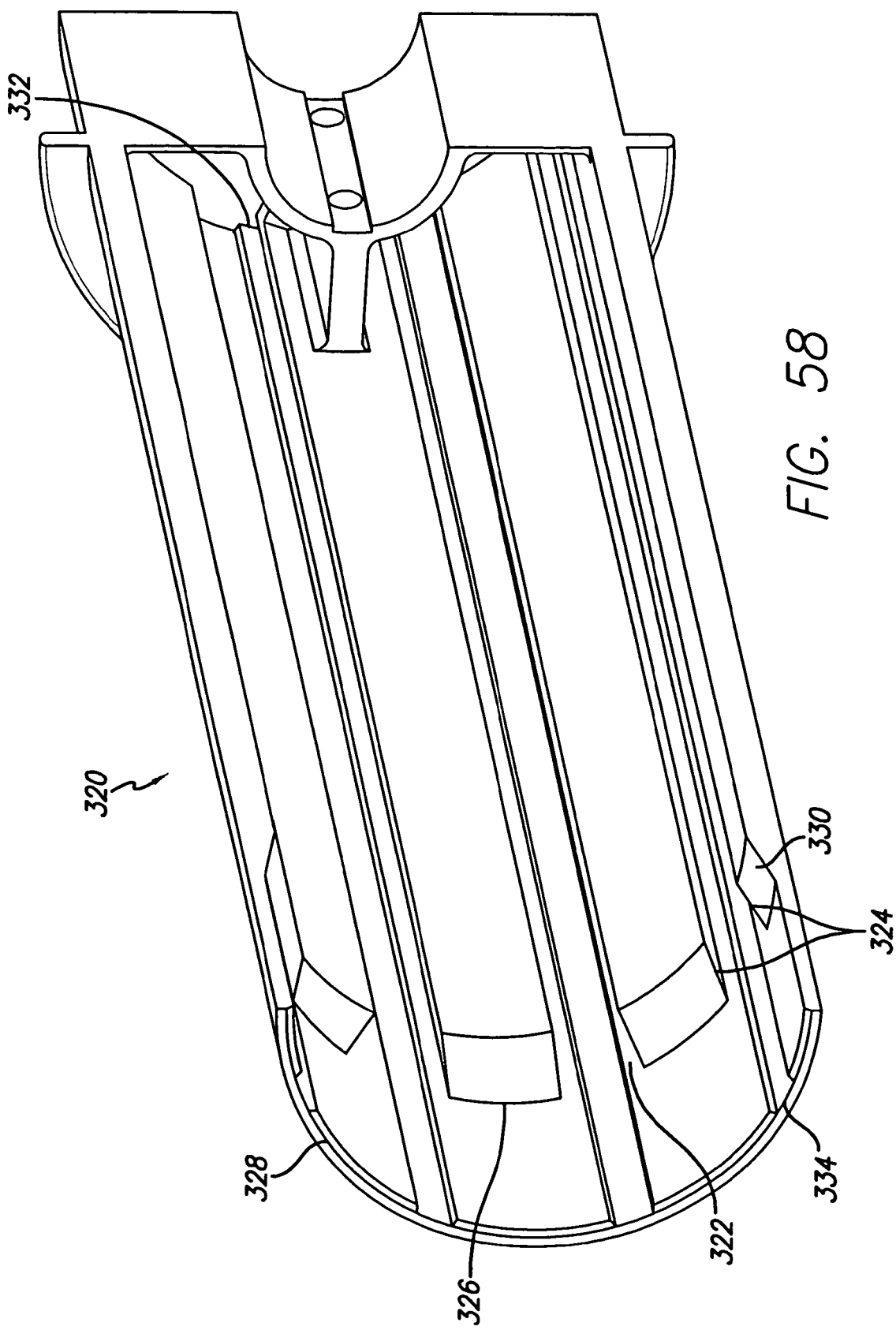
FIG. 58 is a perspective transverse cross-sectional view taken along line 58-58 depicting the dovetail slots for slidably receiving push rods.

In another embodiment, shown in FIGS. 56-58, housing 320, which carries the cardiac harness previously described, includes slots 322 for slidably receiving the previously disclosed push rods. More specifically, slots 322 have a dovetail 324 configuration and the transverse cross-section of the previously disclosed push rods have a matching dovetail cross-section. Thus, when the push rods slide through slots 322, the dovetail 324 ensures that the push rods do not move out of the slots 322 in a circumferential or lateral direction. The slots 322 are analogous to rails so that the push rods follow along the slots in a longitudinal direction without fear that any portion of the push rod will shift circumferentially or laterally during delivery of the cardiac harness. Further, a recess 326 is formed at the distal end 328 of housing 320 whereby the slots and so that the distal end of the push rods can be pulled back into the housing 320. Slots 322 have a distal end 330 that coincides with recess 326, and a proximal end 332 that is essentially the proximal end of housing 320. The recess 326 is approximately 2.54 cm (approximately 1 inch) from the distal end 328 of the housing 320. For those embodiments where the cardiac harness is laced onto the push rods, channel 334 is formed in the housing 320 at the base of slots 322. The channel 334 is recessed enough for the lacing to slide through without being pinched between the push rod and the bottom of slots 322. The number of slots 322 will correspond to the number of push rods, and typically will comprise four, six, or eight slots 322. More or fewer slots (and an odd number of slots and push rods) also are contemplated depending upon a particular application.

Although the present invention has been described in the context of a preferred embodiment, it is not intended to limit the invention to the embodiment described. Accordingly, modifications may be made to the disclosed embodiment without departing from the spirit and scope of the invention. For example, any of a variety of suitable releasable stitches, or other releasing mechanisms, may be used. It is also contemplated that various combinations or subcombinations of the specific features and aspects of the embodiments discussed herein may be made. Accordingly, various features and aspects of the disclosed embodiments can be combined with or substituted for one another in order to form varying modes of the invention. In addition, although the illustrated device 30 is well suited for delivering a cardiac harness through a minimally invasive procedure, the illustrated device 30, or alternative arrangements thereof, may also be used in an open chest procedure. Accordingly, the invention is intended to be defined only by the claims that follow.

What is claimed:

1. An assembly for delivering and mounting a cardiac harness on a heart, comprising:
    an elongate body having a proximal portion and a distal portion, the elongate body having a cavity sized to contain a cardiac harness in a compressed configuration;
    the cardiac harness having a plurality of elongate sheaths, the sheaths having elongate lumens;
    the cardiac harness being permanently attached to the sheaths;
    a plurality of elongate push rods longitudinally movable with respect to the elongate body, each lumen of each sheath slidably receives one of the elongate push rods such that advancement of the push rods in a distal direction moves the cardiac harness from the compressed configuration in the cavity to an expanded configuration outside the cavity; and
    the push rods are tapered from a larger cross-section at a proximal end to a relatively narrower cross-section at a distal end so that at least a portion of the push rods frictionally slide into corresponding lumens of the sheaths.

2. The assembly of claim 1, wherein each push rod is configured to frictionally slide into the corresponding lumen of the sheath.

3. The assembly of claim 1, wherein the sheaths are formed from a polymer.

4. The assembly of claim 3, wherein the polymer is taken from the group of polymers consisting of silicone rubber, silicone, polyethylene, polyurethane, polyethylene, teraphthalate, and the like.

5. The assembly of claim 1, wherein the elongate body includes a flange for engaging a proximal end of the sheaths so that as the push rods are withdrawn proximally from the sheaths, the flange prevents the sheaths and the cardiac harness from sliding off of the heart.

6. The assembly of claim 1, wherein the sheaths have a transverse cross-sectional shape that is generally elliptical.

7. The assembly of claim 1, wherein the sheaths have a transverse cross-sectional shape that is generally rectangular.

8. The assembly of claim 1, wherein a positioning arrangement is configured to secure the elongate body in a desired position relative to the heart.

9. The assembly of claim 8, wherein the positioning arrangement comprises a suction cup member.

10. The assembly of claim 9, wherein the suction cup member comprises a first flared member having a first diameter and a second flared member having a second diameter, the second diameter being larger than the first diameter.

11. The assembly of claim 10, wherein the second flared member is inflated to provide a variable second diameter.

12. The assembly of claim 1, wherein the distal portion of the elongate body further comprises a ramp member for biasing the push rods radially outwardly as the push rods are advanced distally out of the cavity.

13. The assembly of claim 12, wherein the ramp member is inflatable to vary the size of the ramp member.

14. The assembly of claim 1, wherein each push rod has a proximal region, a central region, and a distal region, the proximal region being the most stiff, the central region being less stiff than the proximal region, and the distal region being the least stiff.

15. The assembly of claim 14, wherein the push rods have varying degrees of stiffness along the length so that as the push rods are advanced over the heart, at least a portion of the push rods form an S configuration.

16. The assembly of claim 1, further comprising a handle and a control assembly, the handle being fixed to the proximal portion of the elongate body and the control assembly supporting the plurality of elongate push rods.

17. An assembly for delivering and mounting a cardiac harness on a heart, comprising:
    an elongate body having a proximal portion and a distal portion, the elongate body having a cavity sized to contain a cardiac harness in a compressed configuration;
    a suction cup member proximate the distal end of the elongate body, the suction cup member having a first flared member;
    a second flared member proximate the distal end of the elongate body;
    a plurality of push rods longitudinally movable with respect to the elongate body and releasably connected to the cardiac harness; and
    the push rods slidingly engaging the second flared member as the push rods are advanced distally out of the cavity to advance the cardiac harness onto the heart.

18. The assembly of claim 17, wherein as the push rods slidingly engage the second flared member, distal ends of the push rods flare radially outwardly thereby opening the cardiac harness as the push rods advance the cardiac harness onto the heart.

19. The assembly of claim 17, wherein the first flared member has a first diameter and the second flared member has a second diameter, the second diameter being greater than the first diameter.

20. The assembly of claim 19, wherein the second flared member is inflated to provide a variable second diameter.

21. The assembly of claim 19, wherein the first flared diameter is in the range of about 1 cm to about 6 cm and the second flared diameter is in the range of about 3 cm to about 9 cm.

* * * * *

UNITED STATES PATENT AND TRADEMARK OFFICE
CERTIFICATE OF CORRECTION

| | |
|---|---|
| PATENT NO. | : 7,229,405 B2 |
| APPLICATION NO. | : 11/481567 |
| DATED | : June 12, 2007 |
| INVENTOR(S) | : Lilip Lau and Joshua Wallin |

It is certified that error appears in the above-identified patent and that said Letters Patent is hereby corrected as shown below:

<u>Page 5</u>, U.S. PATENT DOCUMENTS, delete "U.S. Appl. No. 10974,237" and insert -- U.S. Appl. No. 10/974,237--.

<u>Page 4</u>, FOREIGN PATENT DOCUMENTS, delete "WO 01/95380" and insert --WO 01/95830--.

<u>In the Drawings,</u> sheet 7 of 42, FIG. 7A, top left quadrant, delete "114c" and insert -- 114e--.

<u>Column 6,</u>
Line 39, delete "a side" and insert --an inside--.

<u>Column 14,</u>
Line 56, delete "tight" and insert --right--.

<u>Column 18,</u>
Line 33, delete "dump member" and insert --pump member--.

<u>Column 18,</u>
Line 40, delete "shall" and insert --shaft--.

<u>Column 21,</u>
Line 18, delete "polyethylene, teraphthalate," and insert --polyethylene teraphthalate,--.

<u>Column 23,</u>
Line 15, delete "polyurethane,".

<u>Column 23,</u>
Line 16, delete "polyethylene, teraphthalate," and insert --polyethylene teraphthalate,--.

<u>Column 23,</u>
Line 54, delete "a" and insert --as--.

<u>Column 24,</u>
Lines 4-5, delete "angular ring" and insert --annular ring--.

<u>Column 24,</u>
Line 10, delete "angular ring" and insert --annular ring--.

UNITED STATES PATENT AND TRADEMARK OFFICE
CERTIFICATE OF CORRECTION

PATENT NO.        : 7,229,405 B2
APPLICATION NO.   : 11/481567
DATED             : June 12, 2007
INVENTOR(S)       : Lilip Lau and Joshua Wallin It is certified that error appears in the above-identified patent and that said Letters Patent is hereby corrected as shown below:

Column 24,
Line 44, delete "slots and" and insert --slots coincide and--.

Column 25,
Line 41, delete "rnbber" and insert --rubber--.
Lines 42-43, delete "polyethylene, teraphthalate," and insert --polyethylene teraphthalate,--.

Signed and Sealed this

Sixth Day of November, 2007

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,229,405 B2 |
| APPLICATION NO. | : 11/481567 |
| DATED | : June 12, 2007 |
| INVENTOR(S) | : Lilip Lau and Joshua Wallin |

It is certified that error appears in the above-identified patent and that said Letters Patent is hereby corrected as shown below:

<u>Title page</u>, Item [56] U.S. PATENT DOCUMENTS, delete "5,382,528" and insert --5,285,528--.

Signed and Sealed this

Thirteenth Day of January, 2009

JON W. DUDAS
*Director of the United States Patent and Trademark Office*